US009447461B2

(12) United States Patent
Ismagilov et al.

(10) Patent No.: US 9,447,461 B2
(45) Date of Patent: Sep. 20, 2016

(54) ANALYSIS DEVICES, KITS, AND RELATED METHODS FOR DIGITAL QUANTIFICATION OF NUCLEIC ACIDS AND OTHER ANALYTES

(75) Inventors: Rustem F. Ismagilov, Chicago, IL (US); Feng Shen, Chicago, IL (US); Jason E. Kreutz, Chicago, IL (US); Bing Sun, Chicago, IL (US); Wenbin Du, Chicago, IL (US)

(73) Assignees: CALIFORNIA INSTITUTE OF TECHNOLOGY, Pasadena, CA (US); UNIVERSITY OF CHICAGO, Chicago, IL (US)

( * ) Notice: Subject to any disclaimer, the term of this patent is extended or adjusted under 35 U.S.C. 154(b) by 0 days.

(21) Appl. No.: 13/440,371

(22) Filed: Apr. 5, 2012

(65) Prior Publication Data

US 2012/0264132 A1 Oct. 18, 2012

Related U.S. Application Data

(63) Continuation-in-part of application No. 13/257,811, filed as application No. PCT/US2010/028361 on Mar. 23, 2010.

(60) Provisional application No. 61/516,628, filed on Apr. (Continued)

(51) Int. Cl.
*C12Q 1/68* (2006.01)
*B01L 3/00* (2006.01)
*B01F 13/00* (2006.01)

(52) U.S. Cl.
CPC ......... *C12Q 1/6851* (2013.01); *B01F 13/0094* (2013.01); *B01L 3/5025* (2013.01); *B01L 3/502738* (2013.01); *B01L 2200/027* (2013.01); *B01L 2300/0864* (2013.01)

(58) Field of Classification Search
CPC ............. B01L 2200/027; B01L 3/502738; B01L 2300/0864; B01L 3/5025; B01F 13/00; B01F 13/0094
See application file for complete search history.

(56) References Cited

U.S. PATENT DOCUMENTS

| 2,541,413 | A | 2/1951 | Gorey |
| 3,787,290 | A | 1/1974 | Kaye |
| 3,996,345 | A | 12/1976 | Ullman et al. |
| 4,071,409 | A | 1/1978 | Messing et al. |

(Continued)

FOREIGN PATENT DOCUMENTS

| CN | 2482070 Y | 3/2002 |
| CN | 1886644 A | 12/2006 |

(Continued)

OTHER PUBLICATIONS

Beer et al., "On-Chip Single-Copy Real-Time Reverse-Transcription PCR in Isolated Picoliter Droplets", Anal. Chem., 2008, 80, 1854-1858.

(Continued)

*Primary Examiner* — Jonathan Hurst
(74) *Attorney, Agent, or Firm* — Fenwick & West LLP

(57) ABSTRACT

Provided are devices and methods for effecting processing of samples, including essentially isothermal amplification of nucleic acids, at multiple reaction locations in a single device. In some embodiments, the disclosed devices and methods provide for effecting parallel sample processing in several hundred locations on a single device.

16 Claims, 20 Drawing Sheets

Related U.S. Application Data 5, 2011, provisional application No. 61/518,601, filed on May 9, 2011, provisional application No. 61/262,375, filed on Nov. 18, 2009, provisional application No. 61/162,922, filed on Mar. 24, 2009, provisional application No. 61/340,872, filed on Mar. 22, 2010.

(56) References Cited

U.S. PATENT DOCUMENTS

| | | | |
|---|---|---|---|
| 4,755,363 A | 7/1988 | Fujita et al. | |
| 4,853,336 A | 8/1989 | Saros et al. | |
| 4,963,498 A | 10/1990 | Hillman et al. | |
| 5,026,113 A | 6/1991 | DiCarlo et al. | |
| 5,114,208 A | 5/1992 | Ikeda et al. | |
| 5,169,942 A | 12/1992 | Johnson et al. | |
| 5,185,099 A | 2/1993 | Delpuech et al. | |
| 5,251,670 A | 10/1993 | Bates et al. | |
| 5,264,570 A | 11/1993 | Johnson et al. | |
| 5,478,893 A | 12/1995 | Ghosh et al. | |
| 5,518,892 A | 5/1996 | Naqui et al. | |
| 5,656,493 A | 8/1997 | Mullis et al. | |
| 5,686,315 A | 11/1997 | Pronovost et al. | |
| 5,688,651 A | 11/1997 | Solomon | |
| 5,707,850 A | 1/1998 | Cole | |
| 5,725,017 A | 3/1998 | Elsberry et al. | |
| 5,726,026 A | 3/1998 | Wilding et al. | |
| 5,739,036 A | 4/1998 | Parris | |
| 5,744,305 A | 4/1998 | Fodor et al. | |
| 5,746,978 A | 5/1998 | Bienhaus et al. | |
| 5,772,889 A | 6/1998 | Gjerde et al. | |
| 5,773,258 A | 6/1998 | Birch et al. | |
| 5,805,947 A | 9/1998 | Miyamoto et al. | |
| 5,872,010 A | 2/1999 | Karger et al. | |
| 5,948,624 A | 9/1999 | Rothschild et al. | |
| 5,993,631 A | 11/1999 | Parton et al. | |
| 5,997,636 A | 12/1999 | Gamarnik et al. | |
| 6,013,166 A | 1/2000 | Heller | |
| 6,130,098 A | 10/2000 | Handique et al. | |
| 6,140,053 A | 10/2000 | Koster | |
| 6,146,854 A | 11/2000 | Koster et al. | |
| 6,168,948 B1 | 1/2001 | Anderson et al. | |
| 6,171,785 B1 | 1/2001 | Higuchi | |
| 6,180,372 B1 | 1/2001 | Franzen | |
| 6,197,595 B1 | 3/2001 | Anderson et al. | |
| 6,203,989 B1 | 3/2001 | Goldberg et al. | |
| 6,274,726 B1 | 8/2001 | Laugharn, Jr. et al. | |
| 6,277,648 B1 | 8/2001 | Colpan | |
| 6,300,138 B1 | 10/2001 | Gleason et al. | |
| 6,379,929 B1 | 4/2002 | Burns et al. | |
| 6,391,624 B1 | 5/2002 | Megerle | |
| 6,409,832 B2 | 6/2002 | Weigl et al. | |
| 6,426,230 B1 | 7/2002 | Feistel | |
| 6,436,292 B1 | 8/2002 | Petro | |
| 6,451,610 B1 | 9/2002 | Gorman et al. | |
| 6,465,640 B1 | 10/2002 | Hood | |
| 6,500,617 B1 | 12/2002 | Stemmer et al. | |
| 6,503,707 B1 | 1/2003 | Baxter-Lowe | |
| 6,524,456 B1 | 2/2003 | Ramsey et al. | |
| 6,548,256 B2 | 4/2003 | Lienau et al. | |
| 6,550,497 B2 | 4/2003 | Thiele et al. | |
| 6,565,813 B1 | 5/2003 | Garyantes | |
| 6,567,492 B2 | 5/2003 | Kiselev et al. | |
| 6,569,631 B1 | 5/2003 | Pantoliano et al. | |
| 6,575,188 B2 | 6/2003 | Parunak | |
| 6,606,618 B2 | 8/2003 | Delo | |
| 6,632,653 B1 * | 10/2003 | Astle | 435/287.2 |
| 6,638,408 B1 | 10/2003 | Speicher et al. | |
| 6,702,256 B2 | 3/2004 | Killeen et al. | |
| 6,705,357 B2 | 3/2004 | Jeon et al. | |
| 6,716,642 B1 | 4/2004 | Wu et al. | |
| 6,717,136 B2 | 4/2004 | Andersson et al. | |
| 6,720,187 B2 | 4/2004 | Bedingham et al. | |
| 6,737,026 B1 * | 5/2004 | Bergh | B01F 15/0264 422/129 |
| 6,797,056 B2 | 9/2004 | David | |
| 6,808,934 B2 | 10/2004 | Mutz et al. | |
| 6,821,770 B1 | 11/2004 | Hogan | |
| 6,845,968 B2 | 1/2005 | Killeen et al. | |
| 6,852,851 B1 | 2/2005 | Tooke et al. | |
| 6,855,490 B2 | 2/2005 | Sompuram et al. | |
| 6,858,439 B1 | 2/2005 | Xu et al. | |
| 6,883,559 B2 | 4/2005 | Jeon et al. | |
| 6,893,612 B2 | 5/2005 | Kacian et al. | |
| 6,949,355 B2 | 9/2005 | Yamanishi et al. | |
| 6,949,575 B2 | 9/2005 | Barta et al. | |
| 6,994,749 B2 | 2/2006 | David | |
| 7,003,104 B2 | 2/2006 | Lee | |
| 7,015,041 B2 | 3/2006 | Santarsiero et al. | |
| 7,101,663 B2 | 9/2006 | Godfrey et al. | |
| 7,122,301 B2 | 10/2006 | Shvets et al. | |
| 7,122,640 B2 | 10/2006 | Gjerde et al. | |
| 7,126,626 B2 | 10/2006 | Sawahara et al. | |
| 7,129,091 B2 | 10/2006 | Ismagilov et al. | |
| 7,135,180 B2 | 11/2006 | Truong-Le | |
| 7,136,688 B2 | 11/2006 | Jung et al. | |
| 7,169,601 B1 | 1/2007 | Northrup et al. | |
| 7,235,216 B2 | 6/2007 | Kiselev et al. | |
| 7,244,961 B2 | 7/2007 | Jovanovic et al. | |
| 7,252,939 B2 | 8/2007 | Mori et al. | |
| 7,294,308 B2 | 11/2007 | Kacian et al. | |
| 7,294,466 B2 | 11/2007 | McMillan | |
| 7,294,503 B2 | 11/2007 | Quake et al. | |
| 7,297,485 B2 | 11/2007 | Bornarth et al. | |
| 7,306,672 B2 | 12/2007 | Hansen et al. | |
| 7,309,588 B2 | 12/2007 | Burg et al. | |
| 7,314,070 B2 | 1/2008 | Jeon et al. | |
| 7,319,003 B2 | 1/2008 | Cantor et al. | |
| 7,329,485 B2 | 2/2008 | Zlotnick | |
| 7,351,303 B2 | 4/2008 | Liu et al. | |
| 7,375,190 B2 | 5/2008 | Cheng et al. | |
| 7,413,712 B2 | 8/2008 | Liu et al. | |
| 7,465,562 B2 | 12/2008 | Wangh et al. | |
| 7,501,245 B2 | 3/2009 | Quake et al. | |
| 7,556,776 B2 | 7/2009 | Fraden et al. | |
| 7,595,871 B2 | 9/2009 | Weber | |
| 7,608,399 B2 | 10/2009 | Reed et al. | |
| 7,615,274 B2 | 11/2009 | Ehrfeld et al. | |
| 7,629,165 B2 | 12/2009 | Wyatt et al. | |
| 7,648,835 B2 | 1/2010 | Breidford et al. | |
| 7,655,129 B2 | 2/2010 | Blackburn et al. | |
| 7,683,035 B1 | 3/2010 | Erbacher et al. | |
| 7,767,447 B2 | 8/2010 | Breidenthal et al. | |
| 7,780,336 B2 | 8/2010 | Breidenthal et al. | |
| 7,790,865 B1 | 9/2010 | Heath et al. | |
| 7,846,333 B2 | 12/2010 | Pluester et al. | |
| 7,851,207 B1 | 12/2010 | Sagripanti | |
| 7,867,757 B2 | 1/2011 | Karlsen et al. | |
| 7,871,813 B2 | 1/2011 | Wyatt et al. | |
| 7,915,030 B2 | 3/2011 | Inoue et al. | |
| 7,939,018 B2 | 5/2011 | Bedingham et al. | |
| 7,939,249 B2 | 5/2011 | Parthasarathy et al. | |
| 7,955,504 B1 | 6/2011 | Jovanovic et al. | |
| 7,998,708 B2 | 8/2011 | Handique et al. | |
| 8,043,811 B2 | 10/2011 | Danks et al. | |
| 8,052,929 B2 | 11/2011 | Breidenthal et al. | |
| 8,057,758 B2 | 11/2011 | Bedingham et al. | |
| 8,097,222 B2 | 1/2012 | Scurati | |
| 8,137,554 B2 | 3/2012 | Jovanovic et al. | |
| 8,187,557 B2 | 5/2012 | Van Atta et al. | |
| 8,211,367 B2 | 7/2012 | Wyatt et al. | |
| 8,221,705 B2 | 7/2012 | Breidenthal et al. | |
| 8,222,023 B2 | 7/2012 | Battrell et al. | |
| 8,273,245 B2 | 9/2012 | Jovanovic et al. | |
| 8,323,900 B2 | 12/2012 | Handique et al. | |
| 8,362,219 B2 | 1/2013 | Gjerde et al. | |
| 8,415,103 B2 | 4/2013 | Handique | |
| 8,449,830 B2 | 5/2013 | Claussen et al. | |
| 8,470,586 B2 | 6/2013 | Wu et al. | |
| 8,480,976 B2 | 7/2013 | Breidenthal et al. | |
| 8,491,178 B2 | 7/2013 | Breidenthal et al. | |
| 8,574,833 B2 | 11/2013 | Jenison et al. | |
| 8,615,368 B2 | 12/2013 | Light, II et al. | |
| 8,637,250 B2 | 1/2014 | Jenison | |
| 8,784,745 B2 | 7/2014 | Nelson et al. | |

(56) References Cited

U.S. PATENT DOCUMENTS

| | | |
|---|---|---|
| 2001/0048900 A1 | 12/2001 | Bardell et al. |
| 2002/0008029 A1 | 1/2002 | Williams et al. |
| 2002/0012971 A1 | 1/2002 | Mehta |
| 2002/0017464 A1 | 2/2002 | Parce et al. |
| 2002/0022261 A1 | 2/2002 | Anderson et al. |
| 2002/0058332 A1 | 5/2002 | Quake et al. |
| 2002/0076825 A1 | 6/2002 | Cheng et al. |
| 2002/0125197 A1 | 9/2002 | Hager et al. |
| 2002/0147317 A1 | 10/2002 | Bentsen et al. |
| 2002/0155032 A1 | 10/2002 | Liu et al. |
| 2002/0172969 A1 | 11/2002 | Burns et al. |
| 2003/0022243 A1 | 1/2003 | Kondejewski et al. |
| 2003/0064414 A1 | 4/2003 | Benecky et al. |
| 2003/0190608 A1 | 10/2003 | Blackburn |
| 2003/0229376 A1 | 12/2003 | Sandhu |
| 2004/0005582 A1 | 1/2004 | Shipwash |
| 2004/0037813 A1 | 2/2004 | Simpson et al. |
| 2004/0072357 A1 | 4/2004 | Stiene et al. |
| 2004/0119070 A1* | 6/2004 | Roach et al. .................. 257/48 |
| 2004/0137458 A1 | 7/2004 | Archambault et al. |
| 2004/0181131 A1 | 9/2004 | Maynard et al. |
| 2004/0224419 A1 | 11/2004 | Zheng et al. |
| 2004/0228212 A1* | 11/2004 | de Goor et al. ............. 366/341 |
| 2004/0258571 A1 | 12/2004 | Lee et al. |
| 2005/0009582 A1 | 1/2005 | Vooi-Kia et al. |
| 2005/0019792 A1 | 1/2005 | McBride et al. |
| 2005/0087122 A1 | 4/2005 | Ismagliov et al. |
| 2005/0172476 A1 | 8/2005 | Stone et al. |
| 2005/0221339 A1 | 10/2005 | Griffiths et al. |
| 2006/0003439 A1 | 1/2006 | Ismagilov et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0163385 A1 | 7/2006 | Link et al. |
| 2006/0188911 A1 | 8/2006 | Otomo et al. |
| 2006/0195047 A1 | 8/2006 | Freeman et al. |
| 2007/0003442 A1 | 1/2007 | Link et al. |
| 2007/0014695 A1* | 1/2007 | Yue et al. .................... 422/100 |
| 2007/0015545 A1 | 1/2007 | Leifer et al. |
| 2007/0026439 A1 | 2/2007 | Faulstich et al. |
| 2007/0052781 A1 | 3/2007 | Fraden et al. |
| 2007/0077547 A1 | 4/2007 | Shvets et al. |
| 2007/0092914 A1 | 4/2007 | Griffiths et al. |
| 2007/0093894 A1 | 4/2007 | Darouiche |
| 2007/0134739 A1 | 6/2007 | Holmquist et al. |
| 2007/0172954 A1 | 7/2007 | Ismagilov et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2008/0003142 A1 | 1/2008 | Link et al. |
| 2008/0003693 A1 | 1/2008 | Torres |
| 2008/0014589 A1 | 1/2008 | Link et al. |
| 2008/0058039 A1 | 3/2008 | Lee et al. |
| 2008/0107565 A1 | 5/2008 | Vivienne et al. |
| 2008/0108063 A1 | 5/2008 | Lucero et al. |
| 2008/0129736 A1 | 6/2008 | Sun et al. |
| 2008/0166793 A1 | 7/2008 | Beer et al. |
| 2008/0213215 A1 | 9/2008 | Krishnan et al. |
| 2008/0293045 A1 | 11/2008 | Piepenburg et al. |
| 2009/0010804 A1 | 1/2009 | Withrow, III et al. |
| 2009/0021728 A1 | 1/2009 | Heinz et al. |
| 2009/0035847 A1 | 2/2009 | Cho et al. |
| 2009/0053719 A1* | 2/2009 | Lo et al. ......................... 435/6 |
| 2009/0057149 A1 | 3/2009 | Wegner et al. |
| 2009/0060797 A1 | 3/2009 | Mathies et al. |
| 2009/0062134 A1 | 3/2009 | Linton et al. |
| 2009/0068760 A1 | 3/2009 | Nelson et al. |
| 2009/0069194 A1 | 3/2009 | Ramakrishnan |
| 2009/0117620 A1 | 5/2009 | Fritchie et al. |
| 2009/0176280 A1* | 7/2009 | Hutchison, III et al. .... 435/91.2 |
| 2009/0197248 A1 | 8/2009 | Griffiths et al. |
| 2009/0215050 A1 | 8/2009 | Jenison |
| 2009/0221096 A1 | 9/2009 | Torres |
| 2009/0298191 A1 | 12/2009 | Whitesides et al. |
| 2010/0022414 A1 | 1/2010 | Link et al. |
| 2010/0137152 A1 | 6/2010 | Gorfinkel et al. |
| 2010/0304387 A1 | 12/2010 | Jenison et al. |
| 2010/0308051 A1 | 12/2010 | Weber |
| 2011/0166044 A1 | 7/2011 | Jones et al. |
| 2011/0297866 A1 | 12/2011 | Weber |
| 2011/0303306 A1 | 12/2011 | Weber |
| 2011/0318728 A1 | 12/2011 | Phan et al. |
| 2012/0028342 A1 | 2/2012 | Ismagilov et al. |
| 2012/0077188 A1 | 3/2012 | Nelson et al. |
| 2012/0329038 A1 | 12/2012 | Ismagilov et al. |
| 2013/0130226 A1 | 5/2013 | Lim et al. |
| 2013/0288348 A1 | 10/2013 | Breidenthal et al. |
| 2013/0331298 A1 | 12/2013 | Rea |
| 2014/0017730 A1 | 1/2014 | Hicke et al. |
| 2014/0038200 A1 | 2/2014 | Jenison et al. |
| 2014/0134619 A1 | 5/2014 | Jenison |
| 2014/0336064 A1 | 11/2014 | Ismagilov et al. |

FOREIGN PATENT DOCUMENTS

| | | |
|---|---|---|
| EP | 0816837 A1 | 1/1998 |
| EP | 1110084 B1 | 7/1999 |
| EP | 1036082 B1 | 5/2002 |
| EP | 0996547 B1 | 12/2002 |
| EP | 0808456 B1 | 5/2003 |
| EP | 0739240 B1 | 6/2004 |
| EP | 1287164 B1 | 10/2004 |
| EP | 1473084 A2 | 11/2004 |
| EP | 1080099 B1 | 2/2006 |
| EP | 1495119 B1 | 1/2007 |
| EP | 1641564 B1 | 10/2007 |
| EP | 1177318 B1 | 2/2008 |
| EP | 1173623 B1 | 6/2008 |
| EP | 1740722 B1 | 8/2008 |
| EP | 1382676 B1 | 5/2009 |
| EP | 1925678 B1 | 7/2009 |
| EP | 1380642 B1 | 3/2010 |
| EP | 1714134 B1 | 4/2010 |
| EP | 0875584 B1 | 9/2010 |
| EP | 1631685 B1 | 12/2010 |
| EP | 2305809 A2 | 4/2011 |
| EP | 1820552 B1 | 6/2011 |
| EP | 1679383 B1 | 7/2011 |
| EP | 1896180 B1 | 11/2011 |
| EP | 1630228 B1 | 1/2012 |
| EP | 2007905 B1 | 8/2012 |
| EP | 2016186 B1 | 1/2013 |
| EP | 1558934 B1 | 7/2013 |
| EP | 2276828 B1 | 7/2013 |
| GB | 2097692 A | 11/1982 |
| WO | WO 84/02000 A1 | 5/1984 |
| WO | WO 97/04297 A1 | 2/1997 |
| WO | WO 97/29508 A2 | 8/1997 |
| WO | WO 98/00231 A1 | 1/1998 |
| WO | WO 98/02237 A1 | 1/1998 |
| WO | WO 98/52691 A1 | 11/1998 |
| WO | WO 00/13014 | 3/2000 |
| WO | WO 00/21666 A1 | 4/2000 |
| WO | WO 01/12327 A1 | 2/2001 |
| WO | WO 01/77683 A1 | 10/2001 |
| WO | WO 02/12856 A1 | 2/2002 |
| WO | WO 02/23163 A1 | 3/2002 |
| WO | WO 02/25243 A1 | 3/2002 |
| WO | WO 03/044221 A1 | 5/2003 |
| WO | WO 2004/038363 A2 | 5/2004 |
| WO | WO 2005/010169 A2 | 2/2005 |
| WO | WO 2005/016529 A1 | 2/2005 |
| WO | WO 2006/088876 A2 | 8/2006 |
| WO | WO 2006/096571 A2 | 9/2006 |
| WO | WO 2006/101851 A2 | 9/2006 |
| WO | WO 2007/009082 A1 | 1/2007 |
| WO | WO 2007/021343 A2 | 2/2007 |
| WO | WO 2007/030501 A2 | 3/2007 |
| WO | WO-2007/044974 A2 | 4/2007 |
| WO | WO 2007/081385 A2 | 7/2007 |
| WO | WO 2007/081386 A2 | 7/2007 |
| WO | WO 2007/081387 A1 | 7/2007 |
| WO | WO 2007/089541 A2 | 8/2007 |
| WO | WO 2007/089777 A2 | 8/2007 |

(56) References Cited

FOREIGN PATENT DOCUMENTS

| | | |
|---|---|---|
| WO | WO 2007/133710 A2 | 11/2007 |
| WO | WO 2007/146923 | 12/2007 |
| WO | WO 2008/002267 A1 | 1/2008 |
| WO | WO 2008/043041 A1 | 4/2008 |
| WO | WO 2008/048673 A2 | 4/2008 |
| WO | WO 2008/063227 A2 | 5/2008 |
| WO | WO 2008/069884 A2 | 6/2008 |
| WO | WO 2008/079274 A1 | 7/2008 |
| WO | WO 2008/097559 A2 | 8/2008 |
| WO | WO 2008/147382 A1 | 12/2008 |
| WO | WO 2009/002849 A2 | 12/2008 |
| WO | WO 2009/012420 A1 | 1/2009 |
| WO | WO 2009/013683 A1 | 1/2009 |
| WO | WO 2009/015390 A2 | 1/2009 |
| WO | WO 2009/018348 A1 | 2/2009 |
| WO | WO 2009/048673 A2 | 4/2009 |
| WO | WO 2009/070640 | 6/2009 |
| WO | WO 2009/070742 | 6/2009 |
| WO | WO 2009/071078 A1 | 6/2009 |
| WO | WO 2009/105648 | 8/2009 |
| WO | WO 2009/149257 A1 | 12/2009 |
| WO | WO 2010/078420 | 7/2010 |
| WO | WO 2010/083795 A1 | 7/2010 |
| WO | WO 2010/094249 A1 | 8/2010 |
| WO | WO 2011/109762 | 9/2011 |
| WO | WO 2013/123238 | 8/2013 |

OTHER PUBLICATIONS

Benner et al., "Synthetic Biology", Nat. Rev. Genet., Jul. 2005, 6, No. 7, 533-543.

Blainey et al., "Digital MDA for enumeration of total nucleic acid contamination", Nucleic Acids Res., 2011, 39, e19.

Brouzes et al., "Droplet microfluidic technology for single-cell high-throughput screening", Proc. Natl. Acad. Sci., 2009, 106, 14195-14200.

Chelliserrykattil et al., "Development of a Quantitative Real-Time Transcription-Mediated Amplification Assay for Simultaneous Detection of Multiple Nucleic Acid Analytes", J Mol. Diagn. 2009, 11, 680.

Cheng et al., "Research needs and challenges in the development of HIV diagnostic and treatment monitoring tests for use in resource-limited settings", Curr. Opin., HIV AIDS, 2008, 3, 495-503.

Choi et al., "Programmable in situ amplification for multiplexed imaging of mRNA expression," Nature Biotechnol, 2010, 28, 1208-1212.

Compton, "Nucleic acid sequence-based amplification", Nature, 1991, 350, 91-92.

de Baar et al., "One-tube real-time isothermal amplification assay to identify and distinguish human immunodeficiency virus type 1 subtypes A, B, and C and circulating recombinant forms AE and AG", J. Clin. Microbial., 2001, 39, 1895-1902.

Dean et al., "Comprehensive human genome amplification using multiple displacement amplification", Proc. Natl. Acad. Sci., 2002, 99, 5261-5266.

Dimov et al., "Integrated microfluidic tmRNA purification and real-time NASBA device for molecular diagnostics", Lab on a Chip, 2008, 8, 2071-2078.

Dirks et al., "Triggered Amplification by Hybridization Chain Reaction." Proceedings of the National Academy of Sciences of the United States of America, 2004, 101, No. 43, 15275-15278.

Du et al., "SlipChip", Lab Chip, 2009, 9, 2286-2292.

Esch et al., "Detection of Viable Cryptosporidium parvum Using DNA-Modified Liposomes in a Microfluidic Chip", Anal. Chern., 2001, 73, 2952-2958.

Fan et al., "Detection of Aneuploidy with Digital Polymerase Chain Reaction", Anal. Chern., 2007, 79, 7576-7579.

Fang et al., "Loop-Mediated Isothermal Amplification Integrated on Microfluidic Chips for Point-of-Care Quantitative Detection of Pathogens", Anal. Chern., 2010, 82, 3002-3006.

Genot et al, "Remote Toehold: A Mechanism for Flexible Control of DNA Hybridization Kinetics," JACS, 2011, 133 (7), 2177-2182.

Gibson et al., "A Novel Method for Real Time Quantitative RT-PCR", Genome Res., 1996, 6, 995-1001.

Graugnard et al., "Kinetics of DNA and RNA Hybridization in Serum and Serum-SDS", Nanotechnology, IEEE Transactions, 2010, 9, No. 5, 603-609.

Heid et al., "Real Time Quantitative PCR", Genome Res., 1996, 6, 986-994.

Hellyer et al., "Strand Displacement amplification: a versatile tool for molecular diagnostics", Expert Rev. Mol. Diagn., 2004, 4, 251-261.

Hill et al., "Direct Detection of Microorganisms in Clinical Specimens Using the Gen-Probe Transcription Meidated Amplification System", Clin. Chern., 1995, 41, S107.

International Patent Application No. PCT/US2008/071374: International Search Report dated Aug. 31, 2009, 7 pages.

International Patent Application No. PCT/US2010/028316: International Search Report dated May 10, 2010, 1 page.

Jarvius et al., "Digital quantification using amplified single-molecule detection", Nat. Methods, 2006, 3, 725-727.

Kalinina et al., "Nanoliter scale PCR with TaqMan detection", J. Nucleic Acids Res., 1997, 25, 1999-2004.

Kiss et al., "High-Throughput Quantitative Polymerase Chain Reaction in Picoliter Droplets", Anal. Chern., 2008, 80, 8975-8981.

Kreutz et al., "Theoretical Design and Analysis of Multivolume Digital Assays with Wide Dynamic Range Validated Experimentally with Microfluidic Digital PCR", Anal. Chern., 2011 83, 8158-8168.

Leng et al., "Agarose droplet microfluidics for highly parallel and efficient single molecule emulsion PCR", Lab on a Chip, 2010,10, 2841-2843.

Li et al., "A New Class of Homogeneous Nucleic Acid Probes Based on Specific Displacement Hybridization", Nucleic Acids Research, 2002, 30, No. e5.

Li et al., "Rational, modular adaptation of enzyme-free DNA circuits to multiple detection methods", Nucl. Acids Res., 2011, 1-13.

Li et al., "Dead-End Filling of SlipChip Evaluated Theoretically and Experimentally as a Function of the Surface Chemistry and the Gap Size between the Plates for Lubricated and Dry SlipChips", Langmuir, 2010, 26, 12465-12471.

Li et al., "Multiparameter Screening on SlipChip Used for Nanoliter Protein Crystallization Combining Free Interface Diffusion and Microbatch Methods", J. Am. Chern. Soc., 2009, 132, 112-119.

Li et al., "Protein Crystallization Using Microfluidic Technologies Based on Valves, Droplets, and Slip Chip", Annu. Rev. Biophys., 2010, 39, 139-158.

Li et al., "User-Loaded SlipChip for Equipment-Free Multiplexed Nanoliter-Scale Experiments", JACS, 2010, 132, 106-111.

Li et al., "Using a Multijunction Microfluidic Device to Inject Substrate into an Array of Performed Plugs without Cross-Contamination: Comapring Theory and Experiments", Anal. Chern., 2007, 79, 2756-2761.

Liu et al., "SlipChip for Immunoassays in Nanoliter Volumes", Anal. Chern., 2010, 82, 3276-3282.

Liu et al., "Solving the "World-to-Chip" Interface Problem with a Microfluidic Matrix", Anal. Chern., 2003, 75, 4718-4723.

Livak et al., "Analysis of Relative Gene Expression Data Using Real-Time Quantitative PCR and the $2^{-\Delta\Delta C}T$ Method", 2001, 25, 402-408.

Lizardi et al., "Mutation detection and single-molecule counting using isothermal rolling-circle amplification", Nature Genet., 1998, 19, 225-232.

Lo et al., "Digital PCR for the molecular detection of fetal chromosomal aneuploidy", Proc. Natl. Acad. Sci., 2007, 104, 13116-13121.

Lutz et al., "Microfluidic lab-on-a-foil for nucleic acid analysis based on isothermal recombinase polymerase amplification (RPA)", Lab on a Chip, 2010, 10, 887-893.

Mackay et al., "Real-time PCR in virology", Nucleic Acids Res., 2002, 30, 1292-1305.

(56) References Cited

OTHER PUBLICATIONS

Mazutis et al., "Droplet-Based Microfluidic Systems for High-Throughput Single DNA Molecule Isothermal Amplification and Analysis", Anal. Chern., 2009, 81, 4813-4821.
Nacht et al., "Molecular characteristics of non-small cell lung cancer", Proc. Natl. Acad. Sci., 2001, 98, 15203-15208.
Notomi et al., "Loop-mediated isothermal amplification of DNA", Nucleic Acids Res., 2000, 28, 7 pages.
Ottesen et al., "Microfluidic Digital PCR Enables Multigene Analysis of Individual Environmental Bacteria", Science, 2006, 314, 1464-1467.
Piche et al., "Optimization of in Vitro Transcription and Full-Length cDNA Synthesis Using the T4 Bacteriophage Gene 32 Protein", J Biomol. Tech., 2005, 16, 239-247.
Picuri et al., "Universal Translators for Nucleic Acid Diagnosis" Journal of the American Chemical Society, 2009, 131, No. 26, 9368-9377.
Piepenburg et al., "DNA Detection Using Recombination Proteins", PLoS Bioi. 2006, 4, 1115-1121.
Preiser et al., "HIV-1 Viral Load Assays for Resource-Limited Settings: Clades Matter", PLoS Med., 2006, 3, e538.
Qian et al., "Scaling up Digital Circuit Computation with DNA Strand Displacement Cascades" Science, 2011, 332, No. 6034, 1196-1201.
Seelig et al., "Enzyme-Free Nucleic Acid Logic Circuits," Science, Dec. 8, 2006, 1585-1588.
Shamoo et al., "Crystal structure of a replication fork single-stranded DNA binding protein (T4 gp32) complexed to DNA", Nature, 1995, 376, 362-366.
Shen et al., "Digital Isothermal Quantification of Nucleic Acids via Simultaneous Chemical Initiation of Recombinase Polymerase Amplification Reactions on SlipChip", Analytical Chemistry, 2011, 83, 3533-3540.
Shen et al., "Digital PCR on a SlipChip", Lab on a Chip, 2010, 10, 2666-2672.
Shen et al., "Multiplexed Quantification of Nucleic Acids with Large Dynamic Range Using Multivolume Digital RT-PCR on a Rotational SlipChip Tested with HIV and Hepatitis C Viral Load", JACS, 2011, 133, 17705-17712.
Shen et al., "Nanoliter Multiplex PCR Arrays on a SlipChip", Analytical Chemistry, 2010, 82, 4606-4612.
Song et al., "A Microfluidic System for Controlling Reaction Networks in Time", Angew. Chern.-Int. Edit., 2003, 42, 768-772.
Sundberg et al., "Spinning Disk Platform for Microfluidic Digital Polymerase Chain Reaction", Anal. Chern., 2010, 82, 1546-1550.
Sykes et al., "Quantitation of Targets for PCR by Use of Limiting Dilution", Biotechniques, 1992, 13, 444-449.
Tewhey et al., "Microdroplet-based PCR enrichment for large-scale targeted sequencing", Nat. Biotechnol. 2009, 27, 1025-1031.
Thorsen et al., "Microfluidic Large-Scale Integration", Science, 2002, 298, 580-584.
Tsongalis et al., "Branched DNA Technology in Molecular Diagnostics" American journal of clinical pathology, 2006, 126, No. 3, 448-453.
UNAIDS, "UNAIDS/WH Report on the Global AIDS Epidemic", UNAIDS/WHO, 2008, 362 pages.
Van Ness et al., "Isothermal Reactions for the Amplification of Oligonucleotides" Proceedings of the Nationa Academy of Sciences, 2003, 100, No. 8, 4504-4509.
Vet et al., "Multiplex detection of four pathogenic retroviruses using molecular beacons", Proc. Natl. Acad. Sci., 1999, 96, 6394-6399.
Vincent et al., "Helicase-dependant isothermal DNA amplification", EMBO Rep., 2004, 5, 795-800.
Vogelstein et al., "Digiatl PCR", Proc. Natl. Acad. Sci., 1999, 96, 9236-9241.
Walker et al., "Strand displacement amplification—an isothermal, in vitro DNA amplification technique", Nucleic Acids Res., 1992, 20, 1691-1696.
Yin et al., "Programming Biomolecular Self-Assembly Pathways", Nature, 2008, 451, No. 7176, 318-322.
Zhang et al., "A DNA-Origami Chip Platform for Label-Free SNP Genotyping Using Toehold-Mediated Strand Displacement", Small, 2010, 6, No. 17, 1854-1858.
Zhang et al., "Control of DNA Strand Displacement Kinetics Using Toehold Exchange" Journal of the American Chemical Society, 2009, 131, No. 47, 17303-17314.
Zhang et al., "Engineering Entropy-Driven Reactions and Networks Catalyzed by DNA.", Science, 2007, 318, No. 5853, 1121-1125.
Zheng et al., "A Microfluidic Approach for Screening Submicroliter Volumes against Multiple Reagents by Using Performed Arrays of Nanoliter Plugs in a Three-Phase Liquid/Liquid/Gas Flow", Angew. Chern. Int. Ed., 2005, 44, 2520-2523.
U.S. Appl. No. 14/177,190, filed Feb. 10, 2014, Ismagilov et al.
U.S. Appl. No. 14/177,194, filed Feb. 10, 2014, Ismagilov et al.
Abhyankar, Vinay V. et al., "Spatiotemporal Micropatterning of Cells on Arbitrary Substrates", Anal. Chem., vol. 79, (2007), pp. 4066-4073.
Abrams, William R., et al., "Development of a Microfluidic Device for Detection of Pathogens in Oral Samples Using Upconverting Phoshor Technology (UPT)," Ann. N.Y. Acad. Sci. 1098: (2007), pp. 375-388.
Adamson, David N. et al., "Production of Arrays of Chemically Distinct Nanolitre Plugs via Repeated Splitting in Microfluidic Devices", Lab on a Chip, vol. 6, (2006), pp. 1178-1186.
Aharoni, Amir, et al., "High-Throughput Screening of Enzyme Libraries: Thiolactonases Evolved by Fluorescence-Activated Sorting of Single Cells in Emulsion Compartments," Chem. Biol., vol. 12, (2005), pp. 1281-1289.
Ajaev, Vladimir S., et al. "Steady Vapor Bubbles in Rectangular Microchannels", Journal of Colloid and Interface Science, vol. 240, (2001), pp. 259-271.
Ajaev, Vladimir S., et al. "Three-Dimensional Steady Vapor Bubbles in Rectangular Microchannels", Journal of Colloid and Interface Science, vol. 244, (2001), pp. 180-189.
Akselband, Y. et al., "Rapid Mycobacteria Drug Susceptibility Testing Using Gel Microdrop (GMD) Growth Assay and Flow Cytometry", J. Microbiol. Methods, vol. 62, (2005), pp. 181197.
Alberts, Bruce et al., "Chapter 22—Histology: The Lives and Deaths of Cells in Tissues", Molecular Biology of the Cell (Garland Publishing, 2002), pp. 1259-1312.
Alizadeh, Ash A. et al., "Genomic-Scale Gene Expression Profiling of Normal and Malignant Immune Cells", Current Opinion in Immunology, vol. 12, No. 2, (2000), pp. 219-225.
Alter,Orly et al., "Singular Value Decomposition for Genome-Wide Expression Data Processing and Modeling", PNAS (2000), vol. 97, No. 18, pp. 10101-10106.
Altreuter, David H. et al., "Combinatorial Biocatalysis: Taking the Lead From Nature", Current Opinion in Biotechnology vol. 10, No. 2, (1999), pp. 130-136.
Anderson, Megan J. et al., "Phase Knowledge Enables Rational Screens for Protein Crystallization," PNAS, vol. 103, No. 45, (2006) pp. 16746-16751.
Andersson, Helene et al., "Microfluidic Devices for Cellomics: A Review," Sensors and Actuators B—Chemical 92, (2003), pp. 315-325.
Androulakis,I.P. et al., "Analysis of Time-Series Gene Expression Data: Methods, Challenges, and Opportunities,", Annual Review of Biomedical Engineering, vol. 9, (2007), pp. 205-228.
Armstrong, Gavin, "Microfluidics: Introducing the Chemstrode," *Nature* Chemistry, Nov. 14, 2008.
Arrizon, Victor et al., "Talbot Array Illuminators with Liquid Crystal Displays," Opt. Eng., vol. 37, No. 1, (1997), pp. 189-197.
Aryan, Ehsan et al., "A Novel and More Sensitive Loop-Mediated Isothermal Amplification Assay Targeting IS6110 for Detection of *Mycobacterium tuberculosis* Complex," Microbiol Research vol. 165, (2010), pp. 211-220.
Atencia, Javier, et al. "Controlled Microfluidic Interfaces", Nature, 2005, vol. 437, No. 29, pp. 648-655.
Baker, Carolyn N., et al., "Evaluation of alamar Colorimetric Broth Microdilution Susceptibility Testing Method for Staphylococci and Enterococci," J. Clin. Microbiol., vol. 34, (1996), pp. 2654-2659.

(56) References Cited

OTHER PUBLICATIONS

Balakrishnan, Pachamuthu, et al., "Low-Cost Monitoring of HIV Infected Individuals on Highly Active Antiretroviral Therapy (HAART) in Developing Countries", vol. 121, (2005), pp. 345355.

Balasubramanian, Priya et al., "Confocal Images of Circulating Tumor Cells Obtained Using a Methodology and Technology That Removes Normal Cells," Molecular Pharmaceutics, vol. 6, No. 5, (2009) pp. 1402-1408.

Balslev, Daniela et al., "Cluster Analysis of Activity-Time Series in Motor Learning," Human Brain Mapping, vol. 15, No. 3, (2002), pp. 135-145.

Bang, Hyunwoo et al., "Serial Dilution Microchip for Cytotoxicity Test," Journal of Micromechanics and Microengineering, vol. 14, (2004), pp. 1165-1170.

Bange, Adam et al., Microfluidic Immunosensor Systems, Biosensors and Bioelectronics, vol. 20, (2005), pp. 2488-2503.

Barbieri, Laura et al., "Water Wetting Transition parameters of Perfluorinated Substrates with Periodically Distributed Flat-top Microscale Obstacles," Langmuir, vol. 23, (2007), pp. 17231734.

Baret, Jean-Christophe et al., "Fluorescence-Activated Droplet Sorting (FADS): Efficient Microfluidic Cell Sorting based on Enzymatic Activity," Lab Chip, vol. 9, (2009), pp. 1850-1858.

Bar-Joseph, Ziv "Analyzing Time Series Gene Expression Data," Bioinformatics, vol. 20, No. 16 (2004), pp. 2493-2503.

Bar-Nahum, Itsik et al., "Mild, Aqueous, Aerobic, Catalytic oxidation of Methane to Methanol and Acetaldehyde Catalized by a Supported Bipyrimidinylplatinum-Polyoxometalate Hybrid Compound," J. Am. Chem. Soc., vol. 126, (2004), pp. 10236-10237.

Beard, Daniel A. et al., "Dispersion of a Solute in a Microfluidic Channel," Journal of Applied Physics, vol. 89, No. 8, (2001), pp. 4667-4669.

Becker, Frederick F. et al. "Separation of Human Breast-Cancer Cells from Blood by Differential Dielectric Affinity," Proc. Nat'l. Acad. of Sci., vol. 92, (1995) pp. 860-864.

Beebe, David J. et al., "Physics and Applications of Microfluidics in Biology," Rev. Biomed. Eng. vol. 4 (2002) pp. 261-286.

Beer, Reginald N. et al. "On-Chip, Real-Time, Single-Copy Polymerase Chain Reaction in Picoliter Droplets", Anal. Chem., 2007, v. 79, pp. 8471-8475.

Behrens, Heidi L. et al., "Combining Microdialysis, NanoLC-MS, and MalDI-TOF/TOF to Detect Neuropeptides Secreted in the Crab, Cancer Borealis," Analytical Chemistry, vol. 80, No. 18, (2008), pp. 6949-6958.

Beliaeff, Benoit et al., "The Most "Probable Number" Estimate and its Confidence Limits," Water Res. vol. 27, No. 5, (1993), pp. 799-805.

Bergens, Steven H. et al., "A Redox Fuel Cell That Operates with Methane as Fuel at 120 Degrees C," Science, vol. 265, (1994), pp. 1418-1420.

Berger, Rachel Pardes et al., "Multiplex Assessment of Serum Biomarker Concentrations in Well-Appearing Children With Inflicted Traumatic Brain Injury" Pediatric Research, vol. 65, No. 1, pp. 97-102.

Berger, Rachel Pardes, et al., "Urinary S1008 Concentrations are Increased After Brain Injury in Children: A Preliminary Study," Pediatric Critical Care Medicine, vol. 7, No. 6, (2006), pp. 557-561.

Bergh, Sam et al., "Combinatorial Heterogeneous Catalysis: Oxidative Dehydrogenation of Ethane to Ethylene, Selective Oxidation of Ethane to Acetic Acid, and Selective Ammoxidation of propane to Acrylonitrile,", Topics in Catalysis, vol. 23, Nos. 1-4, pp. 65-79.

Bergman, Robert G. et al., "Computational Study of Methane Activation by TpRe(CO)2 and CpRe(CO)2 wit ha Steroelectronic Comparison of Cyclopentadienyl and Scorpianate Ligands," Organometallics, vol. 22,(2008), pp. 2331-2337.

Berthier, Erwin et al., "Managing Evaporation for More Robust Microscale Assays part 2. Characterization of convection and Diffusion for Cell Biology," Lab Chip, vol. 8, (2008), pp. 860-864.

Bhat, Somanath et al., "Single Molecule Detection in Nanofluidic Digital Array Enables Accurate Measurement of DNA Copy Number," Anal. Bioanal. Chem., vol. 394, (2009), pp. 457-467.

Biswal, Sibani Lisa et al., "Micromixing with Linked Chains of Paramagnetic Particles," Analytical Chemistry, vol. 76, No. 21, (2004) pp. 6448-6455.

Blicharz,Timothy M. et al., "Fiber-Optic Microsphere-Based Antibody Array for the Analysis of Inflammatory Cytokines in Saliva" Analytical Chemistry, vol. 81, No. 6, (2009) pp. 2106-2114.

Blyth, Brian J. et al, "Validation of Serum Markers for Blood-Brain Barrier Disruption in Traumatic Brain Injury" Journal of Neurotrauma, vol. 26, (2009), pp. 1497-1507.

Boccazzi, Paolo et al., "Gene Expression Analysis of *Escherichia coli* Grown in Miniaturized Bioreactor Platforms for High-Throughput Analysis of Growth and Genomic Data,", App. Microbio. Biotech., vol. 68, (2005), pp. 518-532.

Boedicker,James Q. et al., "Detecting Bacteria and Determining Their Susceptibility to Antibiotics by Stochastic Confinement in Nanoliter Droplets Using Plug-Based Microfluidics," Lab Chip vol. 8, (2008), pp. 1265-1272.

Boom, R. et al., "Rapid and Simple Method for Purification of Nucleic Acids," Journal of Clinical Microbiology, vol. 28, (1990), pp. 495-503.

Boukellal, Hakim et al., "Simple, Robust Storage of Drops and Fluids in a Microfluidic Device,". Lab Chip, vol. 9, (2009), pp. 331-338.

Bourne, James A. "Intracerebral Microdialysis: 30 Years as a Tool for the Neuroscientist," Clinical and Experimental Pharmacology and Physiology, vol. 30, (2003), pp. 16-24.

Brambilla, Don et al., "Multicenter Evaluation of Use of Dried Blood and Plasma Spot Specimens in Quantitative Assays for Human Immunodeficiency Virus RNA: Measurement, Precision, and RNA Stability," Journal of Clinical Microbiology, vol. 41, No. 5, (2003), pp. 1888-1893.

Braslaysky, Ido et al., "Objective-Type Dark-Field Illumination for Scattering from Microbeads" Applied Optics, vol. 40, No. 31, (2001), pp. 5650-5657.

Bringer, Michelle R. et al., "Microfluidic Systems for Chemical Kinetics that Rely on Chaotic Mixing in Droplets," Phil. Trans. R. Soc. Lond. A vol. 362, (2004), pp. 1087-1104.

Bronzeau, Sandrine et al., "Simultaneous Bioassays in a Microfluidic Channel on Plugs of Different Magnetic Particles", Analytica Chimica Acta, vol. 609 (2008), pp. 105-112.

Brown, Michael P.S. et al., "Knowledge-Based Analysis of Microarray Gene Expression Data by Using Support Vector Machines," PNAS, vol. 97, No. 1, (2000), pp. 262-267.

Bruls, D.M. et al., Rapid Integrated Biosensor for Multiplexed Immunoassays Based on Actuated Magnetic Nanoparticles, Lab Chip, vol. 9, (2009), pp. 3504-3510.

Burns, Mark A. et al. "Microfabricated structures for integrated DNA analysis", Proc. Natl. Acad. Sci. USA, May 1996, vol. 93, pp. 5556-5561.

Cady, Nathaniel C. et al., A Microchip-Based DNA Purification and Real-Time PCR Biosensor for Bacterial Detection, Sensors, Proceedings of IEEE 24-27, vol. 3, (2004), pp. 1191-1194.

Calmy, alexandra et al., "HIV Viral Load Monitoring in Resource-Limited Regions: Optional or Necessary?" CID, vol. 44, (2007), pp. 128-134.

Carpenter, John F. et al., "Long-Term Storage of Proteins," Current Protocols in Protein Science, Unit 4.6.1 Supplement 27, (2002), 6p.

Carrette, Odile et al., "State-of-the-Art Two-Dimensional Gel Electrophoresis: A Key Tool of Proteomics Research," Nature Protocols, vol. 1, No. 2 (2006), pp. 812-823.

Cellar, Nicholas A. et al., "Microfluidic Chip for Low-Flow Push-Pull Perfusion Sampling in Vivo with On-Line Analysis of Amino Acids," Analytical Chemistry, vol. 77, No. 21, (2005), pp. 7067-7073.

Cernak, Ibolja "Animal Models of Head Trauma," NeuroRx Journal of the American Society for Experimental NeuroTherapeutics, vol. 2, (2005), pp. 410-422.

Chabert, Max et al., "Microfluidic High-Throughput Encapsulation and Hydrodynamic Self-Sorting of Single Cells," PNAS, vol. 105, No. 9, (2008), pp. 3191-3196.

Charbonniere, Loie J. et al., "Lanthanide Complexes and Quantum Dots: A Bright Wedding for Resonance Energy Transfer," European Journal of Inorganic Chemistry, (2008), pp. 32413251.

(56) References Cited

OTHER PUBLICATIONS

Chase, et al., Stimulus-Induced Release of Substances from Olfactory Bulb Using Push-Pull Cannula. Nature, vol. 217 (5127) (1968), pp. 466.
Chayen, Naomi E. "Comparative Studies of Protein Crystallization by Vapour-Diffusion and Microbatch Techniques," Acta Crystallogr. D54, (1998) pp. 8-15.
Chayen, Naomi E. "Turning Protein Crystallization from an Art into a Science," Current Opinion in Structural Biology, vol. 14, (2004), pp. 577-583.
Chayen, Naomi E. A Novel Technique to Control the Rate of Vapour Diffusion, Giving Larger Protein Crystals, J. Appl. Crystallogr., vol. 30, (1997), pp. 198-202.
Chayen, Naomi E. et al., "Protein Crystallization: From Purified Protein to Diffraction-Quality Crystal," Nature Methods, vol. 5, No. 2, (2008), pp. 147-153.
Chayen, Naomi E., "Crystallization with oils: a new dimension in macromolecular crystal growth," Journal of Crystal Growth, 1999, vol. 196, pp. 434-441.
Chen, Chihchen et al., "Microfluidic Isolation and Transcriptome Analysis of Serum Microvesicles," Lab on a Chip, vol. 10, (2010), pp. 505-511.
Chen, Delai L. et al., "Microfluidic Cartridges Preloaded with Nanoliter Plugs of Reagents: An alternative to 96-Well Plates for Screening," Current Opinion in Chemical Biology, vol. 10, No. 3, (2006), pp. 226-231.
Chen, Delai L. et al., "The Chemistrode: A Droplet-Based Microfluidic Device for Stimulation and Recording with High Temporal, Spatial, and Chemical Resolution," PNAS, vol. 105, No. 44, (2008), pp. 16843-16848.
Chen, Delai L. et al., "Using Microfluidics to Observe the Effect of Mixing on Nucleation of Protein Crystals,", J. Am. Chem. Soc., vol. 127, (2005), pp. 9672-9673.
Chen, Delai L. et al., "Using Three-Phase Flow of Immiscible Liquids to Prevent Coalescence of Droplets in Microfluidic Channels: Criteria to Identify the Third Liquid and Validation with Protein Crystallization" Langmuir, vol. 23, No. 4, (2007), pp. 2255-2260.
Chen, Delai L. et al., "Using TIRF Microscopy to Quantify and Confirm Efficient Mass Transfer at the Substrate Surface of the Chemistrode,", New Journal of Physics, vol. 11, (2009), 075017, (9pp).
Chen, Grace D. et al., "Concentration and Purification of Human Immunodeficiency Virus Type 1 Virions by Microfluidic Separation of Superparamagnetic Nanoparticles,", Analytical Chemistry, vol. 82, No. 2, (2010), pp. 723-728.
Chen, Zuliang, et al., "Separation of Chromium (111) and Chromium (VI) by Capillary Electrophoresis using 2,6-Pyridinedicarboxylic Acid as a Pre-Column Complexation Agent," Journal of Chromatography A, vol. 927, (2001), pp. 219-227.
Cheng, Ben et al., "Research Needs and Challenges in the Development of HIV Diagnostic and Treatment Monitoring Tests for Use in Resource-Limited Settings,", Current Opinion in HIV and AIDS, vol. 3, (2008), pp. 495-503.
Chiu , Daniel T. et al., "Chemical Transformations in Individual Ultrasmall Biomimetic Containers," Science, vol. 283, (1999), pp. 1892-1895.
Chiu, Daniel T. et al., Droplets for Ultrasmall-Volume Analysis, Analytical Chemistry, vol. 81, No. 13, (2009) pp. 5111-5118.
Chu, Kuan-Lun et al., "Nanoporous Silicon Membrane Electrode Assembly for On-Chip Micro Fuel Cell Application," Journal of Microelectromechanical Systems, vol. 15, No. 3, (2006), pp. 671-677.
Chung, Bong Geun et al., "Human Neural Stem Cell Growth and Differentiation in a Gradient-Generating Mcirofluidic Device," Lab Chip, vol. 5, (2005), pp. 401-406.
Chung, Su Eun et al., "Optofluidic Encapsulation and Manipulation of Silicon Microchips Using Image Processing Based Optofluidic Maskless Lithography and Railed Microfluidics," Lab Chip, vol. 9, (2009) pp. 2845-2850.

Clausell-Tormos, Jenifer et al., "Droplet-Based Microfluidic Platforms for the Encapsulation and Screening of Mammalian Cells and Multicellular Organisms," Chemistry & Biology, vol. 15, (2008), pp. 427-437.
Clopper, C.J. et al., "The Use of Confidence or Fiducial Limis Illustrated in the Case of the Binomial," Biometrika vol. 26, No. 4, (1934), pp. 404-413.
Cochran, William G. "Estimation of Bacterial Densities by Means of the Most Probable Number,", Biometrics, vol. 6, (1950), pp. 105-116.
Cohen, Aina E. "An Automated system to Mount Cryo-Cooled Protein Crystals on a Synchrotron Beamline, Using Compact Sample Cassettes and a Small-Scale Robot," J. of Appl. Crystallogr. , vol. 35, (2002), pp. 720-726.
Cohen, Jon "The Marketplace of HIV/a1D$" Science, New Series, vol. 272, No. 5270 (1996), pp. 1880-1881.
Cohen, Michael H. et al., "Microfabrication of Silicon-Based Nanoporous Particulates for Medical Applications," Biomedical Microdevices, vol. 5, No. 3, (2003), pp. 253-259.
Collins, Francis S. "*Opportunities for Research and NIH*," Science, vol. 327, (2010) pp. 36-37.
Cookson, P. et al., "A Simple Spectrophotometric Method for the Quantification of Residual Haemoglobin in Platelet Concentrates," Vox Sanguinis, vol. 87, (2004), pp. 264-271.
Cooper, Joshua D. et al., "Evaluation of an Osmotic Pump for Microdialysis Sampling in an Awake and Untethered Rat," Journal of Neuroscience Methods, vol. 160 (2007), pp. 269-275.
Corma, A. et al., "Discovery of New Paraffin Isomerization Catalysts Based on So42-/Zr02 and Wox/Zr02 Applying Combinatorial Techniques," Catalysis Today, vol. 81, (2003), pp. 495-506.
Crowe, Suzanne et al., "Monitoring of Human Immunodeficiency Virus Infection in Resource-Constrained Countries," CID, vol. 37, Suppl 1, (2003) pp. S25-S35.
Crowley, Timothy A. et al., "Isolation of Plasma From Whole Blood Using Planar Microfilters for Lab-on-a-Chip Applications," Lab Chip, vol. 5, (2005), pp. 922-929.
Curtis, Kelly A. et al., "Rapid Detection of HIV-1 by Reverse-Transcription, Loop-Mediated Isothermal Amplification (RT-LAMP)" Journal of Virological Methods, vol. 151, (2008), pp. 264-270.
Dai, Jinhua et al., "Electrokinetic Trapping and Concentration Enrichment of DNA in a Microfluidic Channel," Journal of the American Chemical Society, vol. 125, (2003), pp. 13026-13027.
Danna, Erika A. et al., "Transcending the Biomarker Mindset: Deciphering Disease Mechanisms at the Single Cell Level," Curr. Opin. Chem. Biol., vol. 10, (2006), pp. 20-27.
De Man, J.C. et al., "MPN Tables, Corrected," Eur. J. Appl. Microbiol. Biotech. vol. 17, No. 5 (1983), pp. 301-305.
Dear, Paul H. et al., "Happy Mapping: Linkage Mapping Using a Physical Analogue of Meiosis," Nucleic Acids Research, vol. 21, No. 1, (1993), pp. 13-20.
de-Bashan, Luz E. et al., "Removal of ammonium and phosphorus ions from synthetic wastewater by the microalgae Chlorella vulgaris coimmobilized in alginate beads with the microalgae growth-promoting bacterium Azospirillum brasilense," 2002, vol. 36, pp. 29412948.
DeFina, Philip et al., "The New Neuroscience Frontier: Promoting Neuroplasticity and Brain Repair in Traumatic Brain Injury," The Clinical Neuropsychologist, vol. 23, No. 8, (2009), pp. 1391-1399.
deJong, J. B. et al., "New Replication Technique for the Fabrication of Thin Polymeric Microfluidic Devices with Tunable Porosity," Lab Chip—Miniaturisation for Chemistry and Biology, vol. 5, No. 11, (2005), pp. 1240-1247.
Delamarche, Emmanuel et al., Microfluidics for Processing Surfaces and Miniaturizing Biological Assays, Adv. Mater. vol. 17, (2005) pp. 2911-2933.
DeLellis, et al., "The Neurometabolic Cascade and Implications of mTBI: Mitigating Risk to the SOF Community," Journal of Special Operations Medicine: A Peer Reviewed Journal for SOF Medical Professionals, vol. 9, No. 4, (2009), pp. 36-42.
deMello, Andrew J. et al., "Control and Detection of Chemical Reactions in Microfluidic Systems," Nature 2006, vol. 442, pp. 394-402.

(56) References Cited

OTHER PUBLICATIONS

Dequeant, Mary-Lee et al., "A Complex Oscillating Network of Signaling Genes Underlies the Mouse Segmentation Clock," Science, vol. 314, (2006) p. 1595-1598.
Desai, Tejal A. et al., "Nanoporous Anti-Fouling Silicon Membranes for Biosensor Applications" Biosensors & Bioelectronics, vol. 15, (2000), pp. 453.462.
Dharmasiri, Udara et al., "Highly Efficient Capture and Enumeration of Low Abundance Prostate Cancer Cells Using Prostate-Specific Membrane Antigen Aptamers Immobilized to a Polymeric Microfluidic Device" Electrophoresis, vol. 30, (2009), pp. 3289-3300.
Dhopeshwarkar Rahul et al., "Transient Effects on Microchannel Electrokinetic Filtering with an Ion-Permselective Membrane," Analytical Chemistry, vol. 80, (2008), pp. 1039-1048.
Dhopeshwarkar, Rahul et al., "Electrokinetic Concentration Enrichment Within a Microfluidic Device Using a Hydrogel Microplug," Lab Chip, vol. 5, (2005), pp. 1148-1154.
Dhouib, Kaouthar et al., "Microfluidic Chips for the Crystallization of Biomacromolecules by Counter-Diffusion and On-Chip Crystal X-ray Analysis," Lab Chip, vol. 9, (2009), pp. 14121421.
Di Carlo, Dino et al., "Dynamic Single Cell Culture Array". Lab Chip, vol. 6, (2006), pp. 1445-1449.
Di Giusto, Daniel A. et al., "Proximity Extension of Circular DNA Aptamers with Real-Time Protein Detection," Nucleic Acids Research, vol. 33, No. 6, (2005), pp. 33-64.
Diercks, alan H. et al., A Microfluidic Device for Multiplexed Protein Detection in Nano-Liter Volumes, Anal. Biochem., vol. 386, (2009), pp. 30-35.
Dimov, Ivan K. et al., "Integrated Microfluidic tmRNA Purification and Real-Time NASBA Device for Molecular Diagnostics," Lab Chip, vol. 8, (2008), pp. 2071-2078.
Dittrich, Petra S. et al., "Lab-on-a-Chip: Miocrofluidics in Drug Discovery," Nat. Rev., vol. 5, (2006), pp. 210-218.
Dodge, Arash et al., "Electrokinetically Driven Microfluidic Chips with Surface-Modified Chambers for Heterogeneous Immunoassays," Anal. Chem., vol. 73, No. 14, (2001), pp. 3400-3409.
Dong, Yongzhi et al., "Heterogeneous Immunosensing Using Antigen and Antibody Monolayers on Gold Surfaces with Electrochemical and Scanning Probe Detection," Anal. Chem., vol. 72, No. 11, (2000), pp. 2371-2376.
Douglas-Jones, Anthony G. et al., "Molecular Assessment of Sentinel Lymph Node in Breast Cancer Management", Histopathology, No. 55, (2009), pp. 107-113.
Drosten, Christian et al., "Ultrasensitive Monitoring of HIV-I Viral Load by a Low-Cost Real-Time Reverse Transcription-PCR Assay with Internal Control for the 5 ' Long Terminal Repeat Domain," Clin Chem. vol. 52, (2006), pp. 1258-1266.
Du, Wen-Bin et al., "High-Throughput Nanoliter Sample Introduction Microfluidic Chip-Based Flow Injection Analysis System with Gravity-Driven Flows," Analytical Chemistry, vol. 77, No. 5, (2005), p. 1330.
Du, Wenbin et al., "SlipChip", Lab Chip, vol. 9, (2009), pp. 2286-2292.
Dube, Simant et al., "Mathmatical Analysis of Copy Number Variation in a DNA Sample Using Digital PCR on a Nanofluidic Device," PLoS One, vol. 3, No. 8, (2008), p. e2876.
Duffy, David C. et al., "Rapid Prototyping of Microfluidic systems in Poly(dimethylsiloxane)," Anal. Chem., vol. 70, No. 23, (1998), pp. 4974-4984.
Durbin, S.D. et al., "Protein Crystallization," Annu. Rev. Phys. Chem. vol. 47, (1996), pp. 171204.
Edd, Jon F. et al., "Nucleation and Solidification in Static Arrays of Monodisperse Drops," Lab Chip, vol. 9, (2009), pp. 1859-1865.
Eddaoudi, Mohamed et al., "Modular chemistry: Secondary Building Units as a Basis for the Design of Highly Porous and Robust Metal-organic Carboxylate Frameworks," Acc. Chem. Res., vol. 34, (2001), pp. 319-330.
Eisen, Michael B. et al., "Cluster Analysis and Display of Genome-Wide Expression Patterns," Proc. Natl. Acad. Sci., vol. 95, (1998), pp. 14863-14868.
Ekstrand, D. Henric et al., "A Sensitive Assay for the Quantification of Reverse Transcriptase Activity Based on the Use of Carrier-Bound Template and Non-Radioactive-Product Detection, with Special Reference to Human-Immunodeficiency-Virus Isolation," Biotechnol. Appl. Biochem. vol. 23, (1996), pp. 95-105.
El-ali, Jamil, et al., "Cells on Chips," Nature, vol. 442, (2006,) pp. 403-411.
Emamzadah, Soheila et al., "Cyclic Olefin Homopolymer-Based Microfluidics for Protein Crystallization and In Situ X-Ray Diffraction," Acta Crystallogr. vol. D65, (2009), pp. 913-920.
Emsley, Paul, et al., "Coot: Model-Building Tools for Molecular Graphics," Sect. D—Biol. Crystallogr., vol. D60, (2004), pp. 2126-2132.
Eon-Duval, alex et al., "Purification of Pharmaceutical-Grade Plasmid DNA by Anion-Exchange Chromatography in an RNase-Free Process," J. Chromatogr., vol. 804 (2004), pp. 327-335.
Epstein, Jason R. et al., "Fluorescence-Based Nucleic Acid Detection and Microarrays," Anal. Chim Acta, vol. 469 (2002) pp. 3-36.
Ernst, Jason et al., "Clustering Short Time Series Gene Expression Data," Bioinformatics, vol. 21 Suppl. 1 (2005), pp. 159-168.
Fan, alice C. et al., "Nanofluidic Proteomic Assay for Serial Analysis of Oncoprotein Activation in Clinical Specimens," Nature Medicine, vol. 15, No. 5, (2009), pp. 566-571.
Fan, Christina et al., "Digital PCR Enables Rapid Prenatal Diagnosis of Fetal Aneuploidy," Am. J. Obstet. Gynecol., (2008), pp. 199.
Fan, H. Christina et al., "Microfluidic Digital PCR Enables Rapid Prenatal Diagnosis of Fetal Aneuploidy," American Journal of Obstetrics & Gynecology, (2009), pp. 543.e1-543.e7.
Fan, Rong et al. "Integrated Barcode Chips for Rapid, Multiplexed Analysis of Proteins in Microliter Quantities of Blood," Nature Biotechnology, vol. 26, No. 12 (2008), pp. 373-1378.
Fekl, Ulrich et al., "Homogeneous Hydrocarbon C—H Bond Activiation and Functionalization with Platinum," Adv. Inorg. Chem., vol. 54, (2003), pp. 259-320.
Fidler, Isaiah J. et al., "The Pathogenesis of Cancer Metastasis: The 'Seed and Soil' Hypothesis Revisited," Nature Reviews Cancer, vol. 3, (2003) pp. 453-458.
Filkov, Vladimir et al., "Analysis Techniques for Microarray Time-Series Data" Journal of Computational Biology, vol. 9, No. 2, (2002), pp. 317-330.
Fiscus, et al. "HIV-1 Viral Load Assays for Resource-Limited Settings", PLoS Medicine, vol. 3, No. 10 (2007), pp. 1743-1750.
Franzblau, Scott G. et al., "Rapid Low-Technology MIC Determination with Clinical *Mycobacterium tuberculosis* Isolates by Using the Microplate alamar Blue Assay," J. Clin. Microbiol., vol. 36, No. 2 (1998), pp. 362-366.
Fu, Elain et al., "Modeling of a Competitive Microfluidic Heterogeneous Immunoassay: Sensitivity of the Assay Response to Varying System Parameters," Anal. Chem., vol. 81, (2009) pp. 3407-3413.
Gambi, Cecilia M.C. et al., "Dynamic percolation in fluorinated water-in-oil microemulsions", Physical Review E. Oct. 1997, v 56, No. 4, pp. 4356-4363.
Gao, Jian et al., "Integration of Single Cell Injection, Cell Lysis, Separation and Detection of Intracellular Constituents on a Microfluidic Chip," Lab Chip, vol. 4, (2004), pp. 47-52.
Garcia-Ruiz, et al., "Investigations on Protein Crystal Growth by the Gel Acupuncture Method," Acta Cryst., D50, (1994), pp. 484-490.
Garcia-Ruiz, J.M. et al., "Investigation on protein crystal growth by the gel acupuncture method," Acta. Cryst,, 1994, vol. D50, pp. 484-490.
Garcia-Ruiz, Juan Ma. et al., "A supersaturation wave of protein crystallization", J. Crystal Growth, 2001, vol. 232, pp. 149-155.
Garthright, Wallace E. et al., "Confidence Intervals for Microbial Density Using Serial Dilutions with MPN Estimates," Biom. J., vol. 38, No. 4, (1996), pp. 489-505.
Gascoyne, Peter R.C. et al., "Isolation of Rare Cells From Cell Mixtures by Dielectrophoresis," Electrophoresis, vol. 30, (2009), pp. 1388-1398.

(56) References Cited

OTHER PUBLICATIONS

Geletii, Yu V. et al., "Catalytic-Oxidation of alkanes by Molecular Oxidation, Oxidation of Methane in the Presence of Platinum Salts and Heteropoly Acids", Kinet. Catal., vol. 24, No. 2, (1983), pp. 413-416.
Gerdts, Cory J. et al., "A Synthetic Reaction Network: Chemical Amplification Using Nonequilibrium Autocatalytic Reactions Coupled in Time," J. Am. Chem. Soc., vol. 126, (2004), pp. 6327-6331.
Gerdts, Cory J. et al., "The Plug-Based Nanovolume Microcapillary Protein Crystallization System (MPCS)," vol. D64 (2008), pp. 1116-1122.
Gerdts, Cory J. et al., "Time-Controlled Microfluidic Seeding in nL-Volume Droplets to Separate Nucleation and Growth Stages of Protein Crystallization," vol. 45, (2006), pp. 81568160.
Goldman, Ellen R. et al., "Luminescent Quantum Dots Immunoassays," Anal Bioanal Chem., vol. 384 (2006), pp. 560-563.
Goodall, Jennifer L. et al., "Operation of Mixed-Culture Immobilized Cell Reactors for the Metabolism of Meta- and- Para-Nitrobenzoate by *Comamonas* Sp. JS46 and *Comamonas* Sp. J547," 1998, John Wiley & Sons, Inc., pp. 21-27.
Gorris, Hans H. et al., "Mechanistic Aspects of Horseradish Peroxidase Elucidated through Single-Molecule Studies" J. Am. Chem. Soc. vol. 131, (2009), pp. 6277-6282.
Gorris, Hans H. et al., "Stochastic Inhibitor Release and Binding from Single-Enzyme Molecules," PNAS, vol. 104, No. 45, (2007), pp. 17680-17685.
Gratton, Stephanie E.A. et al., "Nanofabricated Particles for Engineered Drug Therapies: A Preliminary Biodistribution Study of PRINT Nanoparticles," ScienceDirect Journal of Controlled Release, vol. 121 (2007), pp. 10-18.
Greengrass, Vicki et al., "Assessment of the Low-Cost Cavidi ExaVir Load Assay for Monitoring HIV Viral Load in Pediatric and Adult Patients," Acquir Immune Defic Syndr, vol. 52, No. 3, (2009), pp. 387-390.
Griffiths, Andrew D. et al., "Man-Made Enzymes—From Design to In Vitro Compartmentalisation," Curr. Opin. Biotechnol., vol. 11, (2000), pp. 338-353.
Gu, Hao, et al., "Droplets Formation and Merging in Two-Phase Flow Microfluidics", Int. J. Mol. Sci., 2011, vol. 12, pp. 2572-2597.
Guillemette, Maxime D. et al., "Surface Topography Induces 3D Self-Orientation of Cells and Extracellular Matrix Resulting in Improved Tissue Function," Integr. Biol., vol. 1, (2009), pp. 196-204.
Gulliksen, Anja, et al., "Parallel Nanoliter Detection of Cancer Markers Using Polymer Microchips," Lab Chip, vol. 5, (2005), pp. 416-420.
Gunther, Axel et al., "Multiphase Microfluidics: From Flow Characteristics to Chemical and Materials Synthesis," Lab Chip, vol. 6, (2006), pp. 1487-1503.
Gunther, Axel et al., "Transport and Reaction in Microscale Segmented Gas-Liquid Flow,", Lab Chip, vol. 4, (2004), pp. 278-286.
Hallen, Magnus et al., "A Comparison of Two Different Assays for Determining S-1008 in Serum and Urine," Clinical Chemistry and Laboratory Medicine, vol. 47, pp. 1025-1029.
Halsey, Thomas C. et al., "The Rotary Electrorheological Effect," International Journal of Modern Physics B, vol. 10, No. 23-24, pp. 3019-3027.
Hansen, Carl et al., "Microfluidics in Structural Biology: Smaller, Faster . . . Better," Curr. Opin. Struct. Biol., vol. 13, (2003), pp. 538-544.
Hansen, Carl L. et al., "A Robust and Scalable Microfluidic Metering Method that allows Protein Crystal Growth by Free Interface Diffusion," Proc. Natl. Acad. Sci. U. S. A., vol. 99, No. 26 (2002), pp. 16531-16536.
Hansen, Carl L., et al., "A Microfluidic Device for Kinetic Optimization of Protein Crystallization and In Situ Structure Determination," J. Am. Chem. Soc., vol. 128, (2006), pp. 3142-3143.
Hatakeyama, Takuji et al., "Microgram-Scale Testing of Reaction Conditions in Solution Using Nanoliter Plugs in Microfluidics with Detection by Ma1DI-MS," Journal of the American Chemical Society, vol. 128, No. 8, (2006), pp. 2518-2519.
Hathcock, James J. et al., "Flow Effects on Coagulation and Thrombosis," Arterioscler. Thromb. Vasc. Biol., vol. 27, (2007), pp. 1729-1737.
Haudek, Verena J. et al, "Proteome Maps of the Main Human Peripheral Blood Constituents," J Proteome Res, vol. 8, No. 8, (2009), pp. 3834-3843.
Hay Burgess, Deborah C. et al., "Global Health Diagnostics," Nature Publishing Group, vol. 444, Suppl. 1, (2006), pp. 1-2.
Hayes, Ronald L. et al. Proteomic Identification of Biomarkers of Traumatic Brain Injury Expert Review of Proteomics, vol. 2, No. 4, (2005), pp. 603-614.
He, Mingyan et al. "Selective encapsulation of single cells and subcellular organelles into picoliter- and femtoliter-volume droplets," Analytical Chemistry, 2005, vol. 77, No. 6, pp. 15391544.
He, Wei et al., "In Vivo Quantitation of Rare Circulating Tumor Cells by Multiphoton Intravital Flow Cytometry," Proceedings of the National Academy of Sciences of the United States of America, vol. 104, (2007), pp. 11760-11765.
He, Xinya et al., "Microfluidic Protein patterning on Silicon Mitride Using Solvent-Extracted Poly(Dimethylsiloxane) Channels," Sensors and Actuators B Chem., vol. 129, No. 2, (2008), pp. 811-817.
Hefner, G.J. et al., "Isothermal Amplification and Multimerization of DNA by Bst DNA Polymerase," Biotechniques, vol. 30, No. 4 (2001), pp. 852-856.
Hellweg, Stephanie et al., "Physiotherapy After Traumatic Brain Injury: A Systematic Review of the Literature," Brain Injury, vol. 22, No. 5, (2008), pp. 365-373.
Hellyer, Tobin J. et al., "Strand Displacement Amplification: A Versatile Tool for Molecular Diagnostics," Expert Rev Mol Diagn., vol. 4, (2004), pp. 251-261.
Herrmann, Marc et al., "Quantification of Low-Picomolar Concentrations of TNF-a in Serum Using the Dual-Network Microfluidic ELISA Platform," Anal. Chem., vol. 80, (2008), pp. 51605167.
Hill, Craig L. "Progress and Challenges in Polyoxometalate-Based Catalysis and Catalytic Materials Chemistry," J. Mol. Catal., vol. 262, (2007), pp. 2-6.
Hillemann, Doris et al., "Use of the Genotype MTBDR Assay for Rapid Detection of Rifampin and Isoniazid Resistance in *Mycobacterium tuberculosis* Complex Isolates" Journal of Clinical Microbiology vol. 43, pp. 3699-3703.
Hirano, Shoji, et al., "Cluster Analysis of Long Time-Series Medical Datasets," Data Mining and Knowledge Discovery: Theory, tools, and Technology VI, Proceedings of SPIE vol. 5433, No. 2, (2004), pp. 13-20.
Hirst, Evan R. et al., "Bond-Rupture Immunosensors—A Review" Biosensors & Bioelectronics, vol. 23, pp. 1759-1768.
Hlushkou, Dzmitry et al., "The Influence of Membrane Ion-Permselectivity on Electrokinetic Concentration Enrichment in Membrane-Based Preconcentration Units," Lab Chip, vol. 8, (2008), pp. 1153-1162.
Holtze, C. et al., "Biocompatible Surfactants for Water-in-fluorocarbon Emulsions," vol. 8, (2008), pp. 1632-1639.
Honda, Masahiro et al., "Serum Glial Fibrillary Acidic Protein Is a Highly Specific Biomarker for Traumatic Brain Injury in Humans Compared With S-1008 and Neuron-Specific Enolase" Journal of Trauma, Injury, Infection and Critical Care, vol. 69, No. 1 (2010), pp. 104-109.
Hosaka, Norimitsu et al., "Rapid Detection of Human Immunodeficiency Virus Type 1 Group M by a Reverse Transcription-Loop-Mediated Isothermal Amplification Assay," J. Virol. Methods, vol. 157, (2009), pp. 195-199.
Hourfar, Michael K. et al., "High-Throughput Purification of Viral RNA Based on Novel Aqueous Chemistry for Nucleic Acid Isolation," Clin. Chem., vol. 51, No. 7 (2005), pp. 12171222.
Hovda, D.A. et al., The Neurochemical and Metabolic Cascade Following Brain Injury—Moving from Animal-Models to Man. Journal of Neurotrauma, vol. 12, No. 5, (1995) pp. 903906.
Hsieh,H. Ben et al., "High Speed Detection of Circulating Tumor Cells," Biosensors & Bioelectronics vol. 21, (2007), pp. 1893-1899.

(56) References Cited

OTHER PUBLICATIONS

Hu, Guoqing et al., "A Microfluidic Chip for Heterogeneous Immunoassay Using Electrokinetical Control," Microfluid. Nanofluid, vol. 1, (2005), pp. 347-355.
Hu, Li-Hong et al., "Synthesis and Biological Activity of Amide Derivatives of Ginkolide A," Journal of Asian Natural Products Research, University of Chicago, vol. 3, (2012), pp. 219227.
Huang, Bo et al., "Counting Low-Copy Number Proteins in a Single Cell," Science, vol. 315, No. 5808, (2007), pp. 81-84.
Huang, Jing et al., "A Yeast Genetic System for Selecting Small Molecule Inhibitors of Protein-Protein Interactions in Nanodroplets," Proc. Natl. Acad. Sci., vol. 94, (1997), pp. 13396-13401.
Huebner, A. et al., "Quantitative detection of protein expression in single cells using droplet microfluidics," Chemical Communications, 2007, pp. 1218-1220.
Huebner, A. et al., "Static Microdroplet Arrays: A Microfluidic Device for Droplet Trapping, Incubation and Release for Enzymatic and Cell-Based Assays," Lab on a Chip, vol. 9, (2009) pp. 692-698.
Hughes, Michael D. et al., "Monitoring Plasma HIV-1 RNA Levels in Addition to CD4(+) Lymphocyte Count Improves Assessment of Antiretroviral Therapeutic Response," Annals of Internal Medicine, vol. 126, No. 12 (1997), pp. 929-938.
Hui, Elliot E. et al., "Micromechanical Control of Cell-Cell Interactions," Proceedings of the National Academy of Sciences of the United States of America, vol. 104, (2007), pp. 57225726.
Hurley, Margaret A. et al., "Automated Statistical Analysis of Microbial Enumeration by Dilution Series", J. Appl. Bacteriol, vol. 55, (1983), pp. 159-164.
Ichikawa, Naoki et al., "Interface Motion of Capillary-Driven Flow in Rectangular Microchannel," Journal of Colloid and Interface Science, vol. 280, (2004), pp. 155-164.
Ichimura, Kunihiro, "Molecular Amplification of Photochemical Events" Journal of Photochemistry and Photobiology A—Chemistry, vol. 158, (2003), pp. 205-214.
Inoue, Tomoya et al., "Microfabricated Multiphase Reactors for the Direct Synthesis of Hydrogen Peroxide from Hydrogen and Oxygen," Ind. Eng. Chem. Res., vol. 46, (2007), pp. 1153-1160.
Irimia, Daniel et al., "Spontaneous Migration of Cancer Cells Under Conditions of Mechanical Confinement" Integrative Biology, vol. 1, (2009), pp. 506-512.
Irish, Jonathan M. et al., "Altered B-Cell Receptor Signaling Kinetics Distinguish Human Follicular Lymphoma B Cells From Tumor-Infiltrating Nonmalignant B Cells," Blood, vol. 108, (2006), pp. 3135-3142.
Irish, Jonathan M. et al., "Single Cell Profiling of Potentiated Phospho-Protein Networks in Cancer Cells," Cell, vol. 118, (2004), pp. 217-228.
Ito, Hiroshi et al., "Chemical Amplification in the Design of Dry Developing Resist Materials" Polymer Engineering and Science, vol. 23, pp. 1012-1018.
Ito, Hiroshi, "Chemical Amplification Resists for Microlithography," Adv. Polym. Sci, vol. 172, (2005), pp. 37-245.
Iverson, Grant L. et al., "Challenges Associated with Post-Deployment Screening for Mild Traumatic Brain Injury in Military Personnel," Clinical Neuropsychologist, vol. 23, No. 8, (2009), pp. 1299-1314.
Izutsu, Ken-ichi et al., "Freeze-Drying of Proteins in Glass Solids Formed by Basic Amino Acids and Dicarboxylic Acids," Chemical & Pharmaceutical Bulletin, vol. 57, (2009), pp. 4348.
Jahnisch, Klaus et al., "Chemistry in Microstructured Reactors," Angew. Chem. Int. Ed. vol. 43, (2004), pp. 406-446.
Jain, K.K., "Neuroprotection in Traumatic Brain Injury," *Drug Discovery Today*, vol. 13 (2324): (2008), pp. 1082-1089.
Jeffreys, alec J. et al., "Repeat Unit Sequence Variation in Minisatellites: A Novel Source of DNA Polymorphism for Studying Variation and Mutation by Single Molecule Analysis" Cell, vol. 60, (1990), pp. 473-485.

Jennings, Cheryl et al., "Comparison of Two Human Immunodeficiency Virus (HIV) RNA Surrogate Assays to the Standard HIV RNA Assay," Journal of Clinical Microbiology, vol. 43, No. 12, (2005), pp. 5950-5956.
Jeon, Noo Li et al., "Generation of Solution and Surface Gradients Using Microfluidic Systems," Langmuir, Vo. 16, (2000), pp. 8311-8316.
Jeon, Noo Li et al., "Neutrophil Chemotaxis in Linear and Complex Gradients of Interleukin-8 Formed in a Microfabricated Device," Nature Biotechnology, vol. 20, (2002), pp. 826-830.
Jeong, Yong-Joo et al., "Isothermal DNA Amplification in Vitro: The Helicase-Dependent Amplification System", Cell Mol Life Sci., vol. 66, (2009), pp. 3325-3336.
Johnson, David et al., "Biochemical Parameters of Recovery in Acute Severe Head-Injury," British Journal of Neurosurgery, vol. 7, No. 1, (1993), pp. 53-59.
Jones, C.J. et al., "Selective Oxidation of Methane to Methanol Catalyzed, with C—H Activation, by Homogeneous, Cationic Gold," Angew. Chem. Int. Ed., vol. 43, (2004), pp. 4626-4629.
Jones, P.A. et al., "Graphical Display of Variability and Inter-Relationships of Pressure Signals in Children with Traumatic Brain Injury," Physiological Measurement, vol. 24, No. 1, (2003) pp. 201-211.
Kaigala, Govind V., "Automated Screening Using Microfluidic Chip-Based PCR and Product Detection to Assess Risk of BK Virus Associated Nephropathy in Renal Transplant Recipients" Electrophoresis (2006), vol. 27, pp. 3753-3763.
Kalinina, Olga, et al., "Nanoliter Scale PCR with TaqMan Detection," Nucleic Acids Research, vol. 25, No. 10, (1997), pp. 1999-2004.
Kanatzidis, Mercouri G. "Beyond Silica: Nonoxidic Mesostructured Materials," Adv. Mater. vol. 19, (2007), pp. 1165-1181.
Kartalov, Emil P. et al., "High-Throughput Multi-Antigen Microfluidic Fluorescence Immunoassays," BioTechniques, vol. 49, No. 1, (2006), pp. 85-90.
Keats, Jonathon et al., "Jargon Watch: Valedictocracy, ISS Toolbag, Chemstrode," Wired Magazine 17.03, Feb. 23, 2009.
Kemp, David J. et al., "Colorimetric Detection of Specific DNA Segments Amplified by Polymerase Chain Reactions," Proc. Natl. Acad. Sci., vol. 86, (1989), pp. 2423-2427.
Kennedy, Robert T et al., "In Vivo Monitoring of Amino Acids by Direct Sampling of Brain Extracellular Fluid at Ultralow Flow Rates and Capillary Electrophoresis," Journal of Neuroscience Methods, vol. 114, (2002), pp. 39-49.
Keymer, Juan E. et al., "Bacterial Metapopulations in Nanofabricated Landscapes," PNAS, vol. 103, No. 46, (2006), pp. 17290-17295.
Kim, Byoung Chan et al., "Quantitative Detection of HIV-1 Particles Using HIV-1 Neutralizing Anti body-Conjugated Beads," Anal Chem., vol. 81, No. 6 (2009), pp. 2388-2393.
Kim, Choong et al., "A Serial Dilution Microfluidic Device Using a Ladder Network Generating Logarithmic or Linear Concentrations," Lab Chip, vol. 8, (2008), pp. 473-479.
Kim, Hyun Jung et al., "Defined Spatial Structure Stabilizes a Synthetic Multispecies Bacteria Community," PNAS, vol. 105, No. 47, (2008), pp. 18188-18193.
Kim, Sung Jae et al., "Concentration Polarization and Nonlinear Electrokinetic Flow Near a Nanofluidic Channel," Physical Review Letters, vol. 99, (2007) pp. 044501.
Kim, Sung Jae et al., "Self-Sealed Vertical Polymeric Nanoporous-Junctions for High-Throughput Nanofluidic App/ications," Analytical Chemistry, vol. 80, No. 9, (2008), pp. 35073511.
Kimura, et al., "Inference of S-System Models of Genetic Networks Using a Cooperative Coevolutionary algorithm," Bioinformatics, vol. 21, No. 7, (2005), pp. 1154-1163.
Kinzelman, Julie L. et al., "Use of IDEXX Colilert-18 and Quanti-Tray/2000 as a Rapid and Simple Enumeration Method for the Implementation of Recreational Water Monitoring and Notification Programs," Lake and Reserv. Manag., vol. 21, No. 1 (2005), pp. 73-77.
Kline, et al., "D Blood Typing and Subtyping Using Plug-Based Microfluidics," Analytical Chemistry, vol. 80, No. 16, (2008), pp. 6190-6197.

(56) References Cited

OTHER PUBLICATIONS

Kobayashi, Juta et al., "A Microfluidic Device for Conducting Gas-Liquid-Solid Hydrogenat Reactions," Science, vol. 304, (2004), pp. 1305-1308.
Kobayashi, Juta, et al., "Multiphase Organic Synthesis in Microchannel Reactors," Chem. Asian J. , vol. 1, (2006), pp. 22-35.
Kobeissy, Firas H. et al. "Psychoproteomic Analysis of Rat Cortex Following Acute Methamphetamine Exposure," Journal of Proteome Research, vol. 7, No. 5, (2008), pp. 1971-1983.
Kobeissy, Firas H. et al., "Novel Differential Neuroproteomics Analysis of Traumatic Brain Injury in Rats" Molecular & Cellular Proteomics, vol. 5, (2005), pp. 1887-1898.
Koh, Chee G. et al., "Integrating Polymerase chain Reaction, Valving, and Electrophoresi.! a Plastic Device for Bacterial Detection", Anal. Chem., vol. 75, (2003), pp. 4591-4598.
Kontos, Hermes A. et al., "Oxygen Radicals in Cerebral Vascular Injury," Circulation Research,vol. 57, No. 4, (1985), pp. 508-516.
Koster, Sarah et al., Influence of Internal Capsid Pressure on Viral Infection by Phage Lambda. Biophysical Journal, vol. 97, No. 6, (2009), pp. 1525-1529.
Kottegoda, Sumith et al., "Demonstration of Low Flow Push-Pull Perfusion," Journal of Neuroscience Methods, vol. 121, No. 1, (2002), pp. 93-101.
Koumura, A. et al., "A Novel Calpain Inhibitor, ((1S)-4(((I s)-1-Benzyl-3-Cyclopropylamina 2,3-Di-Oxopropyl)Amino)Carbonyl)-3-Methylbutyl) Carbamic Acid 5-Methoxy-3-Oxapentyl Ester, Protects Neuronal Cells from Cerebral Ischemia-Induced Damage in Mice," Neuroscience, vol. 157, No. 2, (2008), pp. 309-318.
Kraeft, Stine-Kathrein et al., "Reliable and Sensitive Identification of Occult Tumor Cells U the Improved Rare Event Imaging System" Clinical Cancer Research, vol. 10, (2004), pp. 3020-3028.
Kralj, Jason G. et al., "Integrated Continuous Microfluidic Liquid-Liquid Extraction," Lab C vol. 7, No. 2, (2007), pp. 256-263.
Kreutz, James E. et al., "Laterally Mobile, Functionalized Self-Assembled Monolayers at t1 Fluorous—Aqueous Interface in a Plug-Based Microfluidic System: Characterization and Testing with Membrane Protein Ctystallization," J. Am. Chem. Soc., vol. 131, (2009), pp. 6042-6043.
Kreutz, Jason E. et al., "Evolution of Catalysts Directed by Genetic algorithms in a Plug-Based Microfluidi Device Tested with Oxidation of Methane by Oxygen," J. Am Chem Soc vol. 132, No. 9, (2010), pp. 3128-3132.
Krivacic, Robert T. et al., "A Rare-Cell Detector for Cancer" PNAS, vol. 101, No. 29, (200 pp. 10501-10504.
Krstenansky, John L. et al., "Biocatalytic Combinatorial Synthesis," Bioorganic & Medicine Chemistry, vol. 7, No. 10, pp. 2157-2162.
Krutzik, Peter 0. et al., "High-Content single-Cell Drug Screening with Phosphospecific F1 Cytometry," Nat. Chem. Biol., vol. 4, No. 2 (2008), pp. 132-142.
Kulakovich, Olga et al., Enhanced Luminescence of CdSe Quantum Dots on Gold Colloid Nano Letters, vol. 2, pp. 1449-1452.
Kumar,Vineet et al., "In Situ Precipitation and Vacuum Drying of Interferon alpha-2a: Development of a Single-Step Process for Obtaining Dry, Stable Protein Formulation," International Journal of Pharmaceutics, vol. 366, (2009), pp. 88-98.
Labbett, Wendy et al., "Comparative Evaluation of the ExaVir Load Version 3 Reverse Transcriptase Assay for Measurement of Human Immunodeficiency Virus Type 1 Plasma Load," J. Clin. Microbiol., vol. 47, No. 10, (2009), pp. 3266-3270.
Labinger, Jay A. et al., "Understanding and Exploiting c—H Bond Activation," Nature, vol. 417, (2002), pp. 507-514.
Lacharme, F. et al., "Magnetic Beads Retention Device for Sandwich Immunoassay: Comparison of Off-Chip and On-Chip Antibody Incubation," Microfluid. Nanofluid, vol. 7, (2009), pp. 479-487.
Lai,Siyi et al., Design of a Compact Disk-Like Microfluidic Platform for Enzyme-Linked Immunosorbent Assay, Anal. Chem., vol. 76, No. 7, (2004), pp. 1832-1837.
Lam, Kit s. et al., "The One-Bead-One-Compound Combinatorial Library Method," Chem. Rev., vol. 97, (1997), pp. 411-448.
Lapizco-Encinas, Blanca H. et al., "An Insulator-Based (Electrodeless) Dielectrophoretic Concentrator for Microbes in Water", Journal of Microbiological Methods, vol. 62, (2005) pp. 317-326.
Lau, Billy T.C. et al., "A Complete Microfluidic Screening Platform for Rational Protein Crystallization," J. Am. Chem. Soc., vol. 129, (2007), pp. 454-455.
Laws, Derek R. et al., "Bipolar Electrode Focusing: Simultaneous Concentration Enrichment and Separation in a Microfluidic Channel Containing a Bipolar Electrode" Analytical Chemistry, vol. 81 (2009), pp. 8923-8929.
Leamon, John H. et al., "Overview: Methods and Applications for Droplet Compartmentalization of Biology," Nature Methods, vol. 3, (2006), pp. 541-543.
Leardi, Riccardo et al., "Genetic algorithms in Chemistry," J. Chromatogr. A, vol. 1158, (2007), pp. 226-233.
Leclerc, E. et al., "Study of Osteoblastic Cells in a Microfluidic Environment" Biomaterials, vol. 27, (2007), pp. 586-595.
Lee, Jeong Yong et al., Metal-Organic Framework Materials as Catalysts, Soc. Rev., vol. 38, (2009), pp. 1450-1459.
Lersch, Martin et al., "Mechanistic Aspects of C—H Activation by Pt. Complexes," Chem. Rev., vol. 105, (2005), pp. 2471-2526.
Li et al., "A Plug-Based Microfluidic System for Dispensing Lipidic Cubic Phase (LCP) Material Validated by Crystallizing Membrane Proteins in Lipidic Mesophases," Microfluid Nanofluid , vol. 8, (2010), pp. 789-798.
Li et al., "Nanoliter Microfluidic Hybrid Method for Simultaneous Screening and Optimization Validated with Crystallization of Membrane Proteins," PNAS vol. 103, No. 51, (2006), pp. 19243-19248.
Li et al., "Simple Host-Guest Chemistry to Modulate the Process of Concentration and Crystallization of Membrane Proteins by Detergent Capture in a Microfluidic Device," J. Am. Chem. Soc., vol. 130, 2008, pp. 14324-14328.
Li, Xu et al., "Paper-Based Microfluidic Devices by Plasma Treatment" Analytical Chemistry, vol. 80, (2008), pp. 9131-9134.
Li, Zhaohui, et al., "Detection of Single-Molecule DNA Hybridization using Enzymatic Amplification in an Array of Femtoliter-Sized Reaction Vessels," J. Am. Chem. Soc., vol. 130, (2008), pp. 12622-12623.
Liang, Ru-Qiang, et al., "Colorimetric Detection of Protein Microarrays Based on Nanogold Probe Coupled with Silver Enhancement" Journal of Immunological Methods, vol. 285, (2004), pp. 157-163.
Liao, Warren T., "Clustering of Time Series Data—A Survey." Pattern Recognition, vol. 38, No. 11, (2005), pp. 1857-1874.
Lim, C.T. et al., "Bead-Based Microfluidic Immunoassays: The Next Generation," Biosens. Bioelectron, vol. 22, (2007), pp. 1197-1204.
Lin, Jessica et al., "A Symbolic Representation of Time Series, with Implications for Streaming algorithms," DMKD, (2003), San Diego, CA.
Lin, Minren et al., "Direct Catalytic Conversion of Methane to Acetic Acid in an Aqueous Medium," Letters to Nature, vol. 368, (1994), pp. 613-615.
Linder, Vincent et al., "Application of Surface biopassivated Disposable Poly(Dimethylsiloxane)/Glass Chips to a Heterogeneous Competitive human Serum Immunoglobulin G Immunoassay with Incorporated Internal Standard," Electrophoresis, vol. 23, (2002), pp. 740-749.
Linder, Vincent et al., "Reagent-Loaded Cartridges for Valveless and Automated Fluid Delivery in Microfluidic Devices," Anal. Chem.vol. 77, No. 1, (2005), pp. 64-71.
Lisi, T.L. et al., "Comparison of Microdialysis and Push-Pull Perfusion for Retrieval of Serotonin and Norepinephrine in the Spinal Cord Dorsal Horn," Journal of Neuroscience Methods, vol. 126, No. 2, (2003) pp. 187-194.
Liu, Jian et al., "A Nanoliter Rotary Device for Polymerase Chain Reaction," Electrophoresis, vol. 23, (2002), pp. 1531-1536.
Liu, Ming Chen, et al.,"Extensive Degradation of Myelin Basic Protein Isoforms by Calpain Following Tramatic Brain Injury," Journal of Neurochemistry, vol. 98, (2006), pp. 700-712.

(56) References Cited

OTHER PUBLICATIONS

Liu, Ming Cheng et al., "Comparing Calpain- and Caspase-3-Mediated Degradation Patterns in Traumatic Brain Injury by Differential Proteome Analysis," Biochemical Journal vol. 394, (2006) pp. 715-725.
Liu, Ming Cheng et al., "Ubiquitin C-Terminal Hydrolase-L1 as a Biomarker for Ischemic and Traumatic Brain Injury in Rats," European Journal of Neuroscience, vol. 31, No. 4, (2010), pp. 722-732.
Liu, Weishan, et al., "Isolation, Incubation, and Parallel Functional Testing and Identification by FISH of Rare Microbial Single-Copy Cells from Multi-Species Mixtures Using the Combination of Chemistrode and Stochastic Confinement," Lab Chip, vol. 9, No. 15, (2009), pp. 2153-2162.
Liu, Ying et al., "Dynamics of Coalescence of Plugs with a Hydrophilic Wetting Layer Induced by Flow in a Microfluidic Chemistrode". Langmuir, vol. 25, No. 5, (2009), pp. 2854-2859.
Lo, Tsz-Yan M. et al., "Pediatric Brain Trauma Outcome Prediction Using Paired Serum Levels of Inflammatory Mediators and Brain-Specific Proteins" Journal of Neurotrauma, vol. 26, pp. 1479-1487.
Locascio, Joseph J. et al., "Time Series Analysis in the Time Domain and Resampling Methods for Studies of Functional Magnetic Resonance Brain Imaging," Human Brain Mapping, vol. 5, No. 3, (1997), pp. 168-193.
Long, De-Liang, et al., "Towards Polyoxometalate-Integrated Nanosystems," Chem.-Eur. J. vol. 12, (2006), pp. 3699-3706.
Love, J. Christopher, et al., A Microengraving Method for Rapid Selection of Single Cells Producing Antigen-Specific Antibodies, Nature Biotechnol., vol. 24, No. 6, (2006), pp. 703707.
Loyer, Milton W., et al., "Interval Estimation of the Density of Organisms Using a Serial-Dilution Experiment," Biometrics, vol. 40, No. 4, (1984) pp. 907-916.
Lu, Miao-Jen et al., "Detection of Elevated Signaling Amino Acids in Human Diabetic Vitreous by Rapid Capillary Electrophoresis," Experimental Diabetes Research, vol. 2007, Article ID 39765, 6p.
Lun, Fiona M.F. et al., "Microfluidics Digital PCR Reveals a Higher Than Expected Fraction of Fetal DNA in Maternal Plasma," vol. 54, (2008), pp. 1664-1672.
MacDougall, David S. et al., "Quantitative Measurement of HIV RNA Techniques Clinical Applications," J. of Intl Assoc. of Physicians in AIDS Care, vol. 2, No. 11 (1996), pp. 9-14.
Macek, K., and Beavafova, H., "Papers, Ready-for-Use Plates and Flexible Sheets for Chromatography, " *Chromatographic* Reviews, vol. 15, No. 1, (1971), pp. 1-28.
Madou, Marc, et al., "Lab on a CD," Annu. Rev. Biomed. Eng., vol. 8, (2006), pp. 601-628.
Maerkl, Sebastian J. et al., "A Systems Approach to Measuring the Binding Energy Landscapes of Transcription Factors" Science, vol. 315, (2007), pp. 233-237.
Maier, Wilhelm F, et al., "Combinatorial and High-Throughput Materials Science," S Angew. Chem.-Int. Edit., vol. 46, (2007), pp. 6016-6067.
Maiorella, Brian, et al., "Crossflow Microfiltration of Animal Cells," Biotechnology and Bioengineering, vol. 37, (1991), pp. 121-126.
Majchrowicz, "Beyond Antiretroviral Access: Low-Cost Laboratory Tests Needed for the Developing World," AIDS, vol. 17, Suppl 4, (2003), pp. S13-S15.
Makinen, Johanna, et al., Automated Purification of Borrelia Burgdorferi s.l. PCR Products with KingFisher Magnetic Particle Processor Prior to Genome Sequencing, J. Magnetism and Magnetic Materials, vol. 225, (2001), pp. 134-137.
Marcy, Yann, et al., "Nanoliter Reactors Improve Multiple Displacement Amplification of Genomes from Single Cells," PLoS Genetics, vol. 3, No. 9, (2007), pp. 1702-1708.
Markoulatos, P., et al., "Multiplex Polymerase Chain Reaction: A practical Approach," J. Clin. Lab. Anal., vol. 16, (2002), pp. 47-51.
Marriott, Gerard, "Time-Resolved Delayed Luminescence Image Microscopy Using an Europium Ion Chelate Complex," Biophysical Journal, vol. 67, (1994), pp. 957-965.
Martin, Anandi, et al., "Resazurin Microtiter Assay Plate Testing of *Mycobacterium tuberculosis* Susceptibilities to Second-Line Drugs: Rapid, Simple, and Inexpensive Method," Antimicrobial Agents and Chemotherapy, vol. 47, No. 11, (2003), pp. 3616-3619.
Martin, James E. et al., "Strong Intrinsic Mixing in Vortex Magnetic Fields," Physical Review, vol. 80, (2009), pp. 016312.
Martin, James E., et al., "Simulation of the Athermal Coarsening of Composites Structured by a Uniaxial Field," Journal of Chemical Physics vol. 108, No. 9, (1998), pp. 3765-3787.
Martinez, Andres et al., "FLASH: A Rapid Method for Prototyping Paper-Based Microfluidic Devices," Lab Chip, vol. 8, (2008), pp. 2146-2150.
Martinez, Andres W. et al., "Patterned Paper as a Platform for Inexpensive, Low-Volume, Portable Bioassays," Angew. Chem. Int. Ed. vol. 46, (2007), pp. 318-1320.
Martinez, Andres W. et al., "Simple Telemedicine for Developing Regions: Camera Phones and Paper-Based Microfluidic Devices for Real-Time, Off-Site Diagnosis," Analytical Chemistry, vol. 80, No. 10, (2008), pp. 3699-3707.
Matsubara, Yasutaka et al., "Application of On-Chip Cell Cultures for the Detection of allergic Response". Biosensors & Bioelectronics, vol. 19, (2004), pp. 741-747.
Matsubara, Yasutaka et al., "Microchamber Array based DNA Quantification and Specific Sequence Detection from a Single Copy via PCR in Nanoliter Volumes," Biosensors and Bioelectronics, vol. 20, (2005), pp. 1482-1490.
McCormack, Devin et al., "Photoacoustic Detection of Melanoma Micrometastasis in Sentinel Lymph Nodes". Journal of Biomechanical Engineering—Transactions of the Asme, vol. 131 ( 2009).
McDonald, J. Cooper, et al., "Poly(Dimethylsiloxane) as a Material for Fabricating Microfluidic Devices," Accounts of Chem. Res., vol. 35, No. 7, (2002), pp. 491-499.
McPherson, A. et al., "Crystallization of Biological Macromolecules," Cold Spring Harbor Laboratory Press, (1999).
Meier, Matthias et al., "Plug-Based Microfluidics with Defined Surface Chemistry to Miniaturize and Control Aggregation of Amyloidogenic Peptides," Angewandte Chemie—International Edition, vol. 48, No. 8, (2009), pp. 1487-1489.
Melle, Sonia et al., "Chain Model of a Magnetorheological Suspension in a Rotating Field," Journal of Chemical Physics, vol. 118, No. 21, pp. 9875-9881.
Melle, Sonia et al., "Structure and Dynamics of Magnetorheological Fluids in Rotating Magnetic Fields," Physical Review E, vol. 61, vol. 4, pp. 4111-4117.
Mellors, John W. et al., "Prognosis in HIV-1 Infection Predicted by the Quantity of Virus in Plasma," Science, New Series, vol. 272, No. 5265, (1996), pp. 1167-1170.
Meyvantsson, Ivar et al., "Cell Culture Models in Micro fluidic Systems". Annual Review of Analytical Chemistry 1, 423-449 (2008).
Michels, Peter C. et al., "Combinatorial Biocatalysis: A Natural Approach to Drug Discovery," Trends in Biotechnology, vol. 16, No. 5, pp. 210-215.
Miller, M. Craig et al., "Significance of Circulating Tumor Cells Detected by the CellSearch System in Patients with Metastatic Breast Colorectal and Prostate Cancer". Journal of Oncology 2010, Article ID 617421, 8 pages.
Miller, Oliver J., et al., "Directed Evolution by In Vitro Compartmentalization," Nat. Methods, vol. 3, No. 7, (2006), pp. 561-570.
Mohamed, et al., "Isolation of Tumor Cells Using Size and Deformation," Journal of Chromatography, (2009) pp. 8289-8295.
Mohamed, Hisham et al. "Development of a Rare Cell Fractionation Device: Application for Cancer Detection," IEEE Transactions on Nanobioscience, vol. 3, No. 4 (2004), pp. 251-256.
Monckton, Darren G. et al., "Minisatellite"Isoallele" Discrimination in Pseudohomozygotes by Single Molecule PCR and Variant Repeat Mapping," Genomics, vol. 11, (1991), pp. 465-467.
Moorthy, Jaisree et al., "In Situ Fabricated Porous Filters for Microsystems," Lab Chip, vol. 3, (2003), pp. 62-66.
Morales, D.M. et al., "Experimental Models of Traumatic Brain Injury: Do we really need to build a better mousetrap?" Neuroscience, vol. 136, No. 4, (2005), pp. 971-989.

(56) References Cited

OTHER PUBLICATIONS

Morris, L.D. et al., "Use of a New HemoCue System for Measuring Haemoglobin at Low Concentrations," Clinical and Laboratory Haematology, vol. 23, No. 2, (2001), pp. 91-96.

Morton, Keith J. et al., "Hydrodynamic Metamaterials: Microfabricated Arrays to Steer, Refract, and Focus Streams of Biomaterials," Proceedings of the National Academy of Sciences of the United States of America, vol. 105, (2008), pp. 7434-7438.

Moser, Y. et al., On-Chip Immuno-Agglutination Assay with Analyte Capture by Dynamic Manipulation of Superparamagnetic Beads, Lab Chip, vol. 9, (2009), pp. 3261-3267.

Mountzouros, Kenneth T. et al., "Detection of Complement-Mediated Antibody-Dependent Bactericidal Activity in a Fluorescence-Based Serum Bactericidal Assay for Group B Neisseria Meningitidis," J. Clin. Microbiol.,vol. 38, No. 8, (2000), pp. 2878-2884.

Murakami, Yoshihiro, et al., "On-Chip Micro-flow Plystyrene Bead-Based Immunoassay for Quantitative Detection of Tacrolimus(FK506)," Anal. Biochem., vol. 334, (2004), pp. 111-116.

Murshudov, Garib N. et al., "Refinement of Maromolecular Structures by the Maximum-Likelihood Method," Acta Crystallographica Section D—Biological Crystallography, vol. 53, (1997), pp. 240-255.

Myers, R.D. et al., "Simultaneous Comparison of Cerebral Dialysis and Push-Pull Perfusion in the Brain of Rats: A Critical Review," Neuroscience and Biobehavioral Reviews, vol. 22, No. 3, (1998), pp. 371-387.

Nagrath, Sunitha et al., "Isolation of Rare Circulating Tumour Cells in Cancer Patients by Microchip Technology" Nature, vol. 450, (2007), pp. 1235-U10.

Nam,Jwa-Min et al., "Nanoparticle-Based Bio-Bar Codes for the Ultrasensitive Detection of Proteins" Science, vol. 301, pp. 1884-1886.

Neuman de Vegvar, Henry E., et al., "Microarray Profiling of Antiviral Antibodies for the Development of Diagnostics, Vaccines, and Therapeutics," Clin. Immunol., vol. 111, (2004), pp. 196-201.

Ng, Joseph D. et al., "In Situ X-ray Analysis of Protein Crystals in Low-Birefringent and X-ray Transmissive Plastic Microchannels," Acta Crystallogr. , vol. D64, (2008), pp. 189-197.

Ng, Joseph D. et al., "Protein crystallization by capillary counterdiffusion for applied crystallographic structure determination," Journal of Structural Biology, 2003, vol. 142, pp. 218-231.

Ng, Joseph D. et al., "Protein Crystallization by Capillary Counterdiffusion for Applied Crystallographic Structure Determination," J. Struct. Biol., vol. 142, (2003), pp. 218-231.

Niemela, S.I. et al., "A Comparison of the International Standards Organisation Reference Method for the Detection of Coliforms and *Escherichia coli* in Water with a Defined Substrate Procedure," J. Appl. Microbiol., vol. 95, (2003), pp. 1285-1292.

Niemeyer, Christof M. et al., "Immuno-PCR: High Sensitivity Detection of Proteins by Nucleic Acid Amplification" Trends in Biotechnology, vol. 23, No. 4, (2006), pp. 208-216.

Nisisako, Takasi et al., "Formation of Droplets Using Branch Channels in a Microfluidic Circuit," SICE, Aug. 2002, pp. 1262-1264.

Nisisako, Takasi et al., "Synthesis of Monodisperse Bicolored Janus Particles with Electrical Anisotropy Using a Microfluidic Co-Flow System," Advanced Materials, vol. 18, (2006), pp. 1152-1156.

Nosworthy, Neil J. et al., "A New Surface for Immobilizing and Maintaining the Function of Enzymes in a Freeze-Dried State," Biomacromolecules, vol. 10, (2009), pp. 2577-2583.

O'Brien, J. et al., "Investigation of the alamar Blue (Resazurin) Fluorescent dye for the Assessment of Mammalian Cell Cytotoxicity," Molecular Toxicology, vol. 164, (2001), pp. 132-132.

Oehler, V.G. et al., "Absolute Quantitative Detection of ABL Tyrosine Kinase Domain Point Mutations in Chronic Myeloid Leukemia Using a Novel Nanofluidic Platform and Mutation-Specific PCR," vol. 23, (2009), pp. 396-399.

Office action dated Feb. 28, 2014 for U.S. Appl. No. 13/257,811.

Office action dated Feb. 28, 2014 for U.S. Appl. No. 13/467,482.

Ohji, Hiroshi, et al., "Macro Porous Silicon Formation for Micromachining," Micromachining and Microfabrication Process Technology III, SPIE vol. 3223, No. 189, (1997), pp. 29-30.

Ohrenberg, Arne et al., Application of Data Mining and Evolutionary Optimization in Catalyst Discoery and High-Throughput Experimentation—Techniques, Strategies, and Software, QSAR Comb. Sci., vol. 24, (2005), pp. 29-37.

Okie, Susan et al., "Traumatic Brain Injury in the War Zone" The New England Journal of Medicine, vol. 352, No. 20, (2005) pp. 2043-2047.

Olson, Eric N., "The Microarray Data Analysis Process: From Raw Data to Biological Significance," The Am. Soc. for Experimental NeuroTherapeutics, vol. 3, (2006), pp. 373-383.

Onal, Yucel et al., "Application of a Capillary Microreactor for Selective Hydrogenation of a,f3-Unsaturated aldehydes in Aqueous Multiphase Catalysis," Chem. Eng. Technol., vol. 28, No. 9, (2005), pp. 972-978.

O'Neill, Roger A. et al., "Isoelectric Focusing Technology Quantifies Protein Signaling in 25 Cells," Proceedings of the National Academy of Sciences of the United States of America, vol. 103, (2006), pp. 16153-16158.

Ong, Siew-Min et al., "A Gel-Free 3D Microfluidic Cell Culture System" Biomaterials, vol. 29, (2008), pp. 3237-3244.

Ottens, Andrew K. et al., "Neuroproteomics in Neurotrauma," Mass Spectrometry Reviews, vol. 25, (2006), pp. 380-408.

Ottens, Andrew K. et al., "Novel Neuroproteomic Approaches to Studying Traumatic Brain Injury Neurotrauma," Progress in Brain Research, vol. 161, (2007), pp. 401-418.

Otwinowski, Zbyszek et al., "Processing of X-Ray Diffraction Data Collected in Oscillation Mode," Methods in Enzymology, vol. 276, (1997), pp. 307-326.

Paegel, Brian M. et al., "Microfluidic Serial Dilution Circuit" Analytical Chemistry, vol. 78, (2006), pp. 7522-7527.

Pai, Nittika Pant et al., "Evaluation of Diagnostic Accuracy, feasibility and Client Preference for Rapid Oral Fluid-Based Diagnosis of HIV Infection in Rural India," PLoS ONE, Issue 4, (2007), pp. e367.

Pan, Chu-Hsiang et al., "A Visual DNA Chip for Simultaneous Detection, Genotyping and Differentiation of Wild-type and Vaccine-Type Classical Swine Fever Virus" Taiwan Veterinary Journal, No. 34, No. 2 (2008), pp. 66-76.

Papa, Linda et al., "Ubiquitin C-Terminal Hydrolase is a Novel Biomarker in Humans for Severe Traumatic Brain Injury," Critical Care Medicine, vol. 38, No. 1 (2010), pp. 138-144.

Parekkadan, Biju et al., "Cell-Cell Interaction Modulates Neuroectodermal Specification of Embryonic Stem Cells" Neuroscience Letters, vol. 438, (2008), pp. 190-195.

Paris, Pamela L. et al., "Functional Phenotyping and Genotyping of Circulating Tumor Cells from Patients with Castration Resistant Prostate Cancer" Cancer Letters, vol. 277, (2009), pp. 164-173.

Park, Jungwook et al., "A Calcium Ion-Selective Electrode Array for Monitoring the Activity of HepG2/C3As in a Microchannel," Sensors and Actuators B, vol. 174, (2012), pp. 473-477.

Park, Sungsu et al., "Influence of Topology on Bacterial Social Interaction" Proceedings of the National Academy of Sciences of the United States of America, vol. 100, (2003), pp. 13910-13915.

Periana, Roy A. et al., "Platinum Catalysts for the High-Yield Oxidation of Methane to a Methanol Derivative," Science, vol. 280, No. 5363, (1998), pp. 560-564.

Perry, John J. et al., "Design and Synthesis of Metal-Organic Frameworks Using Metal-Organic Polyhedra as Supermolecular Blocks," Chem. Soc. Rev., vol. 38, (2009), pp. 14001417.

Persidis, Aris et al., "High-Throughput Screening," Nat. Biotechnol., vol. 16 (1998), pp. 488489.

Petronis, Sarunas et al., "Model Porous Surfaces for Systematic Studies of Material-Cell Interactions," Journal of Biomedical Materials Research—Part A,, vol. 66 (3), (2003), pp. 707-721.

Phan, Sieu et al., "A Novel Pattern Based Clustering Methodology for Time-Series Microarray Data," International Journal of Computer Mathematics, vol. 84, No. 5, (2007), pp. 585-597.

(56) References Cited

OTHER PUBLICATIONS

Pichonat, Tristan et al., "Development of Porous Silicon-Based Miniature Fuel Cells," Journal of Micromechanics and Microengineering, vol. 15, (2005), pp. 5179-5184.
Pihl, Johan et al., "Microfluidics for Cell-Based Assays," Materials Today, vol. 8, No. 12, (2005), pp. 46-51.
Pikal, Michael J. et al., "Solid State Chemistry of Proteins: II. The Correlation of Storage Stability of Freeze-Dried Human Growth Hormone (hGH) with Structure and Dynamics in the Glassy Solid," Journal of Pharmaceutical Sciences, vol. 97, No. 12 (2008), pp. 5106-5121.
Pike, Brian R. et al., "Regional Calpain and Caspase-3 Proteolysis of alpha-Spectrin After Traumatic Brain Injury," Neuroreport, vol. 9, No. 11, (1998), pp. 2437-2442.
Pineda, Jose A. et al., "Clinical Significance of all-Spectrin Breakdown Products in Cerebrospinal Fluid After Severe Traumatic Brain Injury" Journal of Neurotrauma, vol. 24, No. 1 (2007), pp. 354-366.
Pipper, Juergen et al., "Catching Bird Flu in a Droplet," Nature Medicine, vol. 13, No. 10, (2007), pp. 1259-1263.
Plotkin, Steven S. "Generalization of Distance to Higher Dimensional Objects," Proceedings of the National Academy of Sciences of the United States of America, vol. 104, No. 38, (2007), pp. 14899-14904.
Pollack, M.G. et al., "Electrowetting-based actuation of droplets for integrated microfluidics," Lab Chip, 2002, vol. 2, pp. 96-101.
Pompano, Rebecca R. et al., "Rate of Mixing Controls Rate and Outcome of Autocatalytic Processes: Theory and Microfluidic Experiments with Chemical Reactions and Blood Coagulation," Biophysical Journal, vol. 95, No. 3, (2008), pp. 1531-1543.
Potts, Matthew B. et al., "Models of Traumatic Cerebellar Injury," Cerebellum, vol. 8, No. 3, (2009) pp. 211-221.
Powers, Mark J. et al., "A Microfabricated Array Bioreactor for Perfused 3D Liver Culture" Biotechnology and Bioengineering, vol. 78, (2002), pp. 257-269.
Pregibon, Daniel C. et al., "Multifunctional Encoded Particles for High-Throughput Biomolecule Analysis," Science, vol. 315, (2007), pp. 1393-1396.
Proost, P. et al., "The Role of Chemokines in Inflammation" International Journal of Clinical & Laboratory Research, vol. 26, (1996), pp. 211-223.
Proust, Anna et al., "Functionalizaiton of Polyoxometalates: Towards Advanced Applications in Catalysis and Materials Science," Chem. Commun., (2008), pp. 837-1852.
Raghupathi, Ramesh et al., "Cell Death Mechanisms Following Traumatic Brain," Brain Pathology, vol. 14, No. 2, (2004), pp. 215-222.
Rah, Tatsuki et al., "The Novel Free Radical Scavenger, Edaravone, Increases Neural Stem Cell Number Around the Area of Damage Following Rat Traumatic Brain Injury. Neurotoxicity Research," vol. 16, No. 4, (2009), pp. 378-389.
Ravula, Surendra K. et al., "Spatiotemporal Localization of Injury Potentials in DRG Neurons During Vincristine-Induced Axonal Degeneration," Neuroscience Letters, vol. 415, (2007), pp. 34-39.
Rida, A. et al., "Manipulation of Self-Assembled Structures of Magnetic Beads for Microfluidic Mixing and Assaying," Anal Chem., vol. 77, No. 21, (2004), pp. 6239-6246.
Riegger, L. et al., "Read-Out Concepts for Multiplexed Bead-Based Fluorescence Immunoassays on Centrifugal Microfluidic Platforms," Sensors and Actuators A, vol. 126, (2006), pp. 455-462.
Rifai, Nader et al., Protein Biomarker Discovery and Validation: The Long and Uncertain Path to Clinical Utility, Nat. Biotechnol., vol. 24, No. 8 (2006), pp. 971-983.
Ringger, N.C. et al., "A Novel Marker for Traumatic Brain Injury: CSF alpha II-Spectrin Breakdown Product Levels" Journal of Neurotrauma, vol. 21, pp. 1443-1456.
Rissin, David M. et al., "Digital Concentration Readout of Single Enzyme Molecules Using Femtoliter Arrays and Poisson Statistics" Nano Letters, vol. 6, pp. 520-523.
Rissin, et al., Digital Readout of Target Binding with Attomole Detection Limits via Enzyme Amplification in Femtoliter Arrays, J. Am. Chem. Soc., vol. 128 (2006), pp. 6286-6287.
Roach, L. Spencer et al., "Controlling Nonspecific Protein Adsorption in a Plug-Based Microfluidic System by Controlling Interfacial Chemistry Using Fluorous-Phase Surfactants," Anal. Chem.,vol. 77, No. 3, (2005), pp. 785-796.
Rodemerck, U. et al., "Application of a Genetic algorithm and a Neural Network for the Discovery and Optimization of New Solid Catalytic Materials," Applied Surface Science, vol. 223, (2004), pp. 168-174.
Rodriguez-Villarreal, Angeles Ivan et al., "High Flow Rate Microfluidic Device for Blood Plasma Separation Using a Range of Temperatures," Lab Chip, vol. 10, (2010), pp. 211-219.
Romano, Joseph W. et al., "NASBA Technology: Isothermal RNA Amplification in Qualitative and Quantitative Diagnostics," Immunol Invest., vol. 26, Nos. 1&2, (1997), pp. 15-28.
Rowat, Amy C. et al., "Tracking Lineages of Single Cells in Lines Using a Microfluidic Device" Proceedings of the National Academy of Sciences of the United States of America, vol. 106, (2090), pp. 18149-18154.
Rowe, Laura et al., "Active 3-D Microscaffold System With Fluid Perfusion for Culturing in Vitro Neuronal Networks" Lab Chip, vol. 7, (2007), pp. 475-482.
Ryan, Colleen et al., "Rapid Assay for Mycobacterial Growth and Antibiotic Susceptibility Using Gel Microdrop Encapsulation," J. Clin. Microbiol., vol. 33, No. 7, (1995), pp. 1720-1726.
Ryu, WonHyoung et al., "The Construction of Three-Dimensional Micro-Fluidic Scaffolds of Biodegradable Polymers by Solvent Vapor Based Bonding of Micro-Molded Layers," Biomaterials, vol. 28 (2007), pp. 1174-1184.
Sachs, Karen et al., "Causal Protein-Signaling Networks Derived from Multiparameter Single-Cell Data,"Science, vol. 308 (2005), pp. 523-529.
Sakaki, Kelly et al., "RoboSCell: An Automated Single Cell Arraying and Analysis Instrument" Biomedical Microdevices, vol. 11, (2009), pp. 1317-1330.
Sakudo, Akikazu et al., "Efficient Capture of Infectious H5 Avian Influenza Virus Utilizing Magnetic Beads Coated With Anionic Polymer," Biochem. Biophys. Res. Commun., vol. 377, (2008), pp. 85-88.
Salemme, F.R. et al., "A Free Interface Diffusion Technique for the Crystallization of Proteins for X-Ray Crystallography," Archives of Biochemistry and Biophysics, vol. 151, (1972), pp. 533-539.
Sanishvili, Ruslan et al., "A 7 iiM Mini-Beam Improves Diffraction Data From Small or Imperfect Crystals of Macromolecules," Biol. Crystallography, vol. D64, (2008), pp. 425-435.
Sano, Takeshi et al., "immuno-PCR: Very Sensitive Antigen Detection by Means of Specific Antibody-DNA Conjugates" Science, vol. 258, pp. 120-122.
Sasuga, Yasuhiro et al., Single-Cell Chemical Lysis Method for Analyses of Intracellular Molecules Using an Array of Picoliter-Scale Microwells, Anal. Chem., vol. 80, No. 23, (2008), pp. 9141-9149.
Sato, Kiichi et al., "Determination of Carcinoembryonic Antigen in Human Sera by Integrated Bead-Bed Immunoasay in a Microchip for Cancer Diagnosis," Anal. Chem.vol. 73, No. 6, (2001), pp. 1213-1218.
Schmitz, Christian H.J. et al., "Dropspots: A Picoliter Array in a Microfluidic Device," Lab Chip, vol. 9, (2009), pp. 44-49.
Scott, Lesley E. et al., "Evaluation of the Abbott m2000 RealTime Human Immunodeficiency Virus Type 1 (HIV-1) Assay for HIV Load Monitoring in South Africa Compared to the Roche Cobas AmpliPrep-Cobas Amplicor, Roche Cobas AmpliPrep-Cobas TaqMan HIV-1, and BioMerieux NucliSENS EasyQ HIV-1 Assays," J. Clin. Microbiol. , vol. 47, (2009), pp. 22092217.
Selvin, Paul R. "Principles and Biophysical Applications of Lanthanide-Based Probes," Annu. Rev. Biophys. Biomol. Struct., vol. 31, (2002), pp. 275-302.
Senkan, Selim, "Combinatorial Heterogeneous Catalysis—A New Path in an Old Field," Angew Chem.-Int. Edit., vol. 40, (2001), pp. 312-329.

(56) References Cited

OTHER PUBLICATIONS

Seong, Gi Hun et al., "Efficient Mixing and Reactions within Microfluidic Channels Using Microbead-Supported Catalysts" JACS, 2002, vol. 124, pp. 13360-13361 (Published Online Oct. 17, 2002).

Seong, Gi Hun et al., "Fabrication of Microchambers Defined by Photopolymerized Hydrogels and Weirs within Microfluidic Systems: Application to DNA Hybridization", Anal. Chem., 2002, vol. 74, pp. 3372-3377 (Published Online Jun. 6, 2002).

Sharma, Rajesh K. et al., "Multiplex Immunoassay Analysis of Biomarkers in Clinically Accessible Quantities of Human Aqueous Humor," Molecular Vision, vol. 15, (2009), pp. 6069.

Shaw, C.T. et al., "Using Cluster Analysis to Classify Time Series," Physica D. vol. 58, (1992), pp. 288-298.

Shen, Hong et al., "A Microfluidic Chip Based Sequential Injection System with Trapped Droplet Liquid-Liquid Extraction and Chemiluminescence Detection," Lab Chip, vol. 6, (2006), pp. 1387-1389.

Sherlock, Gavin, "Analysis of Large-Scale Gene Expression Data," Current Opinion in Immunology, vol. 12, (2000), pp. 201-205.

Shestopalov, Ilya, "Multi-step synthesis of nanoparticles performed on millisecond time scale in a microfluidic droplet-based system," Lab Chip, 2004, vol. 4, pp. 3-8.

Shestopalov, Ilya., et al., "Multi-Step Synthesis of Nanoparticles Performed on Millisecond Time Scale in a Microfluidic Droplet-Based System", Lab-Chip, 2004, vol. 4, pp. 316-321.

Shi, Weiwei et al., "Droplet-Based Microfluidic System for Individual Caenorhabditis Elegans Assay," Lab on a Chip, vol. 8, (2008), pp. 1432-1435.

Shih, Ie-Ming et al., "Evidence That Genetic Instability Occurs at an Early Stage of Colorectal Tumorigenesis," Cancer Research, vol. 61, (2001), pp. 818-822.

Shilov, alexander E. et al., "Activation of C—H Bonds by Metal Complexes," Chem. Rev., vol. 97, No. 8, (1997), pp. 2879-2932.

Shim, et al., "Control and Measurement of the Phase Behavior of Aqueous Solutions Using Microfluidics," Journal of the American Chemical Society, vol. 129, (2007), pp. 8825-8835.

Shim, Jung-uk et al., Simultaneous Determination of Gene Expression and Enzymatic Activity in Individual Bacterial Cells in Microdroplet Compartments, J. Am. Chem. Soc., vol. 131, (2009), pp. 15251-15256.

Shimazawa, Masamitsu et al., "A Novel Calpain Inhibitor, ((1S)-1-((((1S)-1-Benzyl-3 Cyclopropylamino-2, 3-dioxopropyl)amino)carbonyl)-3-methylbutyl)carbamic Acid 5-Methoxy-3-oxapentyl Ester (SNJ-1945), Reduces Murine Retinal Cell Death In Vitro and In Vivo," Journal of Pharmacology and Experimental Therapeutics, vol. 332, No. 2, (2010), pp. 380387.

Shumway, Robert H. et al., "Time Series Analysis and Its Applications With R Examples," Springer Science Business Media, LLC: New York, NY, 2006, 12p.

Sia, Samuel K. et al., "An Integrated Approach to a Portable and Low-Cost Immunoassay for Resource-Poor Settings" Angewandte Chemie-International Edition, vol. 43, pp. 498-502.

Sickmann, albert et al., "Towards a High Resolution Separation of Human Cerebrospinal Fluid," Journal of Chromatography B—Analytical Technologies in the Biomedical and Life Sciences, vol. 771, No. 1-2, (2002), pp. 167-196.

Sikes, Hadley D. et al., "Antigen Detection Using Polymerization-Based Amplification" Lab Chip, vol. 9, pp. 653-656.

Sikes, Hadley D. et al., "Using Polymeric Materials to Generate an Amplified Response to Molecular Recognition Events" Nature Materials, vol. 7, pp. 52-56.

Siman, Robert et al., "A Panel of Neuron-Enriched Proteins as Markers for Traumatic Brain Injury in Humans," Journal of Neurotrauma, vol. 26, No. 11, (2009), pp. 1867-1877.

Sindelka, Radek et al., "Intracellular Expression Profiles Measured by Real-Time PCR Tomography in the Xenopus Laevis Ooocyte," Nucleic Acids Research, vol. 36, No. 2, (2008), pp. 387-392.

Sista, Ramakrishna et al., "Development of a Digital Microfluidic Platform for Point of Care Testing," Lab Chip, vol. 8, (2008), pp. 2091-2104.

Sista, Ramakrishna et al., "Heterogeneous Immunoassays Using Magnetic Beads on a Digital Microfluidic Platform," Lab Chip, vol. 8, (2008), pp. 2188-2196.

Sohn, Kee-Sun et al., "Genetic algorithm—Assisted Combinatorial Search for a New Green Phosphor for Use in Tricolor White LEDs," J. Comb. Chem., vol. 8, (2006), pp. 44-49.

Sollier, Elodie et al., "Passive Microfluidic Devices for Plasma Extraction From Whole Human Blood," Sensors and Actuators B: Chemical, vol. 141 (2009), pp. 617-624 (2009).

Solomon, Sunil S. et al., "Dried Blood Spots (DBS): A Valuable Tool for HIV Surveillance in Developing/Tropical Countries," International Journal of STD & AIDS, vol. 13, (2002), pp. 2528.

Song, Helen et al., "Experimental Test of Scaling of Mixing by Chaotic Advection in Droplets Moving Through Microfluidic Channels," Applied Physics Letters, vol. 83, No. 22, (2003), pp. 4664-4666.

Song, Helen et al., "Millisecond Kinetics on a Microfluidic Chip Using Nanoliters of Reagents. Journal of the American Chemical Society," vol. 125, No. 47, (2003), pp. 14613-14619.

Song, Helen et al., "On-Chip Titration of an Anticoagulant Argatroban and Determination of the Clotting Time Within Whole Blood or Plasma Using a Plug-Based Microfluidic System," Analytical Chemistry, vol. 78, No. 14, (2006), pp. 4839-4849.

Song, Helen et al., "Reactions in Droplets in Microfluidic Channels," Angew. Chem. Int. Ed. vol. 45, (2006), pp. 7336-7356.

Souteyrand, Yves, P. et al., "Free Care at the Point of Service Delivery: a Key Component for Reaching Universal Access to HIV/AIDS Treatment in Developing Countries," AIDS, vol. 22, No. 1, (2008), S161-S168.

Spaid, Michael et al., "High Throughput Analysis Using Microemulsions for Reagent Encapsulation," 7th International Conference on Miniaturized Chemical and Biochemical Analysis Systems, Oct. 2003, pp. 445-448.

Spokoyny, alexander M. et al , "Infinite Coordination Polymer Nano- and Microparticle Structures," Chem. Soc. Rev., vol. 38, (2009), pp. 1218-1227.

Spurgeon, Sandra L. et al., "High Throughput Gene Expression Measurement with Real Time PCR in a Microfluidic Dynamic Array," PLoS ONE, vol. 3, Issue 2, (2008), pp. e1662.

Squires, Todd M. et al., "Microfluidics: Fluid Physics at the Nanoliter Scale," vol. 77, (2005), pp. 977-1026.

Stahl, Shannon S. et al., Homogeneous Oxidation of alkanes by Electrophili Late Transition Metals, Angew. Chem. Int. Ed., vol. 37, (1998), pp. 2180-2191.

Steegen, Kim et al., "Evaluation of Two Commercially Available alternatives for HIV-1 Viral Load Testing in Resource-Limited Settings," Journal of Virological Methods, vol. 146 (2007), pp. 178-187.

Sterne, Theodore E. "Some Remarks on Confidence or Fiducial Limits," Biometrika, vol. 41, No. 1/2 (1954), pp. 275-278.

Stoll, Monika et al., "A Genomic-Systems Biology Map for Cardiovascular Function," Science, vol. 294, No. 5547, (2001), pp. 1723-1726.

Story, Craig M. et al., "Profiling Antibody Responses by Multiparametric Analysis of Primary B Cells," PNAS, vol. 105, No. 46, (2008), pp. 17902-1790.

Stuart, Jeffrey N. et al., "The Chemistry of Thought: Neurotransmitters in the Brain," Analytical Chemistry, vol. 76, No. 7, (2004), pp. 120-128.

Sugiura, Shinji et al., "Interfacial Tension Driven Monodispersed Droplet Formation from Microfabricated Channel Array", Langmuir, 2001, vol. 17, pp. 5562-5566.

Sung, Wang Chou et al,, "Chip-based microfluidic devices coupled with electrospray ionization—mass spectrometry," Electrophoresis, 2005, vol. 26, pp. 1783-1791.

Szabo, Zsofia et al., "Voluntary Exercise May Engage Proteasome Function to Benefit the Brain After Trauma," Brain Research, vol. 1341, (2010) pp. 25-31.

Takats, Zoltan et al., "Ambient Mass Spectrometry Using Desorption Electrospray Ionization (DES!): Instrumentation, Mechanisms

(56) References Cited

OTHER PUBLICATIONS and Applications in Forensics, Chemistry, and Biology," Journal of Mass Spectrometry, vol. 40, No. 10, (2005), pp. 1261-1275.

Takeuchi, Shoji et al., "Controlling the Shape of Filamentous Cells of *Escherichia coli*," Nano Lett., vol. 5, No. 9 (2005), pp. 1819-1823.

Talasaz, Amirali H. et al., "Isolating Highly Enriched populations of Circulating Epithelial Cells and Other Rare Cells From Blood Using a Magnetic Sweeper Device". Proceedings of the National Academy of Sciences of the United States of America, vol. 106, (2009), pp. 39703975.

Tan, Swee Jin et al., "Microdevice for the Isolation and Enumeration of Cancer Cells From Blood". Biomedical Microdevices, vol. 11, (2009), pp. 883-892.

Tanaka, Hideo et al., "Ethanol Production from starch by a Coimmobilized Mixed Culture System of Aspergillus awamori and Zymomonas mobilis," Biotechnology and Bioengineering,1986, vol. XXVIII, pp. 1761-1768.

Taton, Andrew T. et al., "Scanometric DNA Array Detection with Nanoparticle Probes" Science, vol. 289, pp. 1757-1760.

Teh, Shia-Yen et al., "Droplet Microfluidics," Lab Chip, vol. 8 (2008), pp. 198-220.

Tharp, William G. et al., "Neutrophil Chemorepulsion in Defined Interleukin-8 Gradients in Vitro and in Vivo" Journal of Leukocyte Biology, vol. 79, (2006), pp. 539-554.

Theberge, Ashleigh B. et al., "Microdroplets in Microfluidics: An Evolving Platform for Discoveries in Chemistry and Biology," Angew. Chem. Int. Ed., 2010, vol. 49, pp. 5846-5868.

Thiel, Johannes et al., "Heteroatom-Controlled Kinetics of Switchable Polyoxometalate Frameworks," J. Am. Chem. Soc., vol. 131, (2009), pp. 4180-4181.

Thomas, Sydney et al., "Review of Ways to Transport Natural Gas Energy From Countries Which Do Not Need the Gas for Domestic Use," Energy, vol. 28, (2003), pp. 1461-1477.

Thorsen, Todd, et al., "Dynamic Pattern Formation in a Vesicle-Generating Microfluidic Device", Phys. Rev. Lett., 2001, vol. 86, No. 18, pp. 4163-4166.

Thorslund, Sara et al., "A Hybrid Poly(Dimethylsiloxane) Microsystem for On-Chip Whole Blood Filtration Optimized for Steroid Screening," Biomed Microdevices Biomed Microdevices, vol. 8, (2006), pp. 73-79.

Tice, Joshua et al., "Effects of Viscosity on Droplet Formation and Mixing in Microfluidic Channels," Analytica Chimica Acta, vol. 507, No. 1, (2004), pp. 73-77.

Tice, Joshua et al., "Formation of Droplets and Mixing in Multiphase Microfluidics at Low Values of the Reynolds and the Capillary Numbers," Langmuir, vol. 19, No. 22 (2003), pp. 9127-9133.

Titomanlio, G. et al., "Capillary Experiments of Flow Induced Crystallization of HDPE," AIChE Journal, Jan. 1990, vol. 36, No. 1, pp. 13-18.

Toh, Yi-Chin et al., "A Novel 3D Mammalian Cell Perfusion-Culture System in Microfluidic Channels," Lab Chip, No. 7, (2007), pp. 302-309.

Torkkeli, altti et al., "Droplet Manipulation on a Superhydrophobic Surface for Microchemical Analysis," The 11th International Conference on Solid-State Sensors and Actuators, Jun. 2001, 4 pages.

Tourovskaia, Anna et al., "Local Induction of Acetylcholine Receptor Clustering in Myotube Cultures Using Microfluidic Application of Agrin," Biophysical Journal, vol. 90, (2006), pp. 2192-2198.

Tranchemontagne,David J. et al., "Reticular Chemistry of Metal-Organic Polyhedra," Angew. Chem.-Int. Edit., vol. 47, (2008), pp. 5136-5147.

Tsigdinos,George A. et al., Molybdovanadophosphoric Acids and Their Salts, J Inorg. Chem., vol. 7, (1968), pp. 437-441.

Tucci, Sonia et al., "Glutamate Measured by 6-s Resolution Brain Microdialysis: Capillary Electrophoretic and Laser-Induced Fluorescence Detection Application," Journal of Chromatography B—Analytical Technologies in the Biomedical and Life Sciences, vol. 694, No. 2, (1997), pp. 343-349.

Tuteja, Anish et al., "Robust Omniphobic Surfaces," Proc. Natl. Acad. Sci. U. S. A., vol. 105, (2008), pp. 18200-18205.

Underhill, Gregory et al., "High-Throughput Analysis of Signals Regulating Stem Cell Fate and Function," Current Opinion in Chemical Biology, vol. 11, (2007), pp. 357-366.

Unger, Marc A. et al., "Monolithic Microfabricated Valves and Pumps by Multilayer Soft Lithography," Science, vol. 288, No. 5463 (2000), pp. 113-116.

Unknown author, "Extending the idea of using plugs for crystallization of proteins: screening and crystallization directly inside a capillary inside which the structure may be determined," protein_crystals_capillary_VD_1.FH10, 1 page.

Unknown author, "Extending the idea of using plugs for crystallization of proteins: screening and crystallization directly inside a capillary inside which the structure may be determined," protein_crystals_capillary_MB_1.FH10, 1 page.

Unknown Author, "HIV/AIDS Policy Fact Sheet," The Henry Kaiser Family Foundation, (Nov. 2009), 3p. http://www.kff.org/hivaids/upload/7029-05.pdf.

Unknown author, "Separating Nucleation and Growth," 8 slides.

Unknown Author, "The CCP4 Suite: Programs for Protein Crystallography", Acta Cryst (1994) D50, pp. 760-763.

Unknown Author, "The Global HIV Challenge: Assessing Progress, Identifying Obstacles, Renewing Commitment," UNAIDS Report on the Global Aids Epidemic, Executive Summary (2008).

Unknown Author, "Towards Universal Access—Scaling Up Priority HIV/AIDs Interventions in the Health Sector," WHO UNAIDS, Progress Report, 2009, 164 pages.

Urdea, Mickey et al., "Requirements for High Impact Diagnostics in the Developing World," vol. 444, Suppl 1, (2006), pp. 73-79.

Uttamchandani, Mahesh et al., "Small Molecule Microarrays: Recent Advances and Applications," Curr. Opin. Chem. Biol., vol. 9, (2005), pp. 4-13.

Uttayarat, Pimpon et al. "Topographic Guidance of Endothelial Cells on Silicone Surfaces with Micro- to Nanogrooves: Orientation of Actin Filaments and Focal Adhesions" Journal of Biomedical Materials Research Part A 75A, (2005), pp. 668-680.

Vagin, alexei et al., "MOLREP: An Automated Program for Molecular Replacement," J. Appl. Cryst., vol. 30, (1997), pp. 1022-1025.

Vail, J.H. et al., "Enumeration of Waterborne *Escherichia coli* With Petrifllm Plates: Comparison to Standard Methods," J. Environ. Qual., vol. 32, No. 1 (2003), pp. 368-373.

Valero, S. et al., "DoE Framework for Catalyst Development Based on Soft Computing Techniques," Comput. Chem. Eng., vol. 33, (2009), pp. 225-238.

Van Delinder, Virginia et al., "Separation of Plasma From Whole Human Blood in a Continuous Cross-Flow in a Molded Microfluidic Device," Anal. Chem., vol. 78, (2006), pp. 3765-3771.

Van Staden, J.F. "Membrane Separation in Flow Injection Systems," Fresenius J. Anal Chem. vol. 352, (1995), pp. 271-302.

Vandenabeele, Steven et al., "A Comprehensive Analysis of Hydrogen Peroxide-Induced Gene Expression in Tobacco," Proceedings of the National Academy of Sciences of the United States of America, vol. 100, No. 26 (2003), pp. 16113-16118.

Vargaftik, M.N. et al., "Highly Selective Partial Oxidation of Methane to Methyl Trifluoroacetate," J. Chem. Soc.—Chem. Commun.,(1990), pp. 1049-1050.

Villa-Diaz, Luis Gerardo et al., "Microfluidic Culture of Single Human Embryonic Stem Cell Colonies," Lab Chip, vol. 9, (2009), pp. 1749-1755.

Vozzi, Giovanni et al., "Fabrication of PLGA Scaffolds Using Soft Lithography and Microsyringe Deposition," Biomaterials, vol. 24, (2003), pp. 2533-2540.

Vozzi,G. et al., "Microsyringe-Based Deposition of Two-Dimensional and Three-Dimensional Polymer Scaffolds with a Well-Defined Geometry for Application to Tissue Engineering," Tissue Engineering, vol. 8, No. 6 (2002), pp. 1089-1098.

Vriamont, Nicolas et al., "Design of a Genetic algorithm for the Simulated Evolution of a Library of Asymmetric Transfer Hydrogenation Catalysts," Chem.-Eur. J., vol. 15, (2009), pp. 6267-6278.

(56) References Cited

OTHER PUBLICATIONS

Wages, S.A. et al., "Sampling Considerations for Online Microbore Liquid-Chromatography of Brain Dialysate," Analytical Chemistry, vol. 58, No. 8, (1986), pp. 1649-1656.
Walker, G. Terrance et al., "Strand Displacement Amplification—An Isothermal, In Vitro DNA Amplification Technique," Nucleic Acids Res., vol. 20, No. 7 (1992), pp. 1691-1696.
Walker, Glenn M. et al., "A Linear Dilution Microfluidic Device for Cytotoxicity Assays," Lab Chip, vol. 7, (2007), pp. 226-232.
Walt, David R., "Fibre Optic Microarrays," Chem. Soc. Rev., vol. 39, (2010), pp. 38-50.
Wang, Min et al., "Palladium—Silver Thin Film for Hydrogen Sensing (Sensors and Actuators" B: Chemical, vol. 123(1), (2007), pp. 101-106.
Wang, Qiangbin et al., "Photonic Interaction Between Quantum Dots and Gold Nanoparticles in Discrete Nanostructures through DNA Directed Self-Assembly," Chemical Communications, vol. 46, 2010, pp. 240-242.
Wang, Ying-Chih et al., "Million-Fold Preconcentration of Proteins and Peptides by Nanofluidic Filter," Analytical Chemistry, vol. 77, (2005), pp. 4293-4299.
Warden, Deborah, "*Military TBI During the Iraq and Afghanistan Wars*," J. Head Trauma Rehabil., vol. 21, No. 5, (2006), pp. 398-402.
Warren, Luigi et al., Transcription Factor Profiling in Individual Hematopoietic Progenitors by Digital RT-PCR, Proc. Natl. Acad. Sci. U. S. A., vol. 103, No. 47 (2006), pp. 17807-17812.
Watson, Christopher J. et al., In Vivo Measurements of Neurotransmitters by Microdialysis Sampling, Analytical Chemistry, vol. 78, No. 5, (2006), pp. 1391-1399.
Webb, Anna et al., "Guidance of Oligodendrocytes and Their Progenitors by Substratum Topography" Journal of Cell Science, vol. 108, (1995), pp. 2747-2760.
Weight, Ryan M. et al., "Photoacoustic Detection of Metastatic Melanoma Cells in the Human Circulatory System" Optics Letters, vol. 31, (2006), pp. 2998-3000.
Weinberg, David R. et al., "Competitive Oxidation and Protonation of Aqueous Monomethylplatinum(II) Complexes: A Comparison of Oxidants," Organometallics, vol. 26, (2007), pp. 167-172.
Weiss, David J. et al., "In Vivo Microdialysis as a Tool for Monitoring Pharmacokinetics," Trac-Trends in Analytical Chemistry, vol. 19, No. 10, (2000), pp. 606-616.
Wen, Ji-Kai et al., "A Visual DNA Chip for Simultaneous Detection of Hepatitis B Virus, Hepatitis C Virus and Human Immunodeficiency Virus Type-1" Biosensors & Bioelectronics, vol. 19, pp. 685-692.
Wheeler, M.B. et al., "Toward Culture of Single Gametes: The Development of Microfluidic Platforms for Assisted Reproduction" Theriogenology, vol. 68, (2007), S178-S189.
Wheeler, Rob C. et al., "Mesoscale Flow Chemistry: A Plug-Flow Approach to Reaction Optimisation," Org. Process Res. Dev., vol. 11, (2007), pp. 704-710.
Whitesides, George M. et al., "The Origins and the Future of Microfluidics," Nature, vol. 442, (2006), pp. 368-373.
Wismuller, Axel et al., "Cluster Analysis of Biomedical Image Time-Series" International Journal of Computer Vision, vol. 42, No. 2, (2002), pp. 103-128.
Wojcik, Barbara E. et al., "Traumatic Brain Injury Hospitalizations of US Army Soldiers Deployed to Afghanistan and Iraq," American Journal of Preventive Medicine, vol. 38, No. 1, (2010), pp. S108-S116.
Wolf, D. et al., "An Evolutionary Approach in the Combinatorial Selection and Optimizaiton of catalytic Materials," Appl. Catal. A-Gen., vol. 200, (2000), pp. 63-77.
Wong, Amy P. et al., "Partitioning Microfluidic Channels With Hydrogel to Construct Tunable 3-D Cellular Microenvironments," Science Direct Biomaterials, vol. 29, (2008), pp. 18531861.
Wong, Pak Kin et al., "Electrokinetic Biopressor for Concentrating Cells and Molecules," Anal. Chem., vol. 76, No. 23, (2004), pp. 6908-6914.

Woodward, R.L., "*How Probable is the Most Probable Number*" J. Am. Water Works As. vol. 49, (1957), pp. 1060-1068.
Wu, Liang, et al., "Droplet Formation in Microchannels Under Static Conditions," Appl. Phys. Lett. vol. 89, (2006), pp. 144106.
Xia, Younan et al., "Soft Lithography" Angewandte Chemie—International Edition, vol. 37, No. 5, (1998) pp. 551-575.
Xiong, Ye et al., "Emerging Treatments for Traumatic Brain Injury," Expert Opinion on Emerging Drugs, vol. 14, No. 1, (2009), pp. 67-84.
Yamanaka, Ichiro et al., "Oxidation of Methane and Benzene with Oxygen Catalyzed by Reduced Vanadium Species at 40° C.," J. Mol. Catal. A—Chem., vol. 133, (1998), pp. 251-254.
Yang, Jianing et al., "High Sensitivity PCR Assay in Plastic Micro Reactors," Lab Chip, vol. 2, (2002), pp. 179-187.
Yang, Liying et al., "Optimization of an Enrichment Process for Circulating Tumor Cells From the Blood of Head and Neck Cancer Patients Through Depletion of Normal Cells," Biotechnology and Bioengineering, vol. 102, No. 2, (2009), pp. 521-534.
Yang, Sung-Yi et al., "Microflow Cytometry Utilizing a Magnetic Bead-Based Immunoassay for Rapid Virus Detection," Biosensors and Bioelectronics, vol. 24, (2008), pp. 855-862.
Yeh, Chia-Hsien et al., "An Immunoassay Using Antibody-Gold Nanoparticle Conjugate, Silver Enhancement and Flatbed Scanner," Microfluidics and Nanofluidics, vol. 6, (2009), pp. 85-91.
Yeung, K.Y. et al., "Principal Component Analysis for Clustering Gene Expression Data," Bioinformatics, vol. 17, No. 9, (2001), pp. 763-774.
Younes-Metzler, Osnat et al., "Microfabricated High-Temperature Reactor for Catalytic Partial Oxidation of Methane," Applied Catalysis A: General, vol. 284, (2005), pp. 5-10.
Yu, Ji et al., "Probing Gene Expression in Live Cells, One Protein Molecule at a Time," Science, vol. 311, (2006), pp. 1600-1603.
Yuan, Yong J. et al., "Bond Rupture of Biomolecular Interactions by Resonant Quartz Crystal," Analytical Chemistry, vol. 79, (2007), pp. 9039-9044.
Yuen, Po Ki et al., "Microfluidic Devices for Fluidic Circulation and Mixing Improve Hybridization Signal Intensity on DNA Arrays," Lab Chip, vol. 3, (2003), pp. 46-50.
Zhang, Qingquan et al., "Microfluidic Droplet Trapping Array as Nanoliter Reactors for Gas-Liquid Chemical Reaction," Electrophoresis, vol. 30, No. 18, (2009), pp. 3181-3188.
Zhang, Xin et al., "New Triple Microbore Cannula System for Push-Pull Perfusion of Brain Nuclei of the Rat," Journal of Neuroscience Methods, vol. 32, (1990), pp. 93-104.
Zhang, Y.H. et al., "Microfluidic DNA Amplification—A Review," Analytica Chimica Acta, vol. 63, No. 2, (2009), pp. 115-125.
Zhang, Yi et al., "Putting the Invader Assay to Work: Laboratory Application and Data Management," Methods Mol. Biol., vol. 578, (2009), pp. 363-377.
Zhang, Zhiqun et al., Calpain-Mediated Collapsin Response Mediator Protein-1,-2, and-4 Proteolysis After Neurotoxic and Traumatic Brain Injury, Journal of Neurotrauma, vol. 24, No. 3, (2007), pp. 460-472.
Zheng, Bo et al., "A Droplet-Based, Composite PDMS/Glass Capillary Microfluidic system for Evaluating Protein Crystallization Conditions by Microbatch and Vapor-Diffusion Methods With On-Chip X-ray Diffraction," Angew. Chem. Int. Ed., vol. 43, (2004), pp. 2508-2511.
Zheng, Bo et al., "Formation of Arrayed Droplets of Soft Lithography and Two-Phase Fluid Flow, and Application in Protein Crystallization," Advanced Materials, vol. 16, No. 15, (2004), pp. 1365-1368.
Zheng, Bo et al., "Formation of Droplets of alternating Composition in Microfluidic Channels and Applications to Indexing of Concentrations in Droplet-Based Assays", Analytical Chemistry, 2004, vol. 76, pp. 4977-4982.
Zheng, Bo et al., "Screening of Protein Crystallization Conditions on a Microfluidic Chip Using Nanoliter-Size Droplets," J. Am. Chem. Soc., vol. 125, (2003), pp. 11170-11171.
Zheng, Bo et al., "Using Nanoliter Plugs in Microfluidics to Facilitate and Understand Protein Crystallization," Current Opinion in Structure Biology, vol. 15, (2005), pp. 548-555.

(56) References Cited

OTHER PUBLICATIONS

Zheng, Siyang et al., "Membrane Microfilter Device for Selective Capture, Electrolysis and Genomic Analysis of Human Circulating Tumor Cells," Journal of Chromatography A, vol. 1162, (2007), pp. 154-161.

Zhou, Xuechang et al., "Nanoliter Dispensing Method by Degassed Poly(dimethylsiloxand) Microchannels and Its Application in Protein Crystallization," Anal. Chem., vol. 79, No. 13, (2007), pp. 4924-4930.

Ziatdinov, Vadim R. et al., "Carboxylic Solvents and 0-Donor Ligand Effects on CH Activation by Pt(11)," J. Am. Chem. Soc., vol. 128, (2006), pp. 7404-7405.

Zieglschmid, V. et al., "Detection of Disseminated Tumor Cells in Peripheral Blood" Critical Reviews in Clinical Laboratory Sciences, vol. 42, (2005), pp. 155-196.

Zimmermann, Bernhard G. et al., "Digital PCR: A Powerful New Tool for Noninvasive Prenatal Diagnosis?" Prenatal Diagnosis, vol. 28, (2008), pp. 1087-1093.

Great Basin Corporation. Isothermal Amplification. Available at www.gbscience.com/technology/iso-amp. Accessed Jan. 6, 2014.

Great Basin Corporation. Sample-to-Result Molecular Diagnostics. Available at www.gbscience.com. Accessed Jan. 6, 2014.

Great Basin Corporation. Technology—Early appropriate treatment of infections is critical for good patient outcomes and to manage treatment costs. Available at www.gbscience.com/technology. Access Jan. 6, 2014.

International search report and written opinion dated May 10, 2010 for PCT Application No. PCT/U2010/28316.

Rea, et al. Point-of-Care Molecular Diagnostic Testing. Created Dec. 12, 2012 20:17. Published: Dec. 12, 2012. Published on IVD Technology. Available at http://www.ivdtechnology.com/print/3097. Accessed Jan. 6, 2014.

Office action dated Jul. 31, 2014 for U.S. Appl. No. 13/467,482.

Office action dated Aug. 15, 2014 for U.S. Appl. No. 13/257,811.

Office Action for U.S. Appl. No. 13/467,482, dated Jun. 16, 2015, 19 Pages.

Office Action for U.S. Appl. No. 14/177,190, dated Sep. 15, 2015, 24 Pages.

Official Notification for Israeli Patent Application No. 215160, dated Jul. 27, 2015, 4 Pages.

United States Office Action, U.S. Appl. No. 14/177,194, Apr. 26, 2016, 14 Pages.

US 7,897,368, 03/2011, Handique et al. (withdrawn)

\* cited by examiner

Figure 15

| Beacon design* | Fold fluorescence increase from no template control | | |
|---|---|---|---|
| | Negative Control | HIV mimic with expected sequence | HIV mimic with mutated (correct) sequence |
| V1<br>5'-F-CGATCGTGCAGAATGGGATAGATTGCGATCG-Q-3' | 0.89 | 4.5 | 4.1 |
| V2<br>5'-F-CGATCGTGCAGAATGGGATAGAGTGCGATCG-Q-3' | 0.95 | 1.6 | 3.7 |
| V3<br>5'-F-CGGATGCTGCAGAATGGGATAGAGTGCATCC-Q-3' | 1.08 | 40.2 | 44 |

* Fluorescein represented as F, and the Iowa Black quencher as Q. The region of the beacon that recognizes the HIV NASBA product is bold. The self hybridizing region of the hairpin is italicized. Changes from the original beacon design (V1) are emphasized with underlining. Values measured using NanoDrop 3300.

SEQUENCE LISTING

<160> NUMBER OF SEQ ID NOS: 14

<210> SEQ ID NO 1
<211> LENGTH: 23

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
caagatatga agtggtaaat ggt                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tttacgactt gttgcatacc atc                                              23

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
taatacgact cactataggg tgctatgtca cttccccttg gttctctca                  49

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gtggtgggat atcaagcagc catgcaaa                                         28

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-56-FAM
<220> FEATURE:
<223> OTHER INFORMATION: 3'-3IABkFQ

<400> SEQUENCE: 5
cggatgctgc agaatgggat acagtgcatc c                                     31

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagaaccaag gggaagtga                                                   19
```

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttaacattt gcatggctgc ttgat                                       25

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tattgcacca ggccagatga ttttgtacta gtagttcctg ctatg                 45

<210> SEQ ID NO 9
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cagcttcctc attgatggtc tcttttaaca ccatgctaaa cacagt                46

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
attatcagaa ggagccacc                                              19

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catcctattt gttcctgaag g                                           21

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein
<220> FEATURE:
<223> OTHER INFORMATION: 3'-Iowa Black quencher

<400> SEQUENCE: 12

```
cgatcgtgca gaatgggata gattgcgatc g                              31

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein
<220> FEATURE:
<223> OTHER INFORMATION: 3'-Iowa Black quencher

<400> SEQUENCE: 13
cgatcgtgca gaatgggata gagtgcgatc g                              31

<210> SEQ ID NO 14
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5'-Fluorescein
<220> FEATURE:
<223> OTHER INFORMATION: 3'-Iowa Black quencher

<400> SEQUENCE: 14
cggatgctgc agaatgggat agagtgcatc c                              31
```

ANALYSIS DEVICES, KITS, AND RELATED METHODS FOR DIGITAL QUANTIFICATION OF NUCLEIC ACIDS AND OTHER ANALYTES

CROSS-REFERENCE

This application is a continuation-in-part application of application Ser. No. 13/257,811, filed Sep. 20, 2011; which is the National Stage of International Application No. PCT/US2010/028316, filed on Mar. 23, 2010, which claims the benefit under 35 U.S.C. §119(e) of U.S. Provisional Application 61/262,375, filed on Nov. 18, 2009, and U.S. Provisional Application No. 61/162,922, filed on Mar. 24, 2009, and U.S. Provisional Application No. 61/340,872, filed on Mar. 22, 2010; this Application further claims the benefit of U.S. Provisional Application No. 61/516,628, filed Apr. 5, 2011 and U.S. Provisional Application No. 61/518,601, filed May 9, 2011; the content of all of which are hereby incorporated by reference in their entireties for any and all purposes.

STATEMENT OF GOVERNMENT RIGHTS

The United States Government has certain rights in this invention pursuant to Grant Nos. 1 R01 EB012946, GM074961, and DP1OD003584, awarded by the National Institutes of Health (NIH); and Grant No. CHE-0526693, awarded by the National Science Foundation.

SEQUENCE LISTING

The instant application contains a Sequence Listing which has been submitted in ASCII format via EFS-Web and is hereby incorporated by reference in its entirety. Said ASCII copy, created on May 24, 2012, is named Sequence_Listing_CRF_CTSC0093 and is 4,112 bytes in size.

TECHNICAL FIELD

The present application relates to the field of microfluidics and to the fields of detection and amplification of biological entities.

BACKGROUND

Existing methods for nucleic acid amplification and quantitative analysis include real-time polymerase chain reaction (PCR) and real-time reverse-transcription polymerase chain reaction (RT-PCR). Real-time methods are typically based on the detection of an exponential increase of fluorescence intensity and rapid thermal cycling between the dissociation temperature (~95° C.), annealing temperature (~50° C.), and synthesis temperature (~70° C.).

Digital PCR is another method for quantitative analysis of nucleic acids. By dividing a diluted sample into a large number of small-volume reaction compartments, single copies of nucleic acid template can be confined in isolated compartments and amplified by PCR. Only a "yes or no" readout is required, and the number of target molecules in the sample is determined by performing a statistical analysis on the number of "positive" and "negative" wells. This method transfers the exponential amplification profile into a linear, digital format. These digital PCR methods still require thermal cycling and accurate temperature control, both of which may be challenging to ensure in resource-limited field conditions. Accordingly, there is a need in the art for, inter alia, devices and methods for isothermal processes applicable to detection and even quantification of one or more analytes. The value of such devices and methods would be further enhanced if the devices and methods were in at least some embodiments, manually portable.

SUMMARY

In meeting the described challenges, the present disclosure first provides methods, the methods comprising: effecting relative motion between a first substrate and a second substrate, the first substrate having a first population of wells formed therein, the second substrate having a second population of wells formed therein, the relative motion between the first and second substrates giving rise to at least some wells of the first population of wells being placed into fluid communication with at least some wells of the second population of wells; and effecting contact between a first material disposed within at least some of the first population of wells and a second material disposed within at least some of the second population of wells.

The present disclosure also provides methods, the methods comprising inducing relative motion between a first substrate and a second substrate so as to dispose a first material into first and second populations of wells formed in at least one of the substrates; inducing relative motion between the first and second substrates so as to dispose a second material into third and fourth populations of wells formed at least one of the substrates, the first and second materials being contacted to one another.

Further provided are devices. These devices (as well as those devices described in the priority documents) may be referred to as SlipChip™ brand devices. In some embodiments, the device suitably comprising a first substrate having a first population of wells formed therein, at least one well of the first population of wells having at least one satellite well disposed proximate to the at least one well, the at least one satellite well being adapted to retain material from the at least one well; a second substrate having a second plurality of wells formed therein, the first and second substrates being slidably engagable with one another such that relative motion between the first and second substrates places at least some of the first population of wells in register with at least some of the second population of wells so as to form combined reaction chambers. The devices presented in the present disclosure may be of such a size that they are manually portable. For example, a device may define a cross-sectional dimension (e.g., height, width, thickness) that is in the range of 1 mm to about 1 cm, to about 5 cm, to about 10 cm, or even to about 50 cm. The disclosed devices may be larger than the foregoing.

Additionally disclosed are kits. The disclosed kits suitably include a first substrate having a first population of wells formed therein; a second substrate having a second population of wells formed therein, the first and second substrates being superposable and slidably engagable with one another such that relative motion between the substrates places at least some of the first population of wells into fluid communication with at least some of the second population of wells; and a supply of at least one reagent adapted to participate in amplification of nucleic acid.

Also provided are methods. The methods suitably include amplifying a nucleic acid molecule, comprising contacting (a) a sample comprising at least one nucleic acid molecule disposed at a plurality of first areas, with (b) at least one component of an amplification reagent disposed in a plurality of second areas, the contacting being effected by placing the first and second areas into direct fluid communication with one another; and the contacting comprises effecting relative motion between a substrate comprising the first area with a substrate comprising the second area; and exposing the area having the at least one nucleic acid molecule to conditions effective for amplification of the at least one nucleic acid molecule.

The present disclosure also provides devices. The devices suitably include a first substrate having a first population of areas, at least one area of the first population of areas having at least one satellite area disposed proximate to the at least one area, the at least one satellite area being adapted to retain material from the at least one area; a second substrate having a second plurality of area formed therein, the first and second substrates being engagable with one another such that relative motion between the first and second substrates places at least some of the first population of areas in register with at least some of the second population of areas so as to place the first and second areas into fluid communication with one another.

Additionally provided are methods of effecting amplification of at least one nucleic acid target molecule. These methods suitably include contacting (1) a sample material disposed in a plurality of first areas, the sample material comprising a nucleic acid target, and at least one of the first areas containing one molecule of the nucleic acid target, with (2) a reactant material disposed in a plurality of second areas, the contacting being effected by pairwise placement of at least some of the first areas and at least some of the second areas into direct fluid communication with one another, the contacting effecting amplification of at least one nucleic acid target molecule.

Further provided are methods, the methods suitably comprising dispersing a first sample that comprises at least one molecule of interest among a plurality of first areas, at least one of the first areas containing a single molecule of interest; dispersing a reactant material into a plurality of second areas; and effecting pairwise placement of at least some of the plurality of first areas into direct fluid communication with at least some of the plurality of second areas so as to contact reactant material with the first sample.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 15 is a table summary of beacon design (SEQ ID NOS 12-14, respectively, in order of appearance) and signal increase to the NASBA product of HIV;

DETAILED DESCRIPTION OF ILLUSTRATIVE EMBODIMENTS

Figure 1:
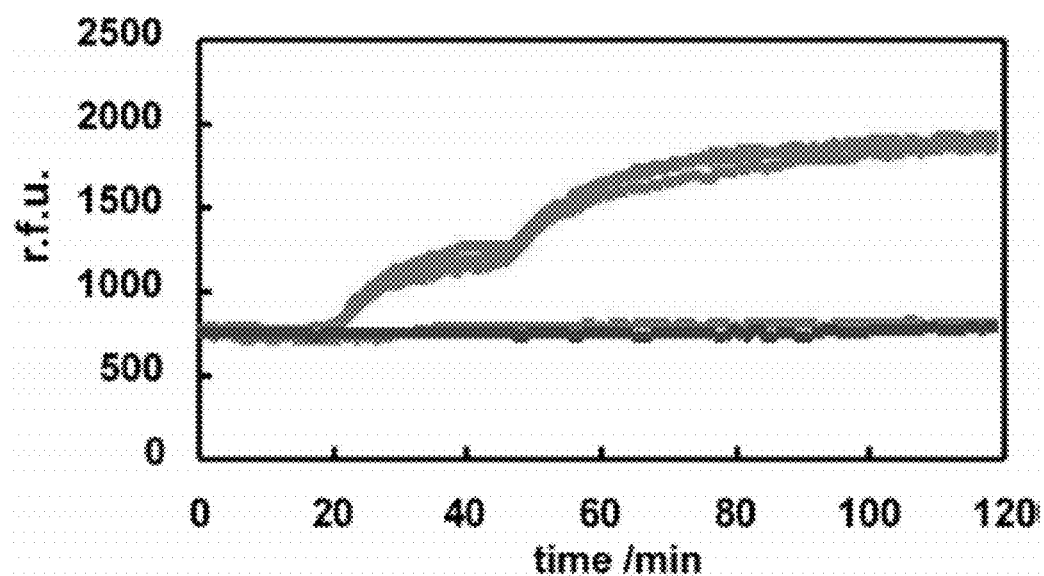
FIG. 1 illustrates RPA amplification of MRSA genomic DNA (5 pg/11 L) in a well plate at 25° C.

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms a, an, and the include the plural, and reference to a particular numerical value includes at least that particular value, unless the context clearly dictates otherwise.

The term plurality as used herein, means more than one. When a range of values is expressed, another embodiment includes from the one particular value and/or to the other particular value. Similarly, when values are expressed as approximations, by use of the antecedent about, it will be understood that the particular value forms another embodiment. All ranges are inclusive and combinable. Any documents cited herein are incorporated herein by reference in their entireties for any and all purposes.

Certain description herein refers to "areas." It should be understood that the term "area" refers to a site where two or more materials may be contacted with one another. The term may also refer to a region that maintains a material thereon, therealong, or therein. An "area" may take on a physical structure such as a hole, well, cavity, or indentation, and may also have any cross-sectional shape along its length, width, or depth, such as rectangular, circular, or triangular. An area may also be a region of a substrate, which region may include a treatment to render it hydrophilic or hydrophobic.

For convenience and also for purposes of ease of illustration, a number of exemplary embodiments provided herein describe areas by illustrating areas with well structures. Such description and illustration should not be taken as limiting the scope of the present disclosure to embodiments that feature wells, as the disclosed devices and methods may be applied to any one or more of the various types of areas described above. The term "wells" should be understood as being representative of "areas," and that other types of areas may be used in place of the "wells" used to illustrate an exemplary embodiment.

In a first aspect, the present disclosure provides methods. The methods suitably include effecting relative motion between a first substrate and a second substrate. The first substrate suitably has a first population of wells formed therein, and the second substrate suitably has a second population of wells formed therein.

It should be understood that a substrate may have multiple populations of areas (e.g., wells) formed therein. As one example, the first substrate may include one population of wells that are placed into fluid communication with one another by way of a first conduit formed in the substrate, the conduit being configured to allow filling of the wells from a source exterior to the substrate (e.g., FIG. 2). The first substrate may include another population of wells that is not in fluid communication with the first population of wells. This other population of wells may be placed into fluid communication with one another by way of a conduit formed in the substrate, or the wells may be formed in the substrate without connection to the environment exterior to the substrate.

The first and second substrate may be configured such that relative motion between the first and second substrates gives rise to at least some wells of the first population of wells being placed into fluid communication with at least some wells of the second population of wells. This relative motion may be referred to in some places for convenience as "slipping," and may refer to linear motion (as shown in exemplary FIG. 2), but may also to rotational motion or other non-linear movement. The relative motion may be effected manually, or by mechanical or other automated means.

The methods also suitably include effecting contact between a first material disposed within at least some of the first population of wells and a second material disposed within at least some of the second population of wells. This contact may be effected, for example, by placing a well of the first population into fluid communication with a well of the second population, as shown in exemplary FIG. 2, where placing two wells into fluid communication with one another effects contact between the two fluids. It should be understood that materials disposed within the wells are not limited to liquids, as solid materials (e.g., dried reagents) and even gases may be disposed within the wells of the disclosed devices.

In some embodiments, the user may introduce the first material into a population of wells by exerting the one or more materials into a conduit formed in the second substrate, the conduit being in fluid communication with the first population of wells. This is illustrated in exemplary FIG. 2 and FIG. 6, which show introduction of a material via a conduit into a population of wells of a substrate. Similarly, a user may introduce the second material into the second population of wells by exerting the one or more materials into a conduit formed in the second substrate, the conduit being in fluid communication with the second population of wells. A user may also dispose a material into a well by dripping, pipetting, vapor deposition, and the like; introduction of material into a well is not limited to doing so by way of conduits. A user may use a device (pipette, syringe, and the like) that is adapted to engage with a conduit formed in the device.

In some embodiments, at least some of the first material remains uncontacted with the second material. Some of the second material may also remain uncontacted with the first material. This may be done to create control wells for a given experiment or analysis.

The methods may also include amplifying one or more nucleic acids present within the first population of wells, the second population of wells, or both. A variety of amplification techniques are known in the field; amplification techniques that are performed essentially isothermally are considered especially suitable. By isothermal is meant a reaction that involves fewer than 10 changes in temperature. It should be understood that although isothermal techniques are particularly useful, the present disclosure is not limited to isothermal amplification. A non-exclusive listing of suitable amplification techniques includes loop-mediated amplification, nucleic acid sequence based amplification, recombinase polymerase amplification, rolling circle amplification, helicase-dependent amplification, transcription-mediated amplification, multiple displacement amplification, strand-displacement amplification, and the like. An exemplary listing of amplification techniques is provided in application PCT/US2010/028316, the entirety of which is incorporated herein by reference. Combinations of techniques may be used. For example, one set of wells may be used in the amplification of nucleic acids by a first technique, and a separate set of wells may be used in the amplification of nucleic acids by a second technique.

A non-exclusive listing of suitable isothermal amplification techniques are provided below. These techniques are illustrative only, and do not limit the present disclosure.

A first set of suitable isothermal amplification technologies includes NASBA, and RT-RPA. These amplification techniques can operate at 40 deg. C. (a lower temperature preferred for certain POC devices): NASBA (product: RNA), RT-RPA (product: DNA), RT-LAMP using one of LAMP HIV-RNA 6-primer sets, transcription-mediated amplification (TMA, 41 deg. C.), helicase dependent amplification (HAD, 65 deg. C.), and strand-displacement amplification (SDA, 37 deg. C.), In addition to standard PCR techniques, the disclosed methods and devices are compatible with isothermal amplification techniques such as loop-mediated amplification (LAMP), Recombinase polymerase amplification (RPA), nucleic acid sequence based amplification (NASBA), transcription-mediated amplification (TMA), helicase-dependent amplification (HAD), rolling circle amplification (RCA), and strand-displacement amplification (SDA). The multivolume SlipChip can be used to digitize such platforms.

Other isothermal amplification methods are also suitable. Isothermal exponential amplification reaction (EXPAR) can amplify a 10-20 bp trigger oligonucleotide generated from a genomic target more than 106 times in less than 10 minutes at 55 deg. C. by repeating cycles of polymerase and endonuclease activity, and has been coupled with DNA-functionalized gold nanospheres for the detection of herpes simplex virus. Isothermal and chimeric primer-initiated amplification of nucleic acids (ICANs) amplify target DNA at 55 deg. C. using a pair of 50-DNA-RNA-30 primers and the activity of RNase H and strand displacing polymerase.

Signal-mediated amplification of RNA technology (SMART) produces copies of an RNA signal at 41 deg. C. in the presence of an RNA or DNA target by way of the three-way junction formed between the target and two probes, one of which contains the RNA signal sequence and a T7 promoter sequence for T7 RNA polymerase. The single stranded RNA product may be detected by hybridization-based methods and because the signal is independent of the target, SMART can be easily adapted for detection of different target sequences. Cyclic enzymatic amplification method (CEAM) detects nucleic acids in the picomolar range in less than 20 minutes at 37 deg. C. using a displacing probe and Exonuclease III (Exo III) to generate amplification of fluorescent signal in the presence of a target. Isothermal target and signaling probe amplification (iTPA) combines the principle of ICAN and the inner-outer probe concept of LAMP along with fluorescence resonance energy transfer cycling probe technology (FRET CPT) for simultaneous target and signal amplification in 90 minutes at 60 deg. C., and has been shown to detect *Chlamydia trachomatis* at single copy level.

Other suitable amplification methods include ligase chain reaction (LCR); amplification methods based on the use of Q-beta replicase or template-dependent polymerase; helicase-dependent isothermal amplification; strand displacement amplification (SDA); thermophilic SDA nucleic acid sequence based amplification (3SR or NASBA) and transcription-associated amplification (TAA).

Non-limiting examples of PCR amplification methods include standard PCR, AFLP-PCR, Allele-specific PCR, Alu-PCR, Asymmetric PCR, Biased Allele-Specific (BAS) Amplification, Colony PCR, Hot start PCR, Inverse PCR (IPCR), In situ PCR (ISH), Intersequence-specific PCR (ISSR-PCR), Long PCR, Multiplex PCR, Nested PCR, Quantitative PCR, Reverse Transcription PCR(RT-PCR), Real Time PCR, Single cell PCR, Solid phase PCR, Universal Size-Specific (USS-PCR), branched-DNA technology, and the like A variety of specific amplification techniques are described below. Each of these techniques is suitably performed by the disclosed devices and methods. Allele-specific PCR is a diagnostic or cloning technique based on single-nucleotide polymorphisms (SNPs) (single-base differences in DNA). It requires some knowledge of a DNA sequence, including differences between alleles, and uses primers whose 3' ends encompass the SNP. PCR amplification may be less efficient in the presence of a mismatch between template and primer, so successful amplification with an SNP-specific primer signals presence of the specific SNP in a sequence.

Assembly PCR or Polymerase Cycling Assembly (PCA) is an artificial synthesis of long DNA sequences by performing PCR on a pool of long oligonucleotides with short overlapping segments. The oligonucleotides alternate between sense and antisense directions, and the overlapping segments determine the order of the PCR fragments, thereby selectively producing the final long DNA product.

Asymmetric PCR preferentially amplifies one DNA strand in a double-stranded DNA template. It is used in sequencing and hybridization probing where amplification of only one of the two complementary strands is required. PCR is carried out as usual, but with a great excess of the primer for the strand targeted for amplification. Because of the slow (arithmetic) amplification later in the reaction after the limiting primer has been used up, extra cycles of PCR are required. A recent modification on this process, known as Linear-After-The-Exponential-PCR (LATE-PCR), uses a limiting primer with a higher melting temperature (Tm) than the excess primer to maintain reaction efficiency as the limiting primer concentration decreases mid-reaction.

Helicase-dependent amplification is similar to traditional PCR, but uses a constant temperature rather than cycling through denaturation and annealing/extension cycles. DNA helicase, an enzyme that unwinds DNA, is used in place of thermal denaturation.

Hot start PCR is a technique that reduces non-specific amplification during the initial set up stages of the PCR. It may be performed manually by heating the reaction components to the denaturation temperature (e.g., 95° C.) before adding the polymerase. Specialized enzyme systems have been developed that inhibit the polymerase's activity at ambient temperature, either by the binding of an antibody or by the presence of covalently bound inhibitors that dissociate only after a high-temperature activation step. Hot-start/cold-finish PCR is achieved with new hybrid polymerases that are inactive at ambient temperature and are instantly activated at elongation temperature.

Intersequence-specific PCR (ISSR) is a PCR method for DNA fingerprinting that amplifies regions between simple sequence repeats to produce a unique fingerprint of amplified fragment lengths.

Inverse PCR is commonly used to identify the flanking sequences around genomic inserts. It involves a series of DNA digestions and self ligation, resulting in known sequences at either end of the unknown sequence.

Ligation-mediated PCR: uses small DNA linkers ligated to the DNA of interest and multiple primers annealing to the DNA linkers; it has been used for DNA sequencing, genome walking, and DNA footprinting.

Methylation-specific PCR (MSP) is used to detect methylation of CpG islands in genomic DNA. DNA is first treated with sodium bisulfate, which converts unmethylated cytosine bases to uracil, which is recognized by PCR primers as thymine Two PCRs are then carried out on the modified DNA, using primer sets identical except at any CpG islands within the primer sequences. At these points, one primer set recognizes DNA with cytosines to amplify methylated DNA, and one set recognizes DNA with uracil or thymine to amplify unmethylated DNA. MSP using qPCR can also be performed to obtain quantitative rather than qualitative information about methylation.

Miniprimer PCR uses a thermostable polymerase (S-Tbr) that can extend from short primers ("smalligos") as short as 9 or 10 nucleotides. This method permits PCR targeting to smaller primer binding regions, and is used to amplify conserved DNA sequences, such as the 16S (or eukaryotic 18S) rRNA gene.

Multiplex Ligation-dependent Probe Amplification (MLPA) permits multiple targets to be amplified with only a single primer pair, as distinct from multiplex-PCR.

Multiplex-PCR: consists of multiple primer sets within a single PCR mixture to produce amplicons of varying sizes that are specific to different DNA sequences. By targeting multiple genes at once, additional information may be gained from a single test-run that otherwise would require several times the reagents and more time to perform. Annealing temperatures for each of the primer sets must be optimized to work correctly within a single reaction, and amplicon sizes. That is, their base pair length should be different enough to form distinct bands when visualized by gel electrophoresis.

Nested PCR: increases the specificity of DNA amplification, by reducing background due to non-specific amplification of DNA. Two sets of primers are used in two successive PCRs. In the first reaction, one pair of primers is used to generate DNA products, which besides the intended target, may still consist of non-specifically amplified DNA fragments. The product(s) are then used in a second PCR with a set of primers whose binding sites are completely or partially different from and located 3' of each of the primers used in the first reaction. Nested PCR is often more successful in specifically amplifying long DNA fragments than conventional PCR, but it requires more detailed knowledge of the target sequences.

Overlap-extension PCR or Splicing by overlap extension (SOE): a genetic engineering technique that is used to splice together two or more DNA fragments that contain complementary sequences. It is used to join DNA pieces containing genes, regulatory sequences, or mutations; the technique enables creation of specific and long DNA constructs.

Quantitative PCR (Q-PCR): used to measure the quantity of a PCR product (commonly in real-time). It quantitatively measures starting amounts of DNA, cDNA, or RNA. Q-PCR is commonly used to determine whether a DNA sequence is present in a sample and the number of its copies in the sample. Quantitative real-time PCR can have a high degree of precision. QRT-PCR (or QF-PCR) methods use fluorescent dyes, such as Sybr Green, EvaGreen or fluorophore-containing DNA probes, such as TaqMan, to measure the amount of amplified product in real time. It is also sometimes abbreviated to RT-PCR (Real Time PCR) or RQ-PCR. QRT-PCR or RTQ-PCR are more appropriate contractions, since RT-PCR commonly refers to reverse transcription PCR (see below), often used in conjunction with Q-PCR.

Reverse Transcription PCR (RT-PCR): for amplifying DNA from RNA. Reverse transcriptase reverse transcribes RNA into cDNA, which is then amplified by PCR. RT-PCR is widely used in expression profiling, to determine the expression of a gene or to identify the sequence of an RNA transcript, including transcription start and termination sites. If the genomic DNA sequence of a gene is known, RT-PCR can be used to map the location of exons and introns in the gene. The 5' end of a gene (corresponding to the transcription start site) is typically identified by RACE-PCR (Rapid Amplification of cDNA Ends).

Solid Phase PCR: encompasses multiple meanings, including Polony Amplification (where PCR colonies are derived in a gel matrix, for example), Bridge PCR[32] (primers are covalently linked to a solid-support surface), conventional Solid Phase PCR (where Asymmetric PCR is applied in the presence of solid support bearing primer with sequence matching one of the aqueous primers) and Enhanced Solid Phase PCR (where conventional Solid Phase PCR can be improved by employing high Tm and nested solid support primer with optional application of a thermal 'step' to favour solid support priming).

Thermal asymmetric interlaced PCR (TAIL-PCR) may be useful for isolation of an unknown sequence flanking a known sequence. Within the known sequence, TAIL-PCR uses a nested pair of primers with differing annealing temperatures; a degenerate primer is used to amplify in the other direction from the unknown sequence.

Touchdown PCR (Step-down PCR) is a variant of PCR that aims to reduce nonspecific background by gradually lowering the annealing temperature as PCR cycling progresses. The annealing temperature at the initial cycles is usually a few degrees (3-5° C.) above the Tm of the primers used, while at the later cycles, it is a few degrees (3-5° C.) below the primer Tm. The higher temperatures give greater specificity for primer binding, and the lower temperatures permit more efficient amplification from the specific products formed during the initial cycles.

PAN-AC uses isothermal conditions for amplification, and may be used in living cells.

Universal Fast Walking is useful for genome walking and genetic fingerprinting using a more specific 'two-sided' PCR than conventional 'one-sided' approaches (using only one gene-specific primer and one general primer—which can lead to artefactual 'noise') by virtue of a mechanism involving lariat structure formation. Streamlined derivatives of UFW are LaNe RAGE (lariat-dependent nested PCR for rapid amplification of genomic DNA ends), 5'RACE LaNe, and 3'RACE LaNe.

COLD-PCR (co-amplification at lower denaturation temperature-PCR) is a modified Polymerase Chain Reaction (PCR) protocol that enriches variant alleles from a mixture of wildtype and mutation-containing DNA.

An alternative isothermal amplification and detection method that is isothermal in nature is described at http://www.invaderchemistry.com/ (Invader Chemistry). This method may be performed by the disclosed devices and methods. Another alternative amplification technique (so-called qPCR) is disclosed by MNAzyme (http://www.speed-x.com.au/MNAzymeqPCR.html), which technique is also suitable for the presently disclosed devices and methods.

One may also effect amplification based on nucleic acid circuits (which circuits may be enzyme-free). The following references (all of which are incorporated herein by reference in their entireties) describe exemplary circuits; all of the following are suitable for use in the disclosed devices and methods: Li et al., "Rational, modular adaptation of enzyme-free DNA circuits to multiple detection methods," Nucl. Acids Res. (2011) doi: 10.1093/nar/gkr504; Seelig et al., "Enzyme-Free Nucleic Acid Logic Circuits," Science (Dec. 8, 2006), 1585-1588; Genot et al, "Remote Toehold: A Mechanism for Flexible Control of DNA Hybridization Kinetics," JACS 2011, 133 (7), pp 2177-2182; Choi et al., "Programmable in situ amplification for multiplexed imaging of mRNA expression," Nature Biotechnol, 28:1208-1212, 2010; Benner, Steven A., and A. Michael Sismour. "Synthetic Biology." *Nat Rev Genet.* 6, no. 7 (2005): 533-543; Dirks, R. M., and N. A. Pierce. "Triggered Amplification by Hybridization Chain Reaction." *Proceedings of the National Academy of Sciences of the United States of America* 101, no. 43 (2004): 15275; Graugnard, E., A. Cox, J. Lee, C. Jorcyk, B. Yurke, and W. L. Hughes. "Kinetics of DNA and Rna Hybridization in Serum and Serum-Sds." *Nanotechnology, IEEE Transactions on* 9, no. 5 (2010): 603-609; Li, Bingling, Andrew D. Ellington, and Xi Chen. "Rational, Modular Adaptation of Enzyme-Free DNA Circuits to Multiple Detection Methods." *Nucleic Acids Research*, (2011); Li, Q., G. Luan, Q. Guo, and J. Liang. "A New Class of Homogeneous Nucleic Acid Probes Based on Specific Displacement Hybridization." *Nucleic Acids Research* 30, no. 2 (2002): e5-e5; Picuri, J. M., B. M. Frezza, and M. R. Ghadiri. "Universal Translators for Nucleic Acid Diagnosis." *Journal of the American Chemical Society* 131, no. 26 (2009): 9368-9377; Qian, Lulu, and Erik Winfree. "Scaling up Digital Circuit Computation with DNA Strand Displacement Cascades." *Science* 332, no. 6034 (2011): 1196-1201; Tsongalis, G. J. "Branched DNA Technology in Molecular Diagnostics." *American journal of clinical pathology* 126, no. 3 (2006): 448-453; Van Ness, Jeffrey, Lori K. Van Ness, and David J. Galas. "Isothermal Reactions for the Amplification of Oligonucleotides." *Proceedings of the National Academy of Sciences* 100, no. 8 (2003): 4504-4509; Yin, Peng, Harry M. T. Choi, Colby R. Calvert, and Niles A. Pierce. "Programming Biomolecular Self-Assembly Pathways." *Nature* 451, no. 7176 (2008): 318-322; Zhang, D. Y., and E. Winfree. "Control of DNA Strand Displacement Kinetics Using Toehold Exchange." *Journal of the American Chemical Society* 131, no. 47 (2009): 17303-17314; Zhang, David Yu, Andrew J. Turberfield, Bernard Yurke, and Erik Winfree. "Engineering Entropy-Driven Reactions and Networks Catalyzed by DNA." *Science* 318, no. 5853 (2007): 1121-1125; Zhang, Z., D. Zeng, H. Ma, G. Feng, J. Hu, L. He, C. Li, and C. Fan. "A DNA-Origami Chip Platform for Label-Free SNP Genotyping Using Toehold-Mediated Strand Displacement." *Small* 6, no. 17 (2010): 1854-1858.

In some embodiments, the one or more nucleic acids may reside on a label bound to a protein. This may be applied in immuno-amplification techniques, as described elsewhere herein, which techniques enable detection and quantification of proteins.

In certain embodiments of the disclosed technology, at least one well of the first population of wells, the second population of wells, or both, is disposed proximate to a satellite well. Such a satellite well is suitably adapted to retain material from the at least one well. This is illustrated in, e.g., non-limiting FIG. 2 and FIG. 6, which show shows satellite wells disposed proximate to the Type II wells shown in the figure. The satellite wells may be used to retain material that may exit another well, e.g., as a result of thermal expansion.

The relative motion between the first and second substrates places at least some of the first population of wells in register with at least some of the second population of wells so as to form combined reaction chambers. This is shown in illustrative FIG. 2 and FIG. 6, which show formation of such reaction chambers resulting from the registry between Type I and Type II wells. The relative motion may give rise to 1, 10, 100, 1000, 10,000, or even more such reaction chambers on a substrate or even within a device. As one example, the relative motion between two substrates may pairwise place about 10 first areas (e.g., wells) into direct fluid communication (e.g., by placing into register) with 10 second areas. The relative motion may pairwise place about 50, 100, or even 1000 first areas into direct fluid communication with 50, 100, or even 1000, respectively, second areas.

Wells formed on a substrate may have comparatively small volumes, e.g., about 0.1, 1, 5, 10, 50, 100, or even about 1000 nL per well. A substrate may include wells of two or more volumes, and given, discrete population of wells (e.g., a set of wells that are in fluid communication with a conduit formed in the substrate in which the wells reside) may include wells of two or more volumes.

In other embodiments, the present disclosure provides methods, the methods including inducing relative motion between a first substrate and a second substrate so as to dispose a first material into first and second populations of wells formed in at least one of the substrates; inducing relative motion between the first and second substrates so as to dispose a second material into third and fourth populations of wells formed at least one of the substrates, the first and second materials being contacted to one another.

In some embodiments, the user may introduce the first material to at least one well by exerting the material through a conduit in fluid communication with the well. The user may also introduce the second material to at least one well by exerting the material through a conduit in fluid communication with the well.

Figure 2:
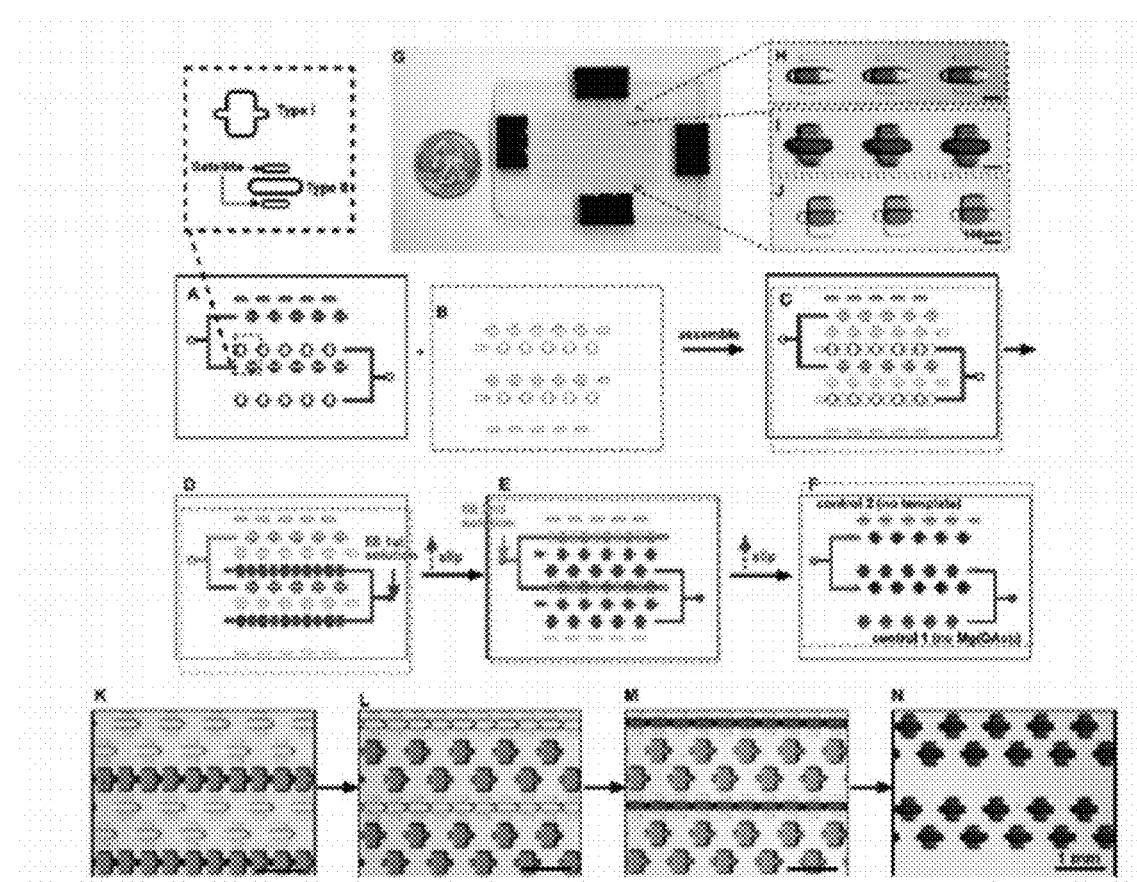
FIG. 2 illustrates a schematic drawing of a two-step device for digital RPA.

As described elsewhere herein, at least some of the first material may remain uncombined with the second material. Likewise, at least some of the second material may remain uncombined with the first material. This is shown in FIG. 2, which figure shows control wells that do not contain mixed materials.

The user may also amplify one or more nucleic acids present within a population of wells. Such amplification may be effected with temperature cycling; isothermal methods of amplification are considered especially suitable. Suitable methods of amplification are described elsewhere herein. Suitable well and substrate configurations—including satellite wells—are described elsewhere herein.

It should be understood that the present disclosure is not limited to isothermal processes, and that the disclosed devices and methods may be adapted to effect other molecular reactions, including single-molecule reactions. For example, a sample may be introduced to a first set of compartments such that at least one well contains (or is estimated to contain) only a single molecule of sample. The sample may be undergo a reaction (e.g., labeling, neutralizing, acidification, digestion, ligation, translation, transcription, reverse transcription, crystallization, incubation, dissolution, detection and the like) in that first set of compartments. With specific regard to detection reactions, the detection reaction may include molecular beacons, sequencing, enzymatic reactions, fluorogenic reactions, colorimetric reactions, and the like. The detection methods provided in priority application PCT/US2010/028316 (incorporated herein in its entirety) are suitable for the disclosed devices and methods.

The user may effect relative motion between that first set of compartments and a second set of compartments that contains a particular reagent so as to place the first and second sets of compartments into register and direct fluid communication with one another. The material (i.e., reacted sample) in the first set of wells then contacts the reagent in the second set of wells, and the reacted sample may then react with the reagent in the second set of wells. In some embodiments, this reaction may be an amplification reaction, or labeling, neutralizing, acidification, digestion, ligation, translation, transcription, reverse transcription, crystallization, incubation, dissolution, and the like. The reaction may also be a detection reaction. Accordingly, as described above, a given sample that resides in a first set of compartments may undergo multiple, sequential reactions as the sample is exposed to other reagents by way of relative motion between the compartment(s) in which the sample is disposed and other compartments that contain other reagents. This in turn enables effecting sequential processing on multiple sample compartments in parallel.

Some embodiments of the devices and methods disclosed here provide for amplification of nucleic acids, followed by recovery of the amplified material. Such recovery may be carried out, in some embodiments, by accessing individual wells of a device. In some embodiments, recovery may be achieved by combining material from multiple wells, for example by slipping a device to the loading position and using a carrier fluid to expel the material from the device. Such recovery may be used for additional analysis of nucleic acids, such as sequencing, genotyping, analysis of methylation patterns, and identification of epigenetic markers. In some embodiments, recovered material may be removed from the device. In some embodiment, recovered material may be transferred to another device, or another region of the same device. Amplification may be carried out by the methods described herein or by other methods known in the art or by their combinations.

Figure 14:
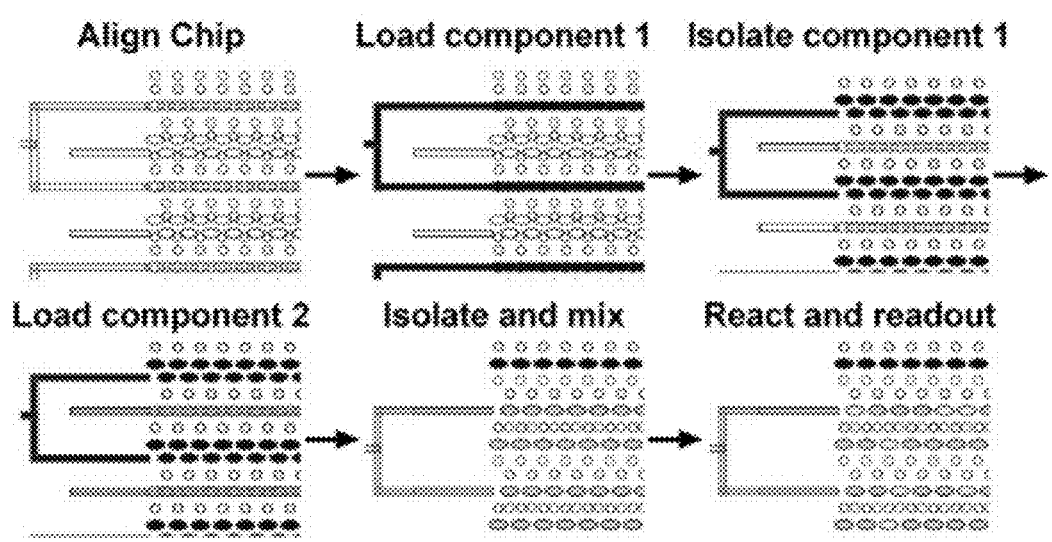
FIG. 14 illustrates a schematic of an exemplary two-stage device design. The design includes 1280 of each well type; the filled wells are about 2.6 nL in volume for the glass chips and about 3 nL in volume for plastic chips. Thermal expansion wells are about 0.3 nL in volume.

Some embodiments of the devices and methods disclosed here provide for a method of carrying out sequential reactions on multiple compartments. For example, a first fluid containing one or more molecules of interest can be introduced into a device. Compartmentalization of the fluid may be carried out by slipping to create the first set of compartments. In some preferred embodiments, some of the first compartments have single molecules of interest. A first reaction can be carried out, for example, by incubation at a particular temperature or combination of temperatures, by applying fields and gradients, and/or by other means. Second compartments of a second fluid, containing a reagent, can be created either in parallel with creating the first compartments, or prior to first compartments, or subsequently to the first compartments. After the desired extent of the first reaction, the first compartments containing the first reaction mixtures can be combined with the second compartments to carry out the second reaction. The second reaction could be carrying out on the product of the first reaction (for example, a second detection reaction on the product of the first nucleic acid amplification reaction), or could be performed on other components of the first reaction mixture (for example detecting a protein in the second reaction following a detection of a nucleic acid in the first reaction). In some embodiments, such sequential reactions can be carried out in parallel, for example in devices such as those illustrated in FIG. 2 and FIG. 14. In the example given in FIG. 14, the first reaction can be carried out, for example, during the stage labeled "isolate component 1" and the second reaction can be carried out during the stage labeled "react and readout".

As an additional example, molecules of interest can be molecules of nucleic acids. The first reaction could be an amplification reaction, and the second reaction could be a subsequent amplification reaction. The first reaction can be a reverse-transcription reaction and the second reaction could be an amplification reaction. The first reaction can be an amplification reaction, and the second reaction can be a detection reaction. The first reaction could be a sequencing library preparation reaction, and the second reaction could be an amplification reaction. Examples of other first and second reactions, which should not be considered limiting examples, include detection reactions. A non-limiting listing of reactions is provided at, e.g., paragraphs 0112-0124 in published United States Application 2011/0166044, the entirety of which is incorporated herein by reference. The exemplary embodiments disclosed herein regarding NASBA and LAMP amplification processes illustrate the foregoing, namely, a multi-step reaction process. Additional examples of embodiments that feature first and second reactions are described in priority application PCT/US2010/028316 at, e.g., at paragraph 0194 and elsewhere in that application. In one embodiment, the first reaction may be nucleic acid amplification (e.g., PCR), and the second reaction may be a recovery of the amplification products. In some embodiments, recovery of amplification products need not necessarily be performed by a reaction. The amplification products may be recovered by a filter, a monolith, and the like—materials that preferentially adsorb amplification products are considered especially suitable.

Recovery of products (e.g., amplified nucleic acid products) may be effected by removing the product (e.g., by pipette, syringe, or other device). Recovery may also be effected by actuating amplification product fluid with a carrier or lubricating fluid, as described in priority application PCT/US2010/028316. Further methods of moving fluids are also described in priority application PCT/US2010/028316.

As one example, a user might combine nucleic acids and amplification to form an admixture. The user may then introduce that admixture into a device according to the present disclosure so as to distribute the admixture among multiple areas (e.g., wells). The areas may be in fluid communication with one another, but may also be in fluid isolation from one another. Once the admixture is disposed into these areas, the user may apply conditions (heat, light) sufficient to effect a reaction in the admixture. The reacted admixture may then be distributed among other compartments, where the reacted admixture undergoes further reactions.

It should be understood that the devices and methods disclosed herein may be configured to effect a time delay between steps. For example, a sample and reagent may be introduced into a set of reaction compartments. At that time, the user may apply heat to the materials so as to effect a reaction between the sample and reagent. The user may then, after a time sufficient to allow the reaction to reach a desired stage, effect contact between the reacted material and another reagent, as described elsewhere herein. Delay may be effected manually or by action of a controller that actuates substrates, valves, pumps, or other components of the disclosed technology. Delays in the range of from one thousandth of a second to one second are suitable delay lengths, as such delays may be sufficient to allow sufficient progress of a reaction. Thus, in some embodiments, the devices may effect a first reaction during a delay, place the reaction products into contact with an additional reagent, and then effect a delay so as to allow a second reaction to take place.

This may be illustrated by reference to FIG. 6. In that figure, a user may (panel B) add first and second solutions to separate sets of wells. The first solution may be a solution (e.g., nucleic acid and amplification reagent) that undergoes a reaction in place (e.g., by application of heat, light, or by passage of time). The separate sets of wells may be combined so as to effect contact between the reacted first solution in the first set of wells and the second solution in a second set of wells.

It should also be understood that the present disclosure is not limited to application to molecules, as the disclosed devices and methods may be applied to organisms (such as those described in paragraph 0133 of priority application PCT/US2010/028316 and also elsewhere in that application), single cells, single biological particles (e.g., bacteria), single vesicles, single exosomes, single viruses, single spores, lipoprotein particles, and the like, and single non-biological particles. Furthermore, it should also be understood that the disclosed devices and methods may be applied to stochastic confinement (described in, for example, "Stochastic Confinement to Detect, Manipulate, And Utilize Molecules and Organisms," application no. PCT/US2008/071374), and reactions and manipulations of stochastically confined objects. As one non-limiting example, biological samples may be assessed for the presence or level of certain bacteria, such as those organisms that serve as markers for bacterial vaginosis. This assessment may be performed by amplifying nucleic acids that may be present in the sample and correlating the levels of those nucleic acids to the presence or absence of the marker organisms. An exemplary approach to such an analysis is found at http://www.viromed.com/client/cats/BV%20LAB.pdf.

Also presented are devices. The devices suitably include a first substrate having a first population of wells formed therein, at least one well of the first population of wells having at least one satellite well disposed proximate to the at least one well, the at least one satellite well being adapted to retain material from the at least one well; a second substrate having a second plurality of wells formed therein, the first and second substrates being slidably engageable with one another such that relative motion between the first and second substrates places at least some of the first population of wells in register with at least some of the second population of wells so as to form combined reaction chambers.

Figure 6:
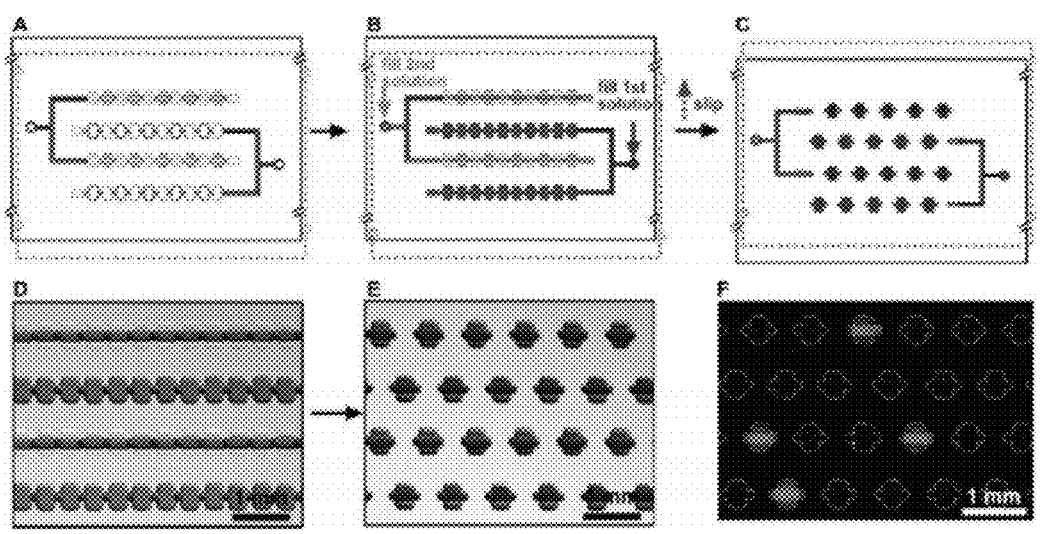
FIG. 6 illustrates a device for one-step digital RPA.

Exemplary devices are shown and described in FIGS. 2 and 6. At least one of the substrates may have a thickness in the range of from about 10 micrometers to about 500, about 1000, or even about 2000 micrometers. Substrates having a thickness in the range of from about 200 micrometers to about 700 micrometers are considered especially suitable. A well may have a volume in the range of from about 1 nL to about 5, 10, 25, 50, 100, 250, 500, or even about 1000 nL; a well need not be fully filled in order for the devices (and methods) disclosed herein to operate.

The relative motion (which may be referred to as actuating) may give rise to at least one reaction vessel defined by a well of the first population of wells in fluid communication with a well of the second population of wells, the at least one reaction vessel. The reaction vessel may be in fluidic isolation from other wells or other reaction vessels, also fluidic isolation is not q requirement. The reaction vessel may have a volume in the range of from about 1 nL to about 5, 10, 25, 50, 100, 250, 500, or even about 2000 or even 5000 nL, depending on the user's needs. Exemplary fabrication methods for such devices are set forth in Du et al., Lab Chip 2009, 9, 2286-2292. A population of wells of the disclosed devices may include two or more wells of different volumes. As described elsewhere herein, a reaction vessel may include at least one satellite well, which wells are described elsewhere herein, and are shown in exemplary FIGS. 2 and 6.

It should be understood that the methods may include one, two, or more applications of relative motion between substrates. For example, a first relative motion (e.g., rotation) may be applied so as to place first and second sets of wells into fluid communication with one another. Once the contents of the first and second wells have contacted one another, additional rotation may be applied to place the wells with mixed contents into fluid communication with another set of wells with different contents, which in turns enables the user to effect processes that require separate and/or sequential mixing steps of two, three, or more sample volumes. This might be done, for example, to (1) mix materials in well A and well B in well A; and then (2) to contact the mixed materials in well A with a buffer in well C so as to dilute the contents of well A. Alternatively, the mixed contents of well A might then be contacted (via relative motion of substrates) with well C such that the contents of well C may react with the contents of well A (which well included the contents of well A and well B).

The devices may be configured such that relative motion between the substrates gives rise to at least about 2, 5, 10, 100, 500, 1000, 2500, or even about 10,000 (including any and all intermediate values) combined reaction chambers. The disclosed devices may include one or more supplies of a reagent or reagents that are adapted (or selected) to participate in nucleic acid amplification. Such reagents may be packaged together with the first and second substrates. A partial, non-exclusive listing of such reagents includes buffers, primers, and the like. The reagent may be dried and disposed in a well before or after the substrates are engaged with one another. The reagent may also be disposed within a well and then dried.

The present disclosure also provides kits. The kits suitably include a first substrate having a first population of wells formed therein; a second substrate having a second population of wells formed therein, the first and second substrates being superposable and slidably engageable with one another such that relative motion between the substrates places at least some of the first population of wells into fluid communication with at least some of the second population of wells; and a supply of at least one reagent adapted to participate in amplification of nucleic acid. The kits may, however, include reagents in addition to or even in place of the amplification reagent. Such reagents may include lysis agents, acids, bases, surfactants, enzymes, preservatives, labels (e.g., fluorophores), and the like. A nonexclusive set exemplary reagents are provided in priority application PCT/US2010/02816. The reagent may be packaged with the substrates. The reagent may also be packaged (e.g., in dried form) within an area (e.g., a well) of a substrate. The kit may also include one or more fluids (e.g., water, buffer) that may be used to reconstitute a reagent stored within the kit. The kit may also include a sample collection device (swab, syringe, pipette) for collecting a sample.

As described elsewhere herein, the first population of wells comprises two or more wells that differ in volume from one another; similarly, the second population of wells comprises two or more wells that differ in volume from one another. The reagent may be adapted (or selected) to participate in one or more of polymerase chain reaction, nucleic acid sequence based amplification, recombinase polymerase amplification, loop-mediated amplification, rolling circle amplification, helicase dependent amplification, transcription mediated amplification, multiple displacement amplification, strand displacement amplification, or any combination thereof.

In the disclosed kits, the at least one reagent may be disposed within at least some of the first population of wells, the second population of wells, or both. The reagent may be, as described elsewhere herein, present in dried form.

The first and second substrates may be planar at a region of overlap between the two substrates, as shown in FIGS. 2 and 6. Alternatively, the substrates may be non-planar at a region of overlap between the substrates. For example, the substrates may be curved, conical, or even frustoconical.

The disclosed kits may include a device capable of supplying or removing heat from the first and second substrates. Such devices include heaters, refrigeration devices, infrared or visible light lamps, and the like. The kits may also include a device capable of collecting an image of at least some of the first population of wells, the second population of wells, or both. The device may be further configured to analyze the image and to estimate a level of an analyte present in a sample that has been processed by the kit. In such embodiments, the device may be configured to detect the presence or absence of a target present in the first population of wells, the second population of wells, or both. The device may be manually portable (e.g., a mobile phone, a table computer, or digital camera).

As one example, an iPhone 4S™ is useful to capture results on a disclosed device. A fluorescence readout is achieved by a standard iPhone 4S™ 8 MP camera equipped with a yellow dichroic long-pass filter 10CGA-530 (Newport, Franklin, Mass.). Fluorescence excitation is achieved by shining light (e.g., blue light) on a device. The light may be applied at an oblique angle, e.g., about 30 degrees. A variety of light sources may be used; one suitable source is a blue LED (LIU003) equipped with a blue short-pass dichroic filter FD1B (Thorlabs, Newton, N.J.). Excitation light may reach the sample by direct illumination, by multiple reflections between the device plates, or both.

Exemplary estimation methods are described in, e.g., Shen et al., JACS 2011 133: 17705-17712; Kreutz et al., Anal. Chem. 2011 83: 8158-8168; and Shen et al., Anal. Chem. 2011 83: 3533-3540, each of which is incorporated herein by reference in its entirety. These and other estimation methods may be applied to the devices and methods presented herein.

In another embodiment, the present disclosure provides methods of amplifying a nucleic acid molecule. These methods suitably include contacting (a) a sample comprising at least one nucleic acid molecule disposed at a plurality of first areas, with (b) at least one component of an amplification reagent disposed in a plurality of second areas; the contacting is suitably effected by placing the first and second areas into direct fluid communication with one another. The contacting also suitably includes effecting relative motion between a substrate comprising the first area with a substrate comprising the second area, and exposing the area having the at least one nucleic acid molecule to conditions effective for amplification of the at least one nucleic acid molecule, The amplification may be effected essentially isothermally. Various methods of essentially isothermal amplification are set forth elsewhere herein. The essentially isothermal amplification suitably comprises fewer than 10 changes in temperature. As stated elsewhere herein, however, it should be understood that the disclosed devices and methods are not limited to isothermal methods of amplification.

In some embodiments, at least two of the plurality of first areas differ from one another in volume. In some embodiments, at least two of the plurality of second areas differ from one another in volume; in still other embodiment, at least one first area differs in volume from at least one second area, or any combination thereof. The differences in volumes allow a user to place populations of areas (e.g., wells) into fluid communication with one another to create paired areas in register with one another. These paired areas (e.g., wells) then define a combined reaction region. In certain embodiments, the paired areas define combined reaction regions of different volumes. For example, a 1 nL area may be placed pairwise into fluid communication with a 5 nL area to give rise to a combined reaction region having a volume of about 6 nL. The user may also combine a 1 nL area with a 10 nL area so as to give rise to a combined reaction region having a volume of about 11 nL. In this way, a user may give rise to a set of combined reaction regions having different volumes (6 nL and 11 nL, in the present example).

The amplification may also be performed in a multiplexed fashion. In one such embodiment, amplification is performed at multiple areas. In another embodiment, amplification of different nucleic acids is performed at multiple areas; a user might amplify a first nucleic acid at 10 locations, and amplify a second nucleic acid at 10 different locations.

The relative motion between the various areas may be linear translation, rotational motion, or nonlinear motion. The relative motion may be effected manually (e.g., by hand). Alternatively, the relative motion may be effected under control of a programmed (or programmable) controller. Such a controller may interface with a motor that in turn effects motion of the substrates.

In some embodiments, the first and second areas are placed into direct fluid communication with one another; i.e., the areas face one another. In some embodiments, one may remove a barrier (e.g., a membrane, film, and the like) that resides between first and second areas.

A user may also estimate a level (e.g., concentration) of nucleic acid present in the sample. This estimation may be performed by a variety of methods described herein. Exemplary estimation methods are described in, e.g., Shen et al., JACS 2011 133: 17705-17712; Kreutz et al., Anal. Chem. 2011 83: 8158-8168; and Shen et al., Anal. Chem. 2011 83: 3533-3540, each of which is incorporated herein by reference in its entirety.

In some embodiments, at least 10 first areas are placed into direct fluid communication with at least 10 second areas essentially simultaneously. In other embodiments, at least 50 first areas are placed into direct fluid communication with at least 50 second areas essentially simultaneously. A user may place at least 500 first areas into direct fluid communication with at least 500 second areas essentially simultaneously.

Areas that define a volume in the range of from about 0.1 nL to about 1000 nL are considered particularly suitable. Volumes in the range of from about 5 to about 10 nL are considered suitable.

In applying the disclosed methods, the area having the at least one nucleic acid molecule is estimated to contain one molecule of nucleic acid. This estimation may be performed mathematically; a user may modulate sample concentration and area volume so as to arrive at a configuration wherein at least one area contains a single nucleic acid molecule.

The disclosed methods may also include the step of amplified nucleic acid. This detection may be effected by assaying an area for the presence of a marker (e.g., a label) that is indicative of the presence of the nucleic acid. A user may also correlated an estimated level of the at least one nucleic acid in the sample to a disease state in the source of the sample. As one example, a user may determine that the presence of a particular nucleic acid that marks the presence of a bacteria in an amplification product indicates the presence of that bacteria in the source of the sample. A user may also isolate a nucleic acid from the sample; such isolation may include manipulating the sample (pipetting, diluting, concentrating) so as to isolate nucleic acid. The user may also use a capture material (e.g., silica) that adsorbs nucleic acids.

In some embodiments, the user may disposed the at least one nucleic acid at the first area. This may be effected by pipetting, spraying, injecting, and the like. A user may introduce the sample at the first area, introducing a amplification reagent at the second area, or both.

In some embodiments, introducing the sample at the first area comprises exerting the sample through a conduit in fluid communication with the first area. The conduit may be formed in a substrate that comprises the first area. A user may also introduce sample at the second area; this may be accomplished by exerting the sample through a conduit in fluid communication with the second area. Such a conduit may be formed in a substrate that comprises the second area.

In some embodiments (e.g., FIG. 2), the user may distribute sample between the first area and a first control area. Sample at the first control area suitably remains free of contact with the at least one amplification reagent, as shown in FIG. 2.

A user may also distribute the at least one amplification reagent between the second area and a second control area. The reagent (see FIG. 2) in a control area may remain uncontacted with the sample.

Users may place amplification product into direct fluid communication with a third area. In this way, a user may create an amplification product and then place that product (e.g., by effecting relative motion between an area where that product resides and another area that contains a reagent) into contact with a reagent. In this way, a user may realize multistep processes that create a first product and then further process that product.

The present disclosure also provides devices. The devices suitably include a first substrate having a first population of areas, at least one area of the first population of areas having at least one satellite area disposed proximate to the at least one area, the at least one satellite area being adapted to retain material from the at least one area; a second substrate having a second plurality of area formed therein, the first and second substrates being engagable with one another such that relative motion between the first and second substrates places at least some of the first population of areas in register with at least some of the second population of areas so as to place the first and second areas into fluid communication with one another.

One such exemplary device is shown in FIG. 2. As shown in that figure, a satellite area may be adapted to retain material not retained by a first and second area that are placed into fluid communication with one another. In this way, the satellite well retains excess material so as to prevent that material from interfering with operation of the device, e.g., by coming into contact with another area (e.g., well).

At least one of the first or second substrates suitably has a thickness in the range of from about 10 micrometers to about 5000 micrometers. Thicknesses in the range of from 20 micrometers to about 100 micrometers are considered especially suitable. At least one area of the first or second populations includes an area that defines a volume in the range of from about 1 pL to about 1 microL.

The disclosed devices may be configured such that the relative motion gives rise to at least one reaction region defined by an area of the first population of areas in fluid communication with an area of the second population of areas. Such a reaction region may define a volume in the range of from about 1 pL to about 1 microL. A satellite well is suitably disposed proximate to at least one reaction region.

As described elsewhere herein and in the priority documents, the first population of areas may include two or more areas that differ from one another in volume. Likewise, the second population of areas may include two or more areas that differ from one another in volume.

The devices may be configured such that the relative motion between the substrates gives rise to at least about 10 reaction regions. The devices may be configured such that the relative motion gives rise to at least about 50, 100, 1000, or even about 5000 reaction regions.

The devices may also include (or be packaged with) one or more reagents. The reagents are suitably selected so as to be capable of participating in one or more reactions that a user may effect on a sample disposed in the disclosed devices. As one example, a device may include a reagent adapted to participate in nucleic acid amplification.

Also provided are methods. These methods effect amplification of at least one nucleic acid target molecule, and the methods suitably include contacting (1) a sample material disposed in a plurality of first areas, the sample material comprising a nucleic acid target, and at least one of the first areas containing one molecule of the nucleic acid target, with (2) a reactant material disposed in a plurality of second areas, the contacting being effected by pairwise placement of at least some of the first areas and at least some of the second areas into direct fluid communication with one another, the contacting effecting amplification of at least one nucleic acid target molecule.

In some embodiments, the sample material may include a reagent. As one illustrative example, the sample material may include one or more nucleic acid target molecules as well as suitable amplification reagents. The amplification may, in some cases, be essentially isothermal. In embodiments that include amplification, a user may estimate the level of the at least one nucleic acid target.

In other embodiments, the reagent (disposed at the second area or areas) comprises an amplification reagent. In these embodiments, a user may effect amplification by using relative motion between the first and second areas to contact the sample with the amplification reagent. A user may also expose an area containing the at least one nucleic acid molecule to conditions effective for amplification of the at least one nucleic acid target so as to give rise to an amplification product. As described elsewhere herein, the amplification may be essentially isothermal. A user may also estimate the level of the at least one nucleic acid target.

The pairwise placement described above may be effected by relative motion of the first and second areas. This pairwise placement may act to place at least 10 first areas into direct fluid communication with at least 10 second areas. It may also act to place at least 50 first areas into direct fluid communication with at least 50 second areas. The relative motion between the first and second areas may, as described elsewhere herein, be effected manually by a controller, or both.

The present disclosure also provides methods. These methods include dispersing a first sample that comprises at least one molecule of interest among a plurality of first areas, at least one of the first areas containing a single molecule of interest; dispersing a reactant material into a plurality of second areas; and effecting pairwise placement of at least some of the plurality of first areas into direct fluid communication with at least some of the plurality of second areas so as to contact reactant material with the first sample.

In some embodiments, the first sample is dispersed among the plurality of first areas at essentially the same time among the plurality of first areas. In some embodiments, the reactant material is dispersed among the plurality of second areas at essentially the same time among the plurality of second areas. The pairwise placement of the at least some of the plurality of first areas into direct fluid communication with at least some of the plurality of second areas may occur at essentially simultaneously the same time among the majority of any pairs formed by first and second areas. Some embodiments feature two or more of foregoing.

In a particular embodiment of the disclosed methods, the first sample comprises a reagent, and the user may effect a reaction between the reagent and at least one molecule of interest. The reaction may be nucleic acid amplification, which amplification may be essentially isothermal. A user may also recover a product of the nucleic acid amplification; suitable recover methods are described elsewhere herein. The pairwise placement of areas into fluid communication with one another is suitably effected by relative motion of the first and second areas, also as described elsewhere herein.

A user may effect a reaction between the contacted reactant material and the first sample. Various suitable reactions are described elsewhere herein, and can include nucleic acid amplification (including essentially isothermal amplification) of the at least one molecule of interest. The reactant may be an amplification reagent. A user may recover a product of the nucleic acid amplification, and this product may be subjected to further processing.

The recited pairwise placement may place at least 10 first areas into direct fluid communication with at least 10 second areas. The pairwise placement may place at least 50 first areas into direct fluid communication with at least 50 second areas.

Exemplary Embodiments

Digital RPA

The following embodiments explore digital quantitative detection of nucleic acids was achieved at the single-molecule level by chemical initiation of over a thousand nanoliter, sequence-specific, isothermal amplification reactions in parallel. Digital polymerase chain reaction (digital PCR), a method used for quantification of nucleic acids, counts the presence or absence of amplification of individual molecules. Digital PCR, however, typically requires temperature cycling. This makes isothermal methods for nucleic acid amplification, such as recombinase polymerase amplification (RPA) suitable.

A microfluidic digital RPA device is described here for simultaneous initiation of over a thousand nanoliter RPA reactions by adding a chemical initiator to each reaction compartment with a simple slipping step after instrument-free pipette loading.

Two device designs, two-step slipping and one-step slipping, are described using digital RPA. By using the disclosed devices, false positive results from pre-initiation of the RPA amplification reaction before incubation were eliminated. End-point fluorescence readout was used for "yes or no" digital quantification. The performance of digital RPA in the disclosed devices was shown by amplifying and counting single molecules of the target nucleic acid, Methicillin-resistant *Staphylococcus aureus* (MRSA) genomic DNA. The digital RPA on the disclosed devices was also tolerant to fluctuations of the incubation temperature (37-42° C.), and its performance was comparable to digital PCR on the same device design. The digital RPA devices provide methods to quantify nucleic acids without requiring thermal cycling or kinetic measurements, with potential applications in diagnostics and environmental monitoring under resource-limited settings. The ability to initiate thousands of chemical reactions in parallel on the nanoliter scale using solvent-resistant glass devices is useful for a broad range of applications.

To reduce thermal cycling, different isothermal amplification methods have been developed, including loop-mediated amplification, nucleic acid sequence based amplification, recombinase polymerase amplification, rolling circle amplification, helicase-dependent amplification, transcription-mediated amplification, multiple displacement amplification (MDA), and strand-displacement amplification (SDA). These real-time methods of isothermal amplification can be sensitive to temperature because the enzyme activity is highly temperature-dependent. To avoid effects of temperature changes and fluctuations, calibration is preferably done in parallel to quantitatively analyze nucleic acids. Moreover, most of the methods for detection and analysis of nucleic acids using NASBA and RPA still depend on interpreting exponential amplification profiles.

Although digital PCR typically requires thermal cycling and accurate temperature control, the technique is straightforward because initiation of the amplification reaction is controlled by temperature. So-called "hot-start" modifications of PCR polymerases are now widely used and substantially eliminate any low-temperature non-specific pre-amplification. The PCR reaction mixture can be compartmentalized prior to initiation with minimal risk of false-positives due to pre-initiation. In situations where the infrastructure for thermal cycling is readily available, digital PCR is an attractive option for nucleic acid quantification. In limited-resource or point-of-care settings, digital isothermal amplification methods that take place at temperatures near room temperature (such as RPA) are advantageous because they do not rely on a raised temperature for initiation, but rather rely on mixing. If the nucleic acid target is premixed with the initiation reagent prior to compartmentalization, one might expect the amplification reaction to proceed even at room temperature and thus increase the target count. Thus, one may compartmentalize the sample containing the nucleic acid target prior to adding the initiation reagents. Multistep manipulation can also be done with valves and droplets, but such systems typically use complex control systems and instrumentation, so it is preferably achieved on a device that does not require complex control systems and instrumentation.

Certain embodiments of the disclosed devices comprise two plates containing wells and ducts that can be brought in contact and moved relative to one another to manipulate fluids by creating and breaking fluidic paths. The pattern of wells and ducts in the two plates can contain almost any program to manipulate fluid volumes; compartmentalizing a sample into many small volumes and mixing each small volume with a reagent can be performed by simple subsequent slipping of the two plates.

Here is described devices and methods to perform digital isothermal amplification by using RPA. It is demonstrated that digital RPA does not require precise temperature control, as equivalent quantification results were obtained when quantifying MRSA gDNA at 37° C., 39° C., and 42° C. One advance presented here is the capability to first confine individual target molecules into separate reaction compartments, and then deliver chemical initiators to initiate reaction in parallel, a requirement of digital RPA. The devices may, of course, be applied to perform other high throughput chemical reactions or screenings that require multistep processes such as confinement of one reagent and then addition of subsequent reagents in sequence, as the digital RPA described here is illustrative only.

RPA Results

The mechanism of DNA amplification and fluorescence signal generation facilitated by RPA is described in elsewhere. RPA uses nucleoprotein complexes consisting of oligonucleotide primers and recombinase proteins to target binding sites within template DNA. Upon their binding, the primers are extended by strand-displacing polymerases, thereby copying the target sequence. The use of primers binding to the opposing strands of the template initiates a process of exponential DNA amplification. The generation of amplified target material can be monitored by an appropriate oligonucleotide-probe based fluorescence detection system in the approach used here, a fluorophore/quencher bearing probe is nucleolytically cut in response to sequence-specific binding to amplified DNA. This processing step results in a separation of the fluorophore and quencher groups, thereby leading to an increase in observable fluorescence.

Although the RP A reaction normally proceeds at 39° C., it was first tested to determine to what extent it would proceed at room temperature (25° C.) upon mixing of the reagents in well plates, therefore potentially affecting the accuracy of the RPA results when performed in a digital format. The RPA solution was mixed with magnesium acetate and Methicillin-resistant *Staphylococcus aureus* (MRSA) genomic DNA (gDNA, final concentration of 5 pg/11 L), then immediately placed in the plate reader (temperature controlled at 25° C.). The fluorescence intensity from wells containing gDNA template (FIG. 1, green) started increasing within 20 min, which was different from the fluorescent intensity of the control well without magnesium acetate (FIG. 1, blue) and the control well without gDNA template (FIG. 1, orange).

FIG. 1 shows RPA amplification of MRSA genomic DNA (5 pg/11 L) in a well plate at 25° C. Triplicate curves (upper lines) show that gDNA template was amplified at room temperature. The control experiment without template (flat line) and the control experiment without magnesium acetate $(Mg(OAc)_2$, flat line) show no amplification.

This result suggested that the RPA reaction amplified the target nucleic acid template in the presence of magnesium acetate at room temperature. Therefore, to achieve digital RPA without false-positive errors, the nucleic acid template may be compartmentalized first and then magnesium acetate is added to each individual compartment. The non-initiating components of the RP A reaction mixture (RPA enzymes, buffer, primers, and probe) can be added to the solution containing nucleic acid template, to the solution of magnesium acetate, or to both.

To achieve this goal, a device was designed that featured two-step slipping, which device was able to load and compartmentalize two different reagents that could be combined by slipping (FIG. 2). Each plate of the RPA device was designed to contain 800 wells of Type I (6 nL) and 800 wells of Type II (3 nL).

Each Type II well also had two satellite wells (0.2 nL) to address potential thermal expansion during the temperature change from room temperature to 39° C. The satellite wells provided additional space for thermal expansion of the aqueous reagent within the compartment formed by overlapping the Type I and Type II wells. A total of 1,550 reaction compartments (9 nL each) were formed by overlapping the Type I and Type II wells contained in the facing plates (FIG. 2F, I, N). The device also contained 50 wells for control 1 (Type I wells, 6 nL, FIG. 2A, F, J) and 50 wells for control 2 (Type II wells, 3 nL, FIG. 2A, F, H).

The digital RPA device was assembled by combining the top plate (FIG. 2A) and bottom plate (FIG. 2B) with a thin layer of tetradecane between as the lubricating fluid. The lubricating fluid prevented cross-contamination and evaporation of the aqueous sample during incubation. The first continuous fluidic path was formed by overlapping the Type I wells in the two plates (FIG. 2C). RPA Reaction Mixture 1, containing RPA primers and probe, MRSA gDNA, and re-hydrated RPA enzyme mixture, but no magnesium acetate, was loaded by pipetting (FIG. 2D, K). This RPA device was designed to be filled via dead-end filling, therefore, the speed of sample injection need not necessarily be controlled so long as the applied pressure is lower than the leaking pressure.

Figure 9:
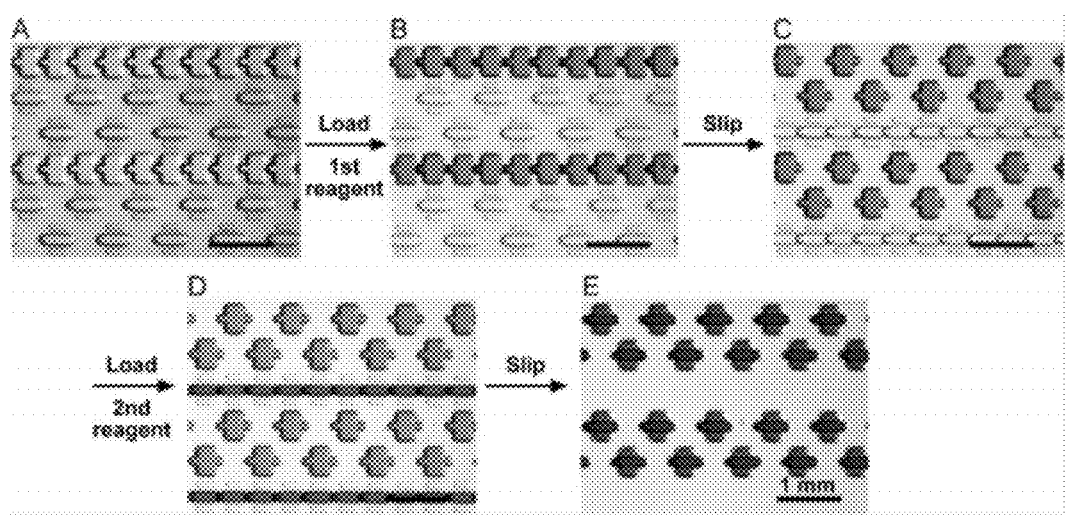
FIG. 9 illustrates food dye experiment demonstrated the operation of slipping for a digital RPA device.

The two plates were then slipped relative to one another to compartmentalize RPA Reaction Mixture 1, simultaneously stochastically confining the gDNA template in the Type I wells and forming the second fluidic path by overlapping the Type II wells (FIG. 2E, L). RPA Reaction Mixture 2, which contained no gDNA and contained magnesium acetate at three fold higher concentration than required for the bulk reaction (3×, so the final concentration of magnesium acetate after mixing would be IX), RP A primers and probe, and re-hydrated RPA enzyme, was also loaded into the chip by pipetting (FIG. 2E, M). Finally, the two plates were slipped relative to one another to overlap the Type I wells with the Type II wells in the facing plates, delivering the magnesium acetate in Reaction Mixture 2 to all 1550 of the Type I wells simultaneously and initiating the reaction FIG. 2F, N; FIG. 9). The digital RPA device was then placed on a flat metal adapter and incubated at 39° C. for 1 hour. Type I wells for Control 1 contained only Reaction Mixture 1 (negative control, no magnesium acetate), and Type II wells for Control 2 contained only Reaction Mixture 2 (negative control, no nucleic acid template).

FIG. 2 illustrates a schematic drawing of the two-step device for digital RPA A) Top plate of the device. A zoomed in schematic drawing shows the geometry of Type I, Type II and satellite wells. B) Bottom plate of the device. C) Assembly of top and bottom plates to establish the first continuous fluidic path of Type I wells. D) Loading of the first reagent, Reaction Mixture 1 (red). E) Slipping breaks the first fluidic path and compartmentalizes the loaded reagent. At the same time, the second fluidic path is formed by connecting Type II wells. The second reagent, Reaction Mixture 2 (light blue), is loaded through a second inlet. F) A second slipping step compartmentalizes Reaction Mixture 2 into the Type II wells and overlaps the Type II wells with the Type I wells. The two reagents are mixed within the reaction compartments. G) Microphotograph shows the entire digital RPA device next to a United States quarter coin for scale. H, I, J) Food dyes were loaded into the device to demonstrate loading and mixing. H) Zoomed in view of Type II wells for Control2 (no template), loaded with blue food dye. I) Zoomed in view of reaction wells (overlapping Type I and Type II wells) containing mixed blue and orange food dye (green). H) Zoomed in view of Type I wells for Control 1 (no magnesium acetate), loaded with orange food dye. K, L, M, N) Experiments with food dye demonstrate the procedures described in panels D, E, F of the figure.

Figure 3:
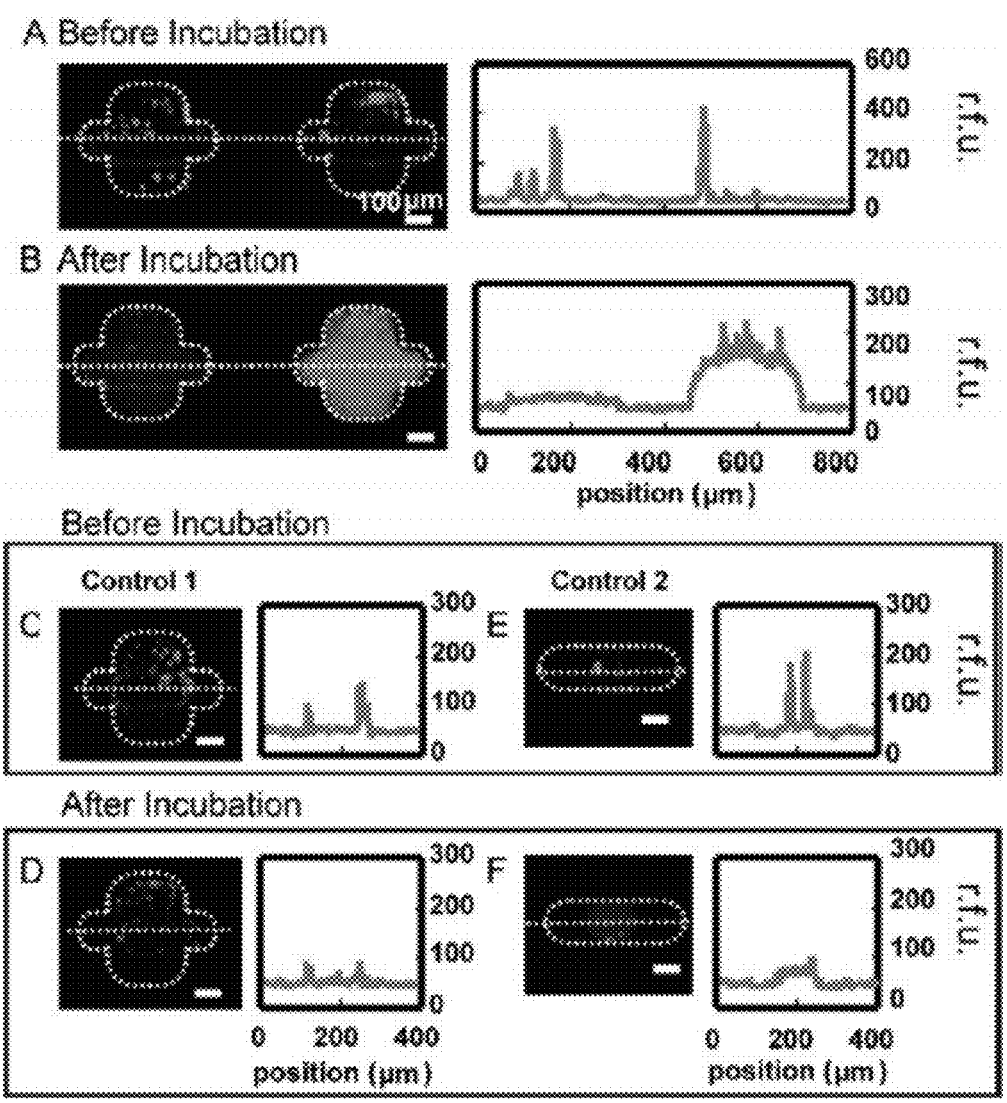
FIG. 3 illustrates fluorescence microphotographs and linescans of RPA on a disclosed device before and after incubation at 39° C.

A digital RPA device was applied to a sample containing a 1:104 dilution of 5 ng/11 L of stock MRSA gDNA. The stock gDNA was purified from MRSA culture, and the optical density of the purified nucleic acid product was measured spectrophotometrically. At this concentration, the average copy number of gDNA per well was expected to be less than 1, and single-copy RPA was achieved. The reaction solution of RPA was made from rehydrating the lyophilized reagent, and was heterogeneous: microparticles of various sizes and shapes were still present even after sonication and vortexing the solution (FIG. 3A). A linescan of the fluorescence intensity of wells from the digital RPA device before and after incubation at 39° C. (FIG. 3) shows that the fluorescence intensity of a positive well increased significantly compared to a negative well (FIG. 3A-B) and the control wells (FIG. 3C-F) after incubation for one hour. The number and the size of microparticles decreased after incubation, which may be due to further dissolution of the microparticles during incubation at 39° C. There was no significant increase of fluorescence intensity from control wells without magnesium acetate (representative Control well 1, FIG. 3C-D) and without gDNA template (representative Control well 2, FIG. 3E-F). Only the endpoint fluorescent intensity was monitored in this experiment. The amplification signal may be observed in less than 30 min. A real-time fluorescence detector can be used to further investigate the uniformity of amplification and to optimize the total time required for incubation.

FIG. 3 illustrates fluorescence microphotographs and linescans of RPA on the device before and after incubation at 39° C. (A-B) Negative (left) and positive (right) sample wells: (A) before incubation, the fluorescence intensity in both wells is the same. (B) After incubation, the integrated fluorescence intensity in the positive well (right) is significantly higher compared to the negative well (left). (C-D) Control well 1, containing no magnesium acetate, before (C) and after (D) incubation shows no significant increase in fluorescence intensity. E-F) Control well 2, containing gDNA template, before (E) and after (F) incubation also shows no significant increase in fluorescence intensity.

Figure 4:
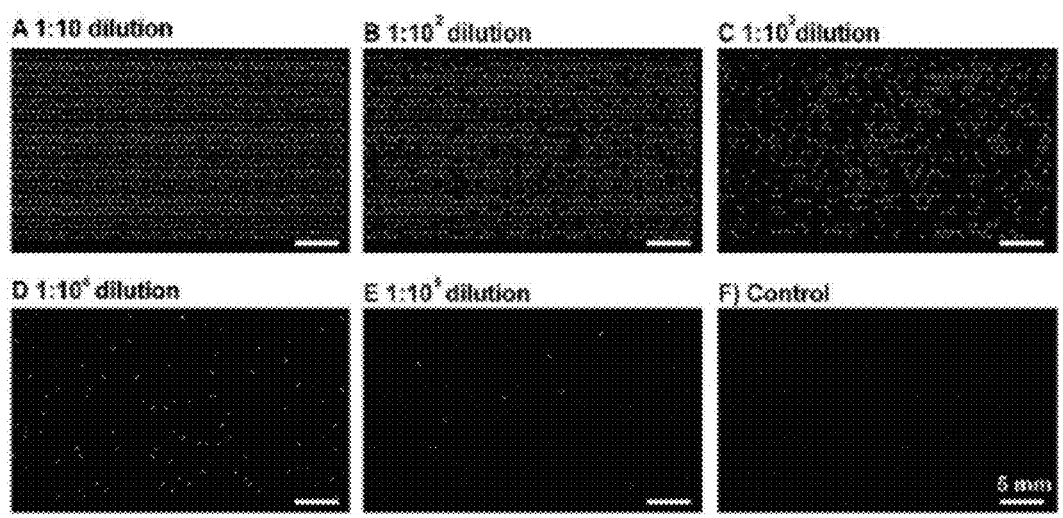
FIG. 4 illustrates digital RPA on a disclosed device with different concentration of MRSA gDNA.
Figure 5:
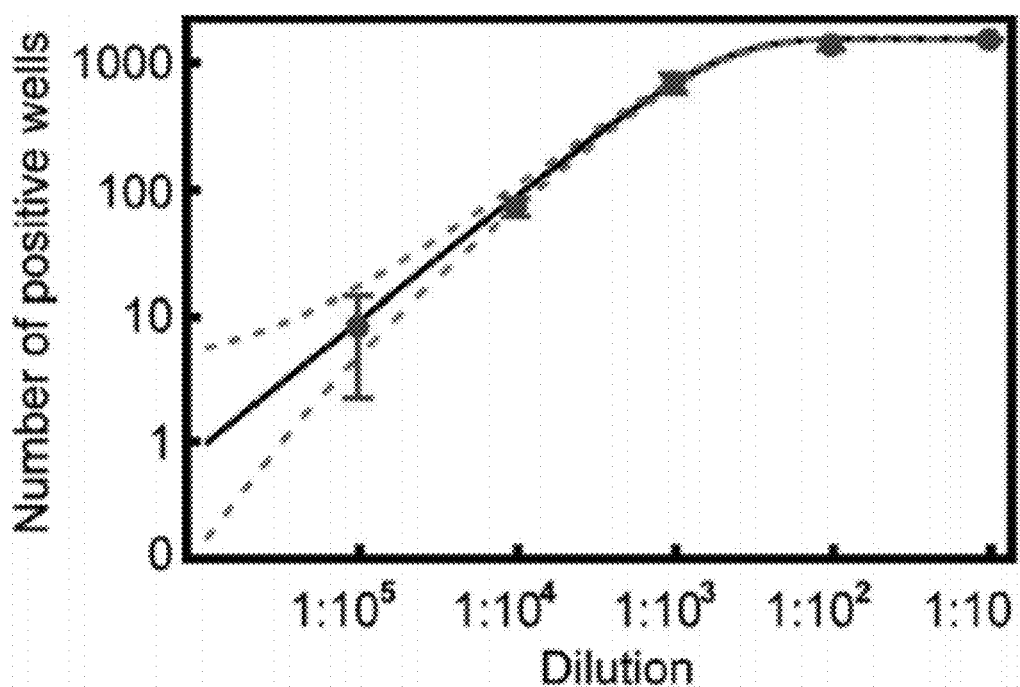
FIG. 5 illustrates quantified results of digital RPA on a disclosed device.

Performance of the digital RPA device was explored using a serial dilution of the MRSA gDNA stock solution at five orders of magnitude, from 1:10 dilution to $1:10^5$ dilution. As the gDNA template was diluted, the fraction of positive wells on the RPA device decreased proportionally after incubation (FIG. 4 A-E and FIG. 5). No evidence of contamination was observed as no false positives were observed in the control (no DNA template. FIG. 4F). The experiments were repeated three times at each concentration of gDNA to demonstrate the robustness and reproducibility of the digital RPA on the device (FIG. 5). The data from RPA on the device with serial diluted gDNA template followed a Poisson distribution. A statistical analysis of the results from digital nucleic acid amplification on the device was performed as previously described (Lab Chip 2010, 10, 2666-2672). By fitting the results from the $1:10^3$, $1:10^4$, and $1:10^5$ dilutions to a Poisson distribution (FIG. 5), the concentration of stock MRSA gDNA was characterized to be approximately 10 million copies/mL. A 95% confidence interval for the fitted Poisson distribution was calculated based on methods previously presented (Lab Chip 2010, 10, 2666-2672) (FIG. 5, dashed lines).

FIG. 4 shows a digital RPA on a device with different concentration of MRSA gDNA. A-E) Digital RPA on the device with a serial dilution of target DNA template ranging from 1:10 to $1:10^5$ of a 5 ng/11 L stock solution. (F) Control, no wells showed positive signal when no target DNA was loaded.

FIG. 5 illustrates quantified results of digital RP A on the device. Experimental average of the number of positive wells was plotted as a function of the dilution of the MRSA gDNA sample. Error bars represent standard deviation of the experiment (n=3). The black solid line represents the Poisson distribution obtained by fitting the data from the $1:10^5$, $1:10^4$, and $1:10^3$ dilution of template. Gray dash lines represent the 95% confidence interval for the fitted Poisson distribution.

The device design described above uses a two-step procedure for loading reagents: the two reagents can be loaded independently of one another, an attractive capability for general parallel processing of samples and reactions. Incubation or thermal cycling can be performed after confining the target molecules or the first reagent into individual reaction compartments, then additional reagents can be delivered (e.g., reagents for readout) into each compartment in parallel. This feature also facilitates quality control during development of new methods. Digital RPA typically requires this parallel processing of reactions, but does not typically specifically require two-step processing. Also presented here is a simplified device that does not independently control reagents but instead allows compartmentalization and mixing of the two reaction mixtures in parallel by one-step slipping after simultaneous introduction of the reagents (FIG. 6 A-E): Digital RPA with a $1:10^4$ dilution of MRSA gDNA template is demonstrated on this one-step device, and the result is consistent with the two-step devices (FIG. 6 F, compare to FIG. 7B, n~3, p>0.2)

FIG. 6 illustrates a device for one-step digital RP A A-C) Schematic drawings of the device: A) Assembly of top and bottom plates to establish the continuous fluidic path for both Type I wells and Type II wells. B) The first solution, Reaction Mixture 1 (red), and second solution, Reaction Mixture 2 (blue), were introduced simultaneously into the device. C) Slipping breaks both fluidic paths and compartmentalizes the loaded reagent. At the same time, the Type I wells were overlaid with Type II wells to initiate the reaction. D, E) Microphotographs showing food dyes loaded into the device to demonstrate loading and mixing. F) Zoomed-in fluorescent image of a fraction of digital RPA on one-step device with a 1:104 dilution of MRSA gDNA template after incubation at 39° C.

As shown, RPA can be initiated at room temperature (~25° C.) after magnesium acetate is added (FIG. 1). To achieve digital RPA, the reaction mixture containing target nucleic acid template may be preferably separated into isolated reaction compartments before magnesium acetate IS added. This was demonstrated quantitatively on the disclosed devices. Instead of mixing Reaction Mixture 1 (without magnesium acetate) with Reaction Mixture 2 (with magnesium acetate) on-chip, the reaction solution (containing a 1:104 dilution of gDNA) was mixed with magnesium acetate to initiate the reaction off-chip, and incubated the solution at room temperature (~25° C.) for 1 minute. One may refer to this off-chip mixing and incubation as the "pre-initiated" reaction solution. The pre-initiated reaction solution was then injected into the two-step digital RPA device at room temperature through the Type I wells, and slipped to compartmentalize. The injection step took around 4 minutes. A second solution that contained magnesium acetate, RPA primers and probe, and re-hydrated RPA enzyme was loaded into the Type II wells as described above.

Following that, the Type I and Type II wells were overlaid by slipping the top plate relative to the bottom plate. The device was then incubated at 39° C. for 1 hour. These results were compared to results obtained without pre-initiating the solution with magnesium acetate off-chip (from experiments shown in FIGS. 4 and 5). The fraction of positive wells from the pre-initiated sample was significantly higher than in the sample without pre-initiation (FIG. 7A, n=3, p<0.01). Without being bound to any single theory, one may attribute the large standard deviation in the measurement of the pre-initiated sample to the variation in loading time changing the extent of reaction prior to compartmentalization; reaction taking place during loading is also consistent with the "streaky" distribution of the positive wells in these experiments (see FIG. 10). These results demonstrate that compartmentalization followed by chemical initiation of the RP A reaction is preferred for obtaining quantitative results using digital RPA.

Figure 7:
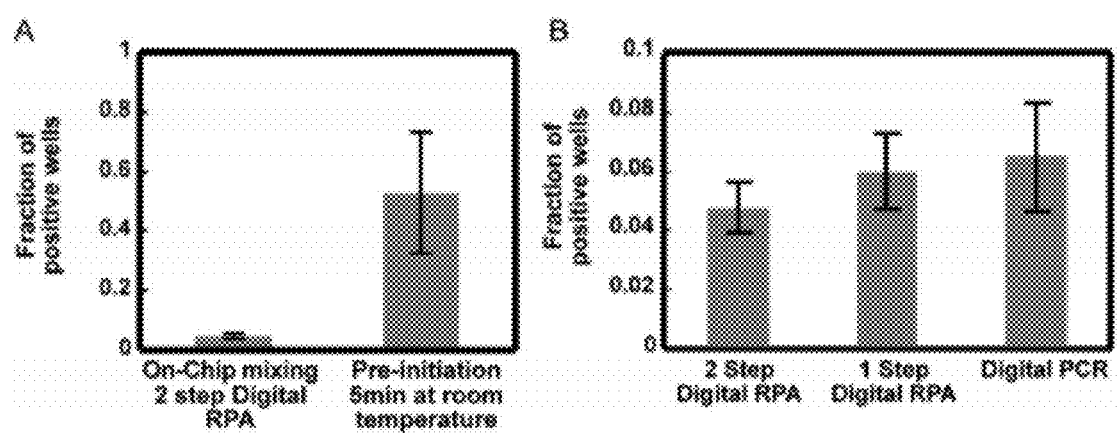
FIG. 7 illustrates comparative processes.

FIG. 7 illustrates A) Comparing on-chip mixing (no pre-initiation) to pre-initiation with magnesium acetate on the two-step digital RPA device. The sample with pre-initiation with magnesium acetate prior to compartmentalization shows a higher fraction of positive wells, indicating that compartmentalization prior to the addition of magnesium acetate is preferred for achieving accurate digital RP A B) Comparing two-step digital RPA, one-step digital RP A and digital PCR Samples containing MRSA gDNA at the same dilution (1:10$^4$) were quantified using two-step digital RP A (as in FIG. 4) (left, n=3), one-step digital RPA (as in FIG. 6) (middle, n=5), and digital PCR (right, n=3) on the RPA device. Error bars represent standard deviation.

Figure 11:
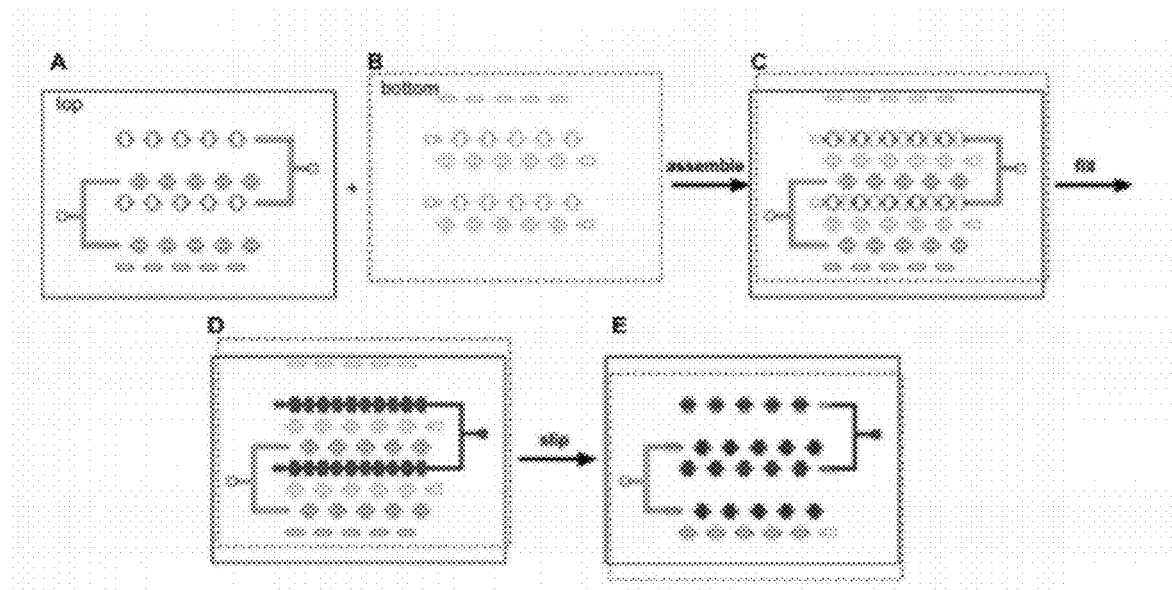
FIG. 11 illustrates a schematic drawing showing procedures to perform digital PCR by using the two-step device.

To further demonstrate the performance of digital RPA on the devices, we compared experiments of digital RP A to experiments of digital PCR using the same concentration of MRSA gDNA on the same device (1:10$^4$ dilution, see also FIG. 11). The same mecA gene in MRSA gDNA was targeted for quantification in both methods. The average results from two-step digital RPA and one-step digital RPA were not significantly different (p>0.2, n≥3) than from digital PCR (FIG. 7B). Because RPA does not benefit from the high temperature step employed in PCR, one potential concern regarding the use of digital RP A is sensitivity to secondary structures of nucleic acids or to contamination with nucleic-acid binding proteins; this could lead to lower "counts" of nucleic acids. To address this concern, RPA was designed to operate in the presence of comparatively large amounts of gp32, the single-strand binding protein from T4-like bacteriophages. Gp32 has been reported to bind ssDNA and "melt" secondary DNA structures. Gp32 It has also been used as a common enhancer of various molecular biology techniques, including PCR and reverse transcription.[54]

Figure 8:
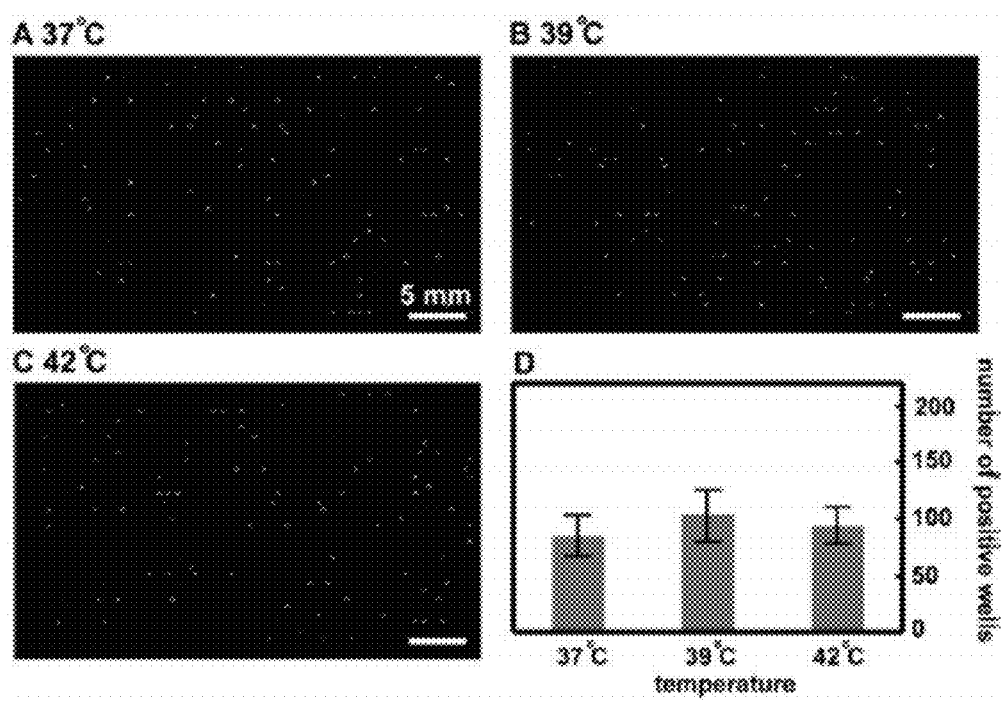
FIG. 8 illustrates a RPA two-step device for amplification of MRSA gDNA with incubation at different temperatures.

FIG. 8 shows RPA two-step devices for amplification of MRSA gDNA with incubation at different temperatures. A-C) Representative fluorescent images of RP A for MRSA gDNA with dilution of 1:10$^4$ at 3rC (A), 39° C. (B), and 42° C. (C). D) Histogram showing number of positive wells from RPA on the devices at different incubation temperatures. Error bars represent standard deviation of the experiment (p>0.2, n≥4).

The digital RPA device typically depends on the endpoint fluorescence reading of either "0" or "1", unlike real-time PCR and real-time RPA that monitor the change of fluorescence intensity over time. Because the enzyme activity depends on the working temperature, the temperature can dramatically affect the amplification speed in real-time RPA Therefore, real-time amplification methods require accurate control of temperature and careful calibration for quantitative analysis. This may make real-time RPA less applicable in point-of-care diagnostics in resource limited settings. Because the digital devices detects the endpoint readout instead of real-time changes of fluorescent intensity, the digital RPA device may be more tolerant to temperature fluctuations than real-time methods. Amplifications of MRSA gDNA at 37° C., 39° C., and 42° C. were not significantly different (FIG. 8, p>0.2, n≥4). Increasing the temperature decreased the required incubation time, and quantitative results were, for example, achieved in as short as 30 min with incubation under 42° C.

Results Summary

Parallel initiation of pre-compartmentalized reactions on the disclosed devices is suitable for isothermal nucleic acid quantification by using recombinase polymerase amplification (RPA) at 39° C. in a digital format. The RPA reaction will start even at room temperature once the magnesium acetate is added into the reaction mixture, increasing the number of false positives in digital RPA if the reaction mixture is compartmentalized after off-chip mixing of all reagents with the nucleic acid template. The digital devices addressed this issue by separating the reaction mixture containing nucleic acid template into individual compartments, in the absence of magnesium acetate, and then delivering magnesium acetate to all compartments simultaneously by slipping. A one-step device was also demonstrated using digital RPA, and the result was consistent with the results obtained on the two-step device. The digital RPA device was also demonstrated to be robust in the presence of small perturbations of incubation temperature from 37-42° C. The digital RPA device was designed to contain 1550 reaction compartments of 9 nL each, with two additional sets of wells for controls (50 wells for each control), giving a potential for, in certain embodiments, a detection limit of 300 copies/mL and dynamic range of 1400 to 1,000,000 copies/mL with three-fold resolution, calculated using the method described previously. The RPA reaction was robust and free of cross-contamination on the device. However, microparticles were present in the reaction mixture even after vortexing and sonication. A real-time imaging system can also be used. No false positive results were observed in the experiments. Incorporation of a reverse-transcription step with RPA can expand the applicability of the digital RPA devices for quantitative analysis of viral loads in resource-limited areas. The disclosed methods provide a platform for quantification of nucleic acids under resource limited settings and in the clinic, where digital PCR and real time PCR may not be available due to limited infrastructure; in the disclosed methods, reagents and template can be loaded as one solution and only one slip is required.

Chemicals and Materials—RPA

All salts and solvents purchased from commercial sources were used as received unless otherwise stated. The Twist-Amp™ exo kit for RP A was purchased from TwistDx Limited (Cambridge, United Kingdom). The RP A primers and probe for detection of MRSA mecA gene were generously provided by TwistDx Limited. Bovine serum albumin (BSA) solution was ordered from Roche Diagnostics (Indianapolis, Ind.). Tetradecane, chloroform, acetone, ethanol, and DEPC-treated and nuclease free water were obtained from Fisher Scientific (Hanover Park, Ill.). Dichlorodimethylsilane was purchased from Sigma-Aldrich (St. Louis, Mo.). Soda-lime glass plates coated with photoresist and chromium were ordered from Telic Company (Valencia, Calif.). Spectrum food colors (brown and blue food dye) were obtained from August Thomsen Corp (Glen Cove, N.Y.). Photomasks were ordered from CADI Art Services, Inc. (Bandon, Oreg.). PCR tubes and barrier pipette tips were purchased from Molecular BioProducts (San Diego, Calif.). All PCR primers were purchased from Integrated DNA Technologies (Coralville, Iowa). SsoFast EvaGreen Supermix (2x) was obtained from Bio-Rad Laboratories (Hercules, Calif.). Methicillin-resistant *Staphylococcus aureus* [MRSA], ATCC 43300, was purchased from American Type Culture Collection (Manassas, Va.) and MRSA gDNA was purified according to the manufacturer's recommendations using Qiagene Puregene Yeast/Bact. Kit A obtained from Qiagen (Valencia, Calif.).

Fabrication of Devices For Digital RPA

The procedure for fabrication of t from soda lime glass was based on methods developed previously (Lab Chip 2009, 9, 2286-2292). To fabricate devices with wells of different depths, the following procedures were used: 1) The glass plate coated with chromium and photoresist was aligned with a photomask containing the design for Type I wells, Type II wells, and ducts by using a mask aligner, then the photoresist layer was exposed to UV light using standard exposure protocols. 2) After exposure, the glass plate was immersed in 0.1 mol/L NaOH solution to immediately remove the photoresist from exposed areas. 3) The exposed underlying chromium layer was removed by using a chromium etchant (a solution of 0.6:0.365 mol/L $HClO_4I$ $(NH_4)_2Ce(NO_3)_6$). 4) The glass plate was then thoroughly rinsed with Millipore water and dried with nitrogen gas. 5) The glass plate was then immersed in a glass etching solution (1:0.5:0.75 mol/L $HF/NH_4F/HNO_3$) to etch the glass surface where photoresist layer and chromium coating were removed in the previous steps. 6) The glass plate was thoroughly washed with Millipore water and dried with nitrogen gas. 7) The glass plate was aligned with a second photomask containing the design of satellite wells and was exposed to UV light by using the standard exposure protocols. Then steps 2) to 6) were repeated. Finally, the remaining photoresist was removed by using acetone, and the underlying chromium layer was removed by using the chromium etchant. The etched depth was controlled by the etching time and speed, which was controlled by the etching temperature. The Type I and Type II wells were etched to be 50 µm deep, and the satellite wells were etched to be 15 µm deep. The volume of Type I wells, Type II wells, and satellite wells were 6 nL, 3 nL, and 0.2 nL respectively.

The glass plate was oxidized in a plasma cleaner (Structure Probe, Inc., West Chester, Pa.) for 10 minutes and then immediately transferred into a desiccator (Fisher Scientific, Hanover Park, Ill.). Dichlorodimethylsilane (50 11 L) was injected into the desiccator and then a vacuum was applied to perform gas-phase silanization for one hour. The silanized glass plate was thoroughly cleaned with chloroform, acetone, and ethanol, and then dried with nitrogen gas. The silanized glass plate was used for digital RP A experiments within one day. The glass plate was reused after thoroughly cleaning with piranha solution (3:1 sulfuric acid:hydrogen peroxide) and silanized with the procedure described above.

Assembling the Devices

The devices were assembled under tetradecane. The tetradecane was de-gassed before digital RPA experiments. The bottom plate was first immersed into tetradecane in a Petri dish, with the patterned wells facing up. The top plate was then immersed into tetradecane and placed on top of the bottom plate with the patterned side facing down. The two plates were aligned under a stereoscope (Leica, Germany) as shown in FIG. 1 and stabilized using binder clips.

Digital RPA on Two-Step Devices with on-Device Initiation

RPA master mixture was prepared by rehydrating the lyophilized enzyme mixture in 29.5 µL of rehydration buffer and 10 µL of water, then adding 3.5 µL each of RPA primers A and B (10 µM each) and 1 µL of the mecA-specific probe (TwistDx Ltd). The solution was pulse-vortexed three times and sonicated in a FS60H (Fisher Scientific) at room temperature for 10 minutes. 5 µL of BSA solution (20 mg/ml) was added to the RPA master mixture. For experiments with on-chip initiation of digital RPA (FIGS. 3, 4, 5, 6, 7), 1.5 µL of MRSA gDNA template solution ($1:10^5$ to 1:10 dilution) was added to 28.5 µL of the RPA master mixture as Reaction Mixture 1 (FIG. 1, orange line). 4 µL of 280 mM of $Mg(OAc)_2$ solution was added to 15 µL of the RPA master mixture as Reaction Mixture 2 (FIG. 1, blue line). Reaction Mixture 1 was loaded into the device by pipetting (FIG. 2C-D), and then the top plate was slipped relative to the bottom plate to compartmentalize the gDNA template in Reaction Mixture 1. Then Reaction Mixture 2 was injected into the device (FIG. 2E), and the top plate was slipped again in the same direction relative to the bottom plate to overlay the Type I and Type II wells and to initiate the digital RPA reaction simultaneously (FIG. 2F).

FIG. 9 illustrates a food dye experiment demonstrated the operation of slipping for digital RPA device. A) The top and bottom plates of the digital RPA devices were aligned to form the continuous fluidic path by overlapping the Type I wells. B) The first reagent (pink) was loaded into the device by pipetting. C) The top plate was slipped relative to the bottom plate to compartmentalize the reagent loaded in the Type I wells, and a second fluidic path was formed by overlapping the Type II wells D) The second reagent (blue) was loaded into the device by pipetting. E) The top plate was slipped again relative to the bottom plate, and the Type I and Type II wells were overlaid to combine the two reagents. FIG. 9 shows the step-by-step loading procedure using food dyes. The device was placed on a metal adaptor and incubated for 1 hour at 39° C. (experiments in FIGS. 3, 4, 5, 6, 8B, 8D).

RPA on a One-Step Device with on-Device Initiation

RPA master mixture was prepared by rehydrating the lyophilized enzyme mixture in 29.5 µL of rehydration buffer and 10 µL of water, then adding 3.5 µL each of RPA primers A and B (10 µM each) and 1 µL of the mecA-specific probe (TwistDx Ltd). The solution was pulse-vortexed three times and sonicated in a FS60H (Fisher Scientific) at room temperature for 10 minutes. 5 µL of BSA solution (20 mg/ml) was added to the RP A master mixture. 1.5 µL of MRSA gDNA template solution ($1:10^4$ dilution) was added to 28.5 µL of the RPA master mixture as Reaction Mixture 1 (FIG. 1, blue line). 4 µL of 280 mM of $Mg(OAc)_2$ solution was added to 15 11 L of the RPA master mixture as Reaction Mixture 2 (FIG. 1, orange line). Reaction Mixture 1 and Reaction Mixture 2 were introduced simultaneously into the one-step device by applying pressure as described before.[2] One slipping step broke both fluidic paths and compartmentalized the loaded reagent. At the same time, the Type I wells were overlaid with Type II wells to initiate the reaction (FIG. 6).

RPA On the Two-Step Device with on-Device-Initiation

For experiments with pre-initiation (FIGS. 1, 7 A, and 10), 5 µL of BSA solution (20 mg/mL) and 4 µL of $Mg(OAc)_2$ solution (280 mM) were added to 48 µL of the RPA master mixture. A solution of 1.5 µL of MRSA gDNA template solution ($1:10^4$ dilution) was added to 28.5 µl, of this reagent mixture as Reaction Mixture 1. The remaining solution was treated as Reaction Mixture 2. Reaction Mixture 1 was incubated at room temperature (approximately 25° C.) for 1 min, and then injected into the device by pipetting (FIG. 2C-D). The entire loading procedure took 4 minutes under room temperature. The top plate was slipped relative to the bottom plate to compartmentalize the RPA solution (FIG. 2E). Reaction Mixture 2 was then loaded into the device by pipetting (FIG. 2E). The top plate was slipped again relative to the bottom plate and the Type I wells were overlaid with Type II wells (FIG. 2F) The device was then placed on an adaptor for incubation at 39° C. for one hour.

Figure 10:
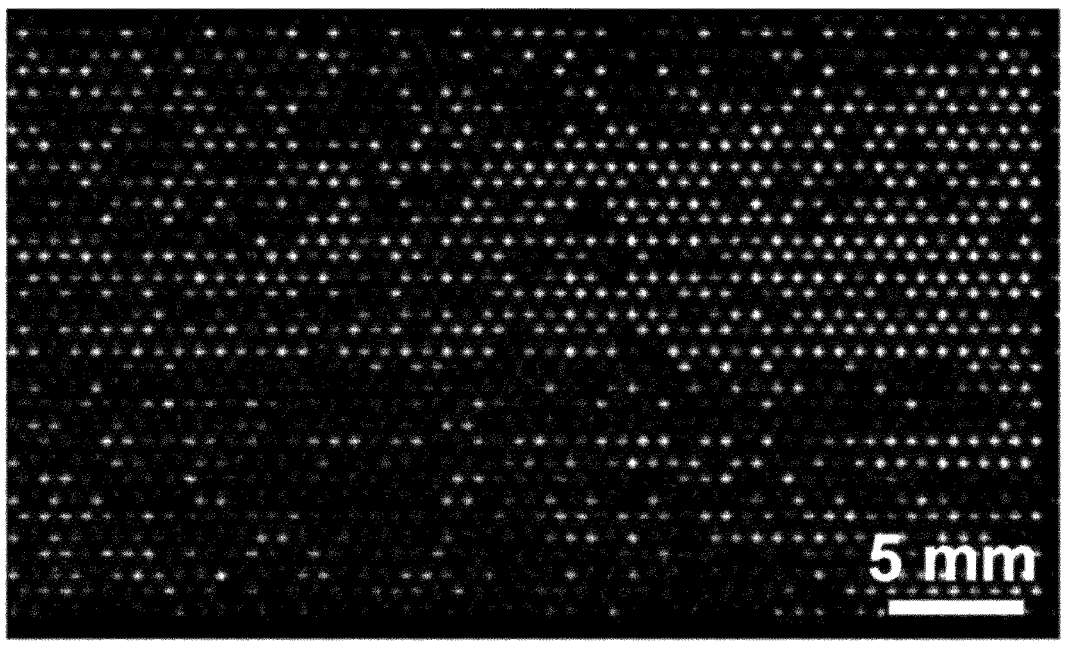
FIG. 10 illustrates a "streaky" distribution of positive wells was obtained when RPA was pre-initiated off-chip for one minute and loaded onto the chip via pipetting over 4 minutes.

FIG. 10 shows a "streaky" distribution of positive wells was obtained when RPA is pre-initiated off-chip for one minute and loaded onto the chip via pipetting over 4 minutes. This result indicates that the amplification reaction is proceeding as the reaction mixture is being loaded. MRSA gDNA (at concentration of 1:104 dilution) was pre-mixed with Reaction Mixture 1 (containing magnesium acetate). The pre-initiated mixture was loaded into Type I wells from the right side of the digital RPA device as described in FIG. 2.

Quantitative RPA by Using a Plate Reader

RPA master mixture was prepared as described above. 5 μL of BSA solution (20 mg/mL) and 4 μL of $Mg(OAc)_2$ solution (280 mM) were added to 48 μL of the RPA master mixture. Then 19 μL of the reaction mixture was placed in a well of a 96 well plate, and 1 μL of MRSA gDNA template solution ($1:10^3$ dilution) was added to each well. The well plate was immediately placed in a plate reader (BMG LABTECH, Germany) with temperature controlled at 25° C. For the control experiment without template, after loading the reaction mixture into a 96 well plate, 1 μL of water was added to each well instead of gDNA template solution (FIG. 1, orange line). For the control experiment without $Mg(OAc)_2$ solution, 5 μL of BSA solution (20 mg/mL) and 4 μL of water were added to the RPA master mixture. Then 19 μL of the reaction mixture was placed in a well of a 96 well plate, and 1 μL of MRSA gDNA template solution ($1:10^3$ dilution) was added to each well (FIG. 1, blue line). Fluorescence intensity was acquired every minute for two hours. A shaking step of 2 seconds was applied after each acquisition cycle.

Digital PCR on the Disclosed Devices

A digital RPA device was designed to be compatible to perform digital PCR as well (FIG. 11). For digital PCR, the PCR reaction master mixture consisted of 20 μL of SsoFast EvaGreen SuperMix (2×), 2 μL of BSA solution (20 mg/mL), 15 μL of water, and 1 μL of each forward and reverse primers (10 μM each). A solution of 1.5 μL of MRSA gDNA template ($1:10^4$ dilution) was added to 28.5 μL of the above reaction mixture. The primers for detection of mecA gene in MRSA gDNA were: primer 1, CAA GAT ATG AAG TGG TAA ATG GT (SEQ ID NO: 1); primer 2, TTT ACG ACT TGT TGC ATACCATC (SEQ ID NO: 2).

FIG. 11 shows a schematic drawing shows the procedures to perform digital PCR by using the two-step device. A) top and B) bottom plate of the device. C) Assembly of top and bottom plates to establish the first continuous fluidic path of Type I wells. D) Loading of the PCR reagent (red). E) One-step slipping to compartmentalize the PCR reagent and overlap with Type II wells.

The PCR reaction mixture was injected into the device to fill all the Type I wells (FIG. 11D). Without loading the second reagent, the top plate was slipped relative to the bottom plate to directly overlay the Type I wells with the Type II wells (FIG. 11E). The Type II wells, which were previously filled with tetradecane during assembly of the device, offered additional volume for thermal expansion during PCR thermal cycling. The device was then placed on an adaptor in the Mastercycler for thermal cycling.

An initial step at 95° C. (2 min) was used to activate the enzyme for reaction. Next, a total of 35 cycles of amplification were performed: denaturation step of 1 min at 95° C., annealing step of 30 sec at 55° C., and a DNA synthesis step of 30 sec at 72° C. After the final cycle, a final DNA extension step was performed for 5 min at 72° C.

Image Acquisition and Analysis

All fluorescence images were acquired by using a Leica DMI 6000 B epi-fluorescence microscope (Leica Microsystems, Germany) with a 5×I 0.15 NA objective and L5 filter. All fluorescence images were corrected by a background image obtained with a standard fluorescent slide. Fluorescence images were stitched together by using MetaMorph software (Molecular Devices, Sunnyvale, Calif.).

NASBA Amplification—Signal Generation

Figure 13:
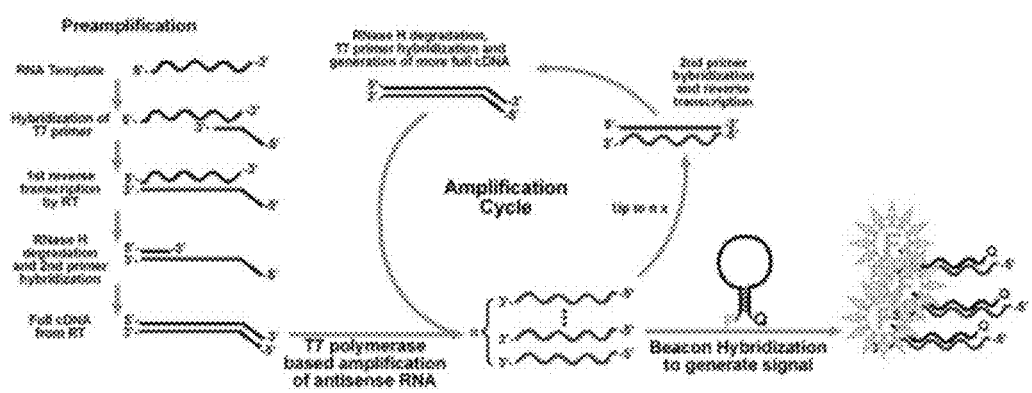
FIG. 13 illustrates NASBA enzymes (reverse transcriptase [RT] and RNase H) conversion of RNA template into cDNA that is then used to create many copies of antisense RNA by T7 polymerase—antisense RNA is then used to generate more cDNA which makes even more antisense RNA, and the antisense RNA product can hybridize to a beacon leading to generation of a strong fluorescent signal, or it could be hybridized to other species to generate a visual readout.

Nucleic acid sequence based amplification (NASBA) is an isothermal amplification method that functions at around 41° C. and can reach very high levels of amplification ($>10^{10}$). The mechanism is described in FIG. 13. The RNA product makes this method particularly appealing as it should facilitate hybridization-based detection methods.

In one embodiment, digital NASBA is performed by sequential reactions on multiple compartments. The first compartments are created with NASBA reagent (listed in Table 1) with exception of enzyme and molecular beacon after denaturation at 65 degrees Celsius. Enzyme is added to the first compartments to initiate NASBA reaction. This first reaction can be carried out by incubation at 41 degrees Celsius to amplify molecule of interest. Second compartments of molecular beacon solution are created and combined with the first compartments to carry out the second reaction. The second reaction is a detection reaction of amplification product.

In another embodiment, multiplex NASBA can be carried out by sequential reactions on multiple compartments. primers can be patterned in reaction areas (wells or surfaces) of one of the disclosed devices, for example, as described in Analytical Chemistry 2010 82:4606-4612, or the primer solution can be user-loaded as described in JACS 2010 132: 106-111. The NASBA reagent containing molecule of interest is compartmentalized and mixed with preloaded primers and the first reaction of amplification is carried out. The second compartments containing detection reagent, such as different molecule beacons, are created and combined with the first compartments to carry out the second reaction of detection.

Digital NASBA is now described here in further detail. Although the digitization process was performed in the disclosed devices, but functions in other platforms as well. See FIG. 14 for a schematic of the two stage device used herein. Fluorescent beacons were used for readout. HIV RNA was used for proof-of-principle work and previously published primers and probes were used as a starting point. (de Baar, M. P., et al. One-tube real-time isothermal amplification assay to identify and distinguish human immunodeficiency virus type 1 subtypes A, B, and C and circulating recombinant forms AE and AG. *J. Clin. Microbiol.* 39, 1895-1902 (2001).) The originally published beacon V2 (after correction for a mutation in the used template) had its hairpin modified to improve hybridization resulting in V3 which showed a signal:background ratio of 20-40 depending on detection method used (Table 1, shown in FIG. 15) (40 fold using nanodrop, closer to 20 fold on chip or using plate reader).

Figure 16:
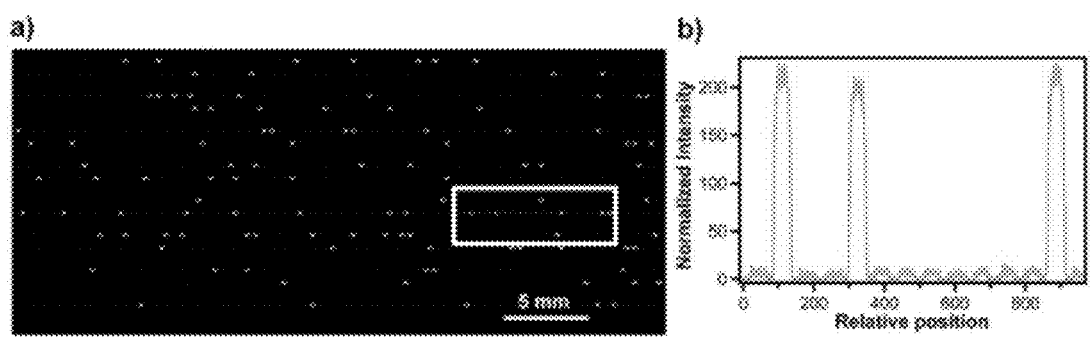
FIG. 16 illustrates an example of digital NASBA of HIV—(a) fluorescent image of an exemplary device, and (b) linescan of wells (dashed line, within white box) showing approximately 20 fold increase in signal using beacon design V3.
Figure 17:
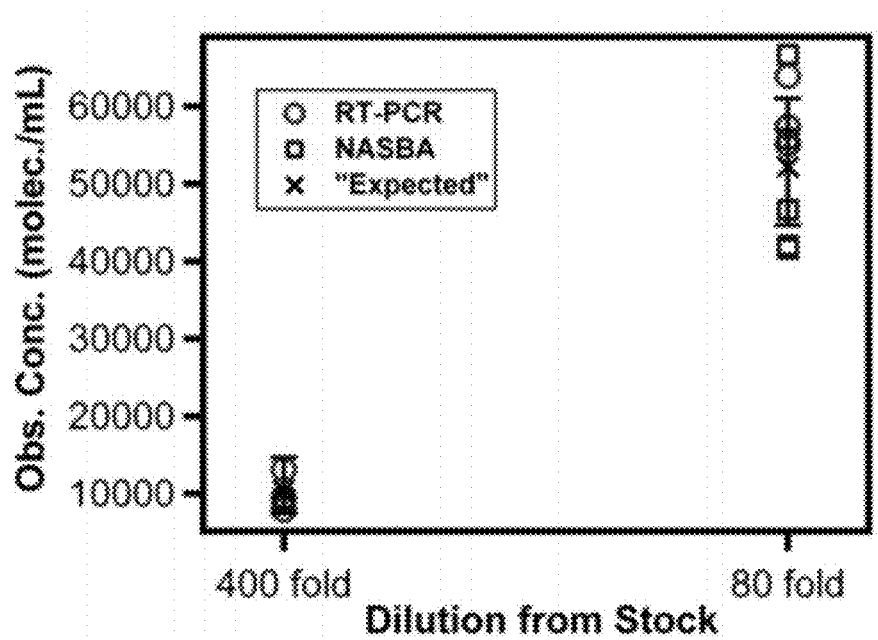
FIG. 17 illustrates a comparison of digital RT-PCR and digital NASBA showing good agreement between results from experiments were performed using on chip initiation.
Figure 18:
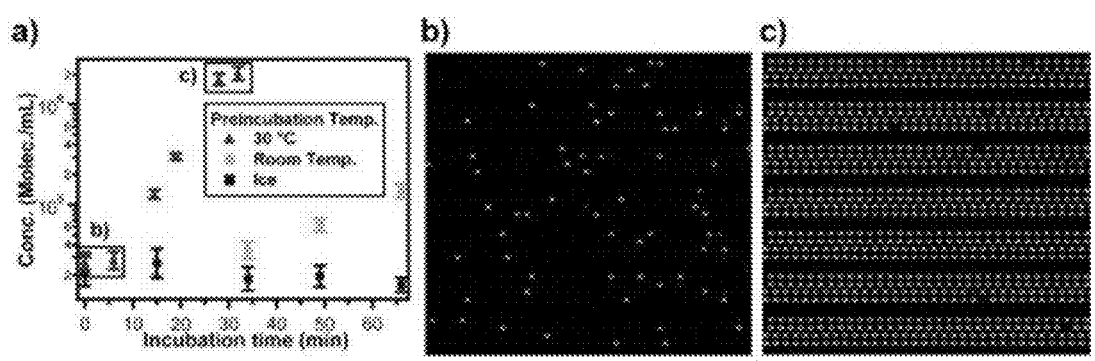
FIG. 18 illustrates testing viability of loading premixed NASBA at several pre-incubation temperatures—(a) time course experiments on ice (blue), at room temperature (green) and at 30° C. (red). Images of NASBA results at 30° C., (b) immediately after mixing, and (c) after about 30 minutes of pre-incubation.

FIG. 16 provides an example of the digital readout in the disclosed devices, with a linescan showing the increased signal from positive wells. There is good agreement between results from digital NASBA and digital RT-PCR (FIG. 17). In these experiments the NASBA reactions were initiated on-chip, where the solution containing beacon and enzyme was introduced to the solution containing template and primers after the solutions were first isolated on chip. This was to prevent any background amplification from altering the expected concentration. This preisolated amplification device as disclosed herein. For example, the amounts and types of reagents listed in Table 1 below have been used to perform digital NASBA on a disclosed device:

|  | 2x NASBA Buffer | 5 μM primer mix | 2% (20 mg/mL) BSA | Buffer | Split | Buffer + 0.1% BSA | Template | 8x Enzyme | 4 μM Beacon |
| --- | --- | --- | --- | --- | --- | --- | --- | --- | --- |
| Control | 5 | 0.8 | 1 | 1.95 | rest | 1.25 | — | — | — |
| Template | 20 | 3.2 | 4 | 7.8 | 35 | — | 5 | — | — |
| Combined | 25 | 4 | 5 | 9.75 |  |  |  |  |  |
| Enzyme | 25 | — | 5 | 2.5 |  | — | — | 12.5 | 5 | was characterized by storing premixed solutions at different temperatures (FIG. 18). On-chip initiation may be required in limited resource settings where temperature control of samples may not be stable, but if suitable temperature control exists then use of a premixed sample may simplify device design.

Visual Readout—NASBA

Several visual readout methods based on hybridization of the RNA NASBA product are suitable. Simple concentration of functionalized gold nanoparticles (AuNP's) such as in many lateral flow assays is one approach. Alternatively, nanoparticle-based aggregation, where two different types of AuNP's that would recognize different sequences on the product RNA, may be used to observe a color change to detect presence of product. The small scale of the wells may make these approaches impractical from an intensity standpoint, so additional amplification methods are also being explored.

Figure 19:
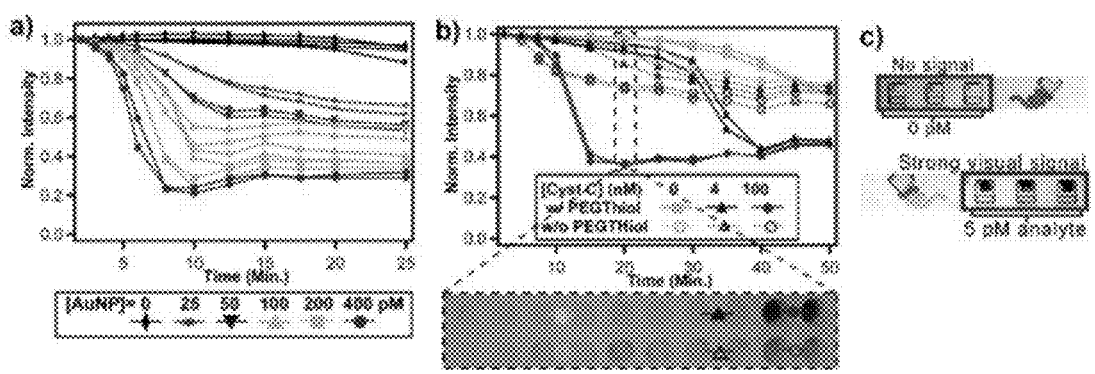
FIG. 19 illustrates optimizing silver amplification in wells and preliminary results in a disclosed device. a) Rapid reaction rate and sensitivity to AuNP concentration, with clean background for optimized silver amplification conditions, b) Comparing effect of PEGThiol and demonstration of signal generation from complete magnetic bead:analyte: AuNP complex, c) Demonstration of clean background and visual signal of AuNP at low (5 pM) concentration in the device.

One approach is silver amplification where AuNP's catalyze the deposition of Ag(s) from solution. The deposition chemistry was optimized to maximize signal in the presence of AuNP and minimize background; in this digitized approach, the presence of product is a key output. Through screening of various thiols, it was determined that ~3-mercaptoethanol (~3-ME) can suppress AuNP catalyzed amplification at low AuNP concentrations, and also further suppresses the background reaction (when no nanoparticles were present). A methoxy-terminated PEG 5000 thiol (PEG-Thiol) had no effect on the nanoparticle free reaction, but when nanoparticles were present it resulted in very strong signal generation (FIG. 19b), helping to generate more uniform intensity regardless of AuNP concentration. In well-plates the use of 13-ME and PEG-thiol could easily differentiate 25 pM from the background, and may give complete signal generation in under 10 minutes for concentrations as low as 100 pM. Even after one hour, the background generated little signal (FIG. 19a). The rate of the reaction could also be altered by the Ag:H2Q ratio and concentration. A 1:4 ratio seemed to give strongest signal and at concentrations of 5 and 20 mM respectively the stable background reaction was achieved. Experiments using an antibody-based hybridization system showed that the desired properties were maintained even upon conjugation of the AuNP to magnetic nanoparticles, and that signal was generated only from high target concentrations (FIG. 19b). Experiments show that silver amplification can occur on the disclosed devices and be easily distinguished from negative controls (FIG. 19c).

NASBA Amplification—Additional Disclosure

Digital Nucleic Acid Sequence-Based Amplification (NASBA) can be performed at the single-molecule level on the disclosed devices. In one embodiment, the reagents for performing digital NASBA can be mixed together on a device as disclosed herein. For example, the amounts and types of reagents listed in Table 1 below have been used to perform digital NASBA on a disclosed device:

In another embodiment, the reagents listed in Table 1, with the exception of enzyme, can be pre-mixed and heated to 65 degrees Celsius before adding the mixture to the device, where it is combined with enzyme.

In another embodiment, the reagents listed in Table 1, with the exception of the molecular beacon, can be pre-mixed and heated to 65 degrees Celsius before adding the mixture to the device, where it is combined with the molecular beacon.

In yet another embodiment, the reagents for performing digital NASBA can be pre-mixed before adding the mixture to the device. For example, the amounts and types of reagents listed in Table 1 have been used to perform digital NASBA on the disclosed devices:

In experiments performed using the reagents in Table 1, the NASBA buffer together with Accusphere, both of which were obtained from LifeSciences Advanced Technologies Inc., were vortexed and then heated to 41° C. for 5-10 minutes then vortexed again prior to addition to tubes to maximize solubility and solution uniformity. The other buffer used was 10 mM Tris pH 8.5, 75 mM NaCl, 50 mcM EDTA. It was made using DNA grade $H_2O$ (BP2470-1 from Fisher), and was filtered through a 0.45 μm filter and autoclaved. All DNA primers, probes, and model templates were ordered from IDTDNA.com. They were dissolved to 100 μm in DNA grade $H_2O$. Dilutions down to about 5 μM were made in Buffer. Dilutions below 1 μM were made in Buffer+Bovine Serum Albumin (BSA, 0.1%). The final primer and molecular beacon concentrations were 200 nM. 90 minutes of reaction time at 41 degrees Celsius was sufficient for reactions on the disclosed devices.

For performing digital NASBA on HIV viral RNA, the primers that were used have the following sequences:

```
                                         (SEQ ID NO: 3)
5' TAATACGACTCACTATAGGGTGCTATGTCACTTCCCCTTGGTTCTCT
CA (SEQ ID NO: 4)
5' GTGGTGGGATATCAAGCAGCCATGCAAA
```

The molecular beacon that was used had the following sequence:

```
                                         (SEQ ID NO: 5)
5' -/56-FAM/CGGATGCTGCAGAATGGGATACAGTGCATCC/
3IABkFQ/3'
```

This beacon was found in experiments to produce a 20 fold increase of fluorescence intensity on chip or using a plate reader and a 40 fold increase of fluorescence intensity on nanodrop. Another beacon with the same sequence, but replacing FAM with Cy5 and replacing 3IABkFQ with 3BHQ_2, has also been used. 90 minutes appears to be sufficient reaction time for on-chip experiments though shorter times may be possible (<1 hr) based on real time well plate experiments.

Figure 12:
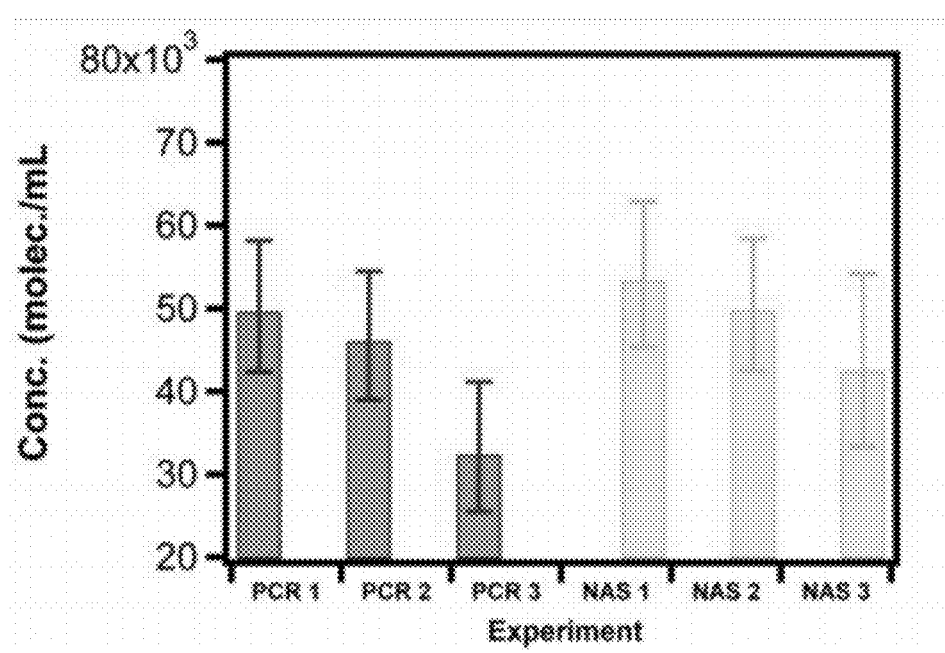
FIG. 12 illustrates experimental results showing digital reverse-transcription polymerase chain reaction (RT-PCR) and digital NASBA performed on a disclosed device using the same template and initial concentration, showing parallel results at three different concentrations.

FIG. 12 shows experimental results showing digital reverse-transcription polymerase chain reaction (RT-PCR) and digital NASBA performed on the disclosed devices using the same template and initial concentration, showing parallel results at three different concentrations. The devices used herein were comparable to those published devices described in Analytical Chemistry 2011 83:3533-3540. The device used for NASBA applications included two sets of wells and enabled performing the reagent mixing step on the disclosed devices. Instead of having 6 nL type I and 3 nL type II wells, as in the published devices, the device used for these NASBA experiments had two types of wells of the same size (2.6 nL). The device's plates could be slipped relative to one another to enable functions in four different positions: position 1 for loading solution 1 into type I wells, position 2 to load solution 2 into type II wells, position 3 in which all wells overlapped with thermal expansion wells, and position 4 enabling solution 1 and solution 2 to mix with each other.

Digital Immuno-PCR

Also disclosed is the application of digital immuno-PCR to measure proteins at single molecule level. As compared with a bulk system, the digital format utilizes compartmentalization of single molecules into a relatively small volume, generating high local concentration. Secondly, compared with enzyme amplification, PCR amplification has several advantages: higher sensitivity, higher amplification efficiency, and no dead time. Anti-PSA capture antibody coated fluorescent magnetic beads (red) were used to capture the target PSA molecule.

Figure 20:
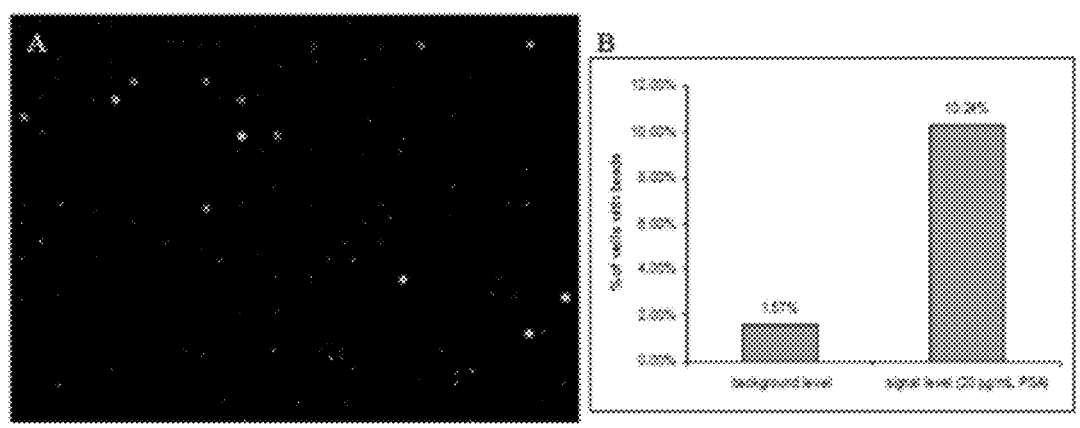
FIG. 20 illustrates a single molecule Immuno-PCR using PSA as target protein, showing (A) an expanded view of a section of the device showing digital readout of PCR and distribution of beads. One green bright spot (larger spot) stands for one amplified reaction while one red spot (smaller spot) stands for one magnetic bead, and (B) fraction of positive wells with beads (signal) and without beads (background).

The concentration of PSA was controlled so there was less than one molecule on one bead. A dsDNA tag was attached to an anti-PSA detection antibody and used as signal probe. After incubation between antibodies and antigen, magnetic beads with captured/labeled PSA were loaded into pL wells with PCR supermix. Each well contains either one or no bead. After amplification, only wells containing beads were counted. The ratio between "on" wells and the total number of wells were used to determine the concentration of target. Results are shown in FIG. 20.

LAMP Amplification

Digital reverse transcription loop mediated isothermal amplification (RT-LAMP) can be performed on the disclosed devices. In some embodiments, digital RT-LAMP is performed on a multivolume SlipChip™ device.

In one illustrative case, one-step digital RT-LAMP is carried out by mixing template, primers, detection reagent, reaction mix and enzyme, then loading the solution onto a SlipChip device and heating up the device to a proper temperature for a period of time.

In one suitable example, the following mixture of reagents was used: 20 µL reaction mix, 2 µL enzyme mix (Loopamp RNA Amplification Kit from Eiken Chemical Co. LTD.), 2 µL detection reagent (Eiken Chemical Co. LTD.), 2 µL 20 mg/mL BSA, 8 µL RNase free water, 4 uL primer mix and 2 µL HIV RNA purified from AcroMetrix® HIV-1 Panel 1E6. The final concentration of primers was 2 µM for BIP/FIP, 1 µM for LOOP primers, 0.25 µM for B3/F3. All solutions were operated on ice.

The solution was loaded onto a multivolume SlipChip device (device design published in Shen, F.; Sun, B.; Kreutz, J. E.; Davydova, E. K.; Du, W. B.; Reddy, P. L.; Joseph, L. J.; Ismagilov, JACS 2011 133: 17705) and the relative position of the plates of the device were fixed by wax. The device was heated on a thermal cycler block (Eppendorf) at 63° C. for about 1 hour then terminated at 95° C. for 2 minutes. The fluorescence image was acquired by Leica DMI 6000 B epi-fluorescence microscope with a 5×/0.15 NA objective and L5 filter at room temperature. The measured concentration of digital RT-LAMP was 10% of that from digital RT-PCR using B3/F3 as primers.

In another embodiment, two-step digital RT-LAMP is carried out in two separate steps. Reverse Transcription is done by mixing template, BIP/FIP primers, reverse transcriptase, and reaction mix in a tube, and heating to a proper temperature. RNase H can be added afterwards to help the dissociation of DNA: RNA hybrid. Digital LAMP is performed by mixing obtained cDNA solution with all other components, loading the solution onto a SlipChip device, and heating the device at a proper temperature for a period of time.

In another embodiment, digital RT-LAMP is performed by running the reverse transcription step on the SlipChip device in a digital format, mixing the product with other components of LAMP on-chip and heating the device. The result of this protocol has been experimentally observed to be the same as when performing the RT step in a test tube.

Other embodiments that effect reactions (e.g., LAMP) operate via processes that include compartmentalizing materials, effecting a first reaction, and then effecting a second reaction. In one such embodiment, digital RT-LAMP is carried out by sequential reactions on multiple compartments. First compartments are created with the solution containing molecule of interest, BIP/FIP primers, reverse transcriptase, and reaction mix. The first reaction of reverse transcription is carried out at 50 degrees Celsius for 15 minutes to synthesize cDNA. The second compartments are created with LAMP reagents and combined with the first compartments to carry out the second reaction. This second reaction of LAMP is carried out at 63 degrees Celsius for 1 hour.

In one embodiment, multiplex LAMP can be carried out by sequential reactions on multiple compartments. primers can be patterned in reaction areas (wells or surfaces) of a SlipChip, for example, as described in Analytical Chemistry 2010 82:4606-4612, or the primer solution can be user-loaded as described in JACS 2010 132: 106-111. The LAMP reagent containing molecule of interest is compartmentalized and mixed with preloaded primers and the first reaction of amplification is carried out. The second compartments containing detection reagent are created and combined with the first compartments to carry out the second reaction of detection.

In one set of experiments performed with two-step digital RT-LAMP, 10 µL reaction mix, 1 µL 20 mg/mL BSA, 0.5 µL Superscript III reverse transcriptase (Invitrogen), 6 µL RNase free water, 0.5 uL BIP/FIP primer mix (10 µM) and 2 µL HIV RNA purified from AcroMetrix® HIV-1 Panel 1E6 were mixed together in a test tube. All solutions were operated on ice. The solution was heated to 50° C. for 15 min for reverse transcription.

All other components of LAMP mixture (2 µL enzyme mix, 2 µL detection reagent, 10 µL reaction mix, 1 µL 20 mg/mL BSA, all other primers and RNase free water to make up the volume to 20 µL.) were mixed together with the solution obtained from reverse transcription and loaded on a SlipChip device immediately. The whole device was heated on a thermal cycler block (Eppendorf) at 63° C. for about 1 hour then terminated at 95° C. for 2 minutes. Imaging settings were the same as described for the one-step RT- LAMP experimental protocol above. The measured concentration obtained after performing digital RT-LAMP was found to be 30% of that from digital RT-PCR using B3/F3 as primers.

In another set of experiments, the efficiency of two-step digital RT-LAMP was found to be improved by adding only BIP/FIP primer in the RT step, adding RNase H after the RT step and removing B3 from the primer mixture.

For example, 10 µL reaction mix, 1 µL 20 mg/mL BSA, 0.5 µL Superscript III reverse transcriptase (Invitrogen), 6 µL RNase free water, 0.5 uL BIP/FIP primer mix (10 µM) and 2 µL HIV RNA purified from AcroMetrix® HIV-1 Panel 1E6 were mixed together. All solutions were operated on ice. The solution was heated to 50° C. for 15 min for reverse transcription then followed by the addition of 0.5 µL RNase H (NEB) and incubation at 37° C. for 10 minutes.

All other components of LAMP mixture (2 µL enzyme mix, 2 µL detection reagent, 10 µL reaction mix, 1 µL 20 mg/mL BSA, all other primers except for B3 and RNase free water to make up the volume to 20 µL) were mixed together with the solution obtained from reverse transcription and loaded on a SlipChip device immediately. Heating and imaging settings were the same as described for the two-step RT-LAMP experimental protocol above. The measured concentration after performing digital RT-LAMP was found to be 60% of that obtained via digital RT-PCR using B3/F3 as primers.

In another set of experiments, the efficiency of two-step digital RT-LAMP was found to be improved by adding only BIP/FIP primer in the RT step, adding thermostable RNase H into the LAMP mixture and removing B3 from the primer mixture. Herein two step RT-LAMP was performed entirely on SlipChip device, where the product of first step RT was introduced to the second step LAMP by the overlapping of two sets of wells.

For example, 10 µL reaction mix, 1 µL 20 mg/mL BSA, 0.5 µL Superscript III reverse transcriptase (Invitrogen), 6 µL RNase free water, 0.5 uL BIP/FIP primer mix (10 pM) and 2 µL HIV RNA purified from AcroMetrix® HIV-1 Panel 1E6 were mixed and added onto SlipChip device. All other components of LAMP mixture (2 µL enzyme mix, 2 µL detection reagent, 10 µL reaction mix, 1 µL 20 mg/mL BSA, all other primers except for B3 and RNase free water to make up the volume to 19.5 µL) and 0.5 uL Hybridase™ Thermostable RNase H (Epicenter) were mixed together and loaded into another set of well on the same SlipChip device. The whole device was heated on a thermal cycler block (Eppendorf) at 50° C. for 15 minutes then slipped to allow overlapping of two sets of wells. Then the device was heated at 63° C. for about 1 hour then terminated at 95° C. for 2 minutes. The imaging settings were the same as described for the two-step RT-LAMP experimental protocols above. The measured concentration after performing digital RT-LAMP was found to be 60% of that obtained from digital RT-PCR using B3/F3 as primers.

To perform digital RT-LAMP, the primers we used have the following sequences:

```
LOOP_B:
                                           (SEQ ID NO: 6)
GAGAACCAAGGGGAAGTGA

LOOP_F:
                                           (SEQ ID NO: 7)
TTTAACATTTGCATGGCTGCTTGAT

BIP:
                                           (SEQ ID NO: 8)
TAT TGC ACC AGG CCA GAT GAT TTT GTA CTA GTA
GTT CCT GCT ATG

FIP:
                                           (SEQ ID NO: 9)
CAG CTT CCT CAT TGA TGG TCT CTT TTA ACA CCA
TGC TAA ACA CAG T

F3:
                                           (SEQ ID NO: 10)
ATT ATC AGA AGG AGC CAC C

B3:
                                           (SEQ ID NO: 11)
CAT CCT ATT TGT TCC TGA AGG
```

They are modified based on a published paper.

Curtis, K. A.; Rudolph, D. L; Owen, M. Journal of Virological Methods 151 (2008) 264

The design and principles of primers were referred to http://loopamp.eiken.co.jp/e/lamp/primer.html FIP: Forward Inner Primer (FIP) consists of the F2 region (at the 3' end) that is complementary to the F2c region, and the same sequence as the F1c region at the 5' end.

F3 Primer: Forward Outer Primer consists of the F3 region that is complementary to the F3c region.

BIP: Backward Inner Primer (BIP) consists of the B2 region (at the 3' end) that is complementary to the B2c region, and the same sequence as the B1c region at the 5' end.

B3 Primer: Backward Outer Primer consists of the B3 region that is complementary to the B3c region.

The Loop Primers (either Loop Primer B or Loop Primer F), containing sequences complementary to the single stranded loop region (either between the B1 and B2 regions, or between the F1 and F2 regions) on the 5' end of the dumbbell-like structure Additional background may be found in the following documents, each of which is incorporated herein by reference in its entirety for any and all purposes.

(1) Livak, K. J.; Schmittgen, T. D. Methods 2001, 25, 402-408.

(2) Vet, J. A. M.; Majithia, A. R.; Marras, S. A. E.; Tyagi, S.; Dube, S.; Poiesz, B. J.; Kramer, F. R. Proc. Natl. Acad. Sci. U.S.A. 1999, 96, 6394-6399.

(3) Mackay, I. M.; Arden, K. E.; Nitsche, A. Nucleic Acids Res. 2002, 30, 1292-1305.

(4) Jarvius, J.; Melin, J.; Goransson, J.; Stenberg, J.; Fredriksson, S.; Gonzalez-Rey, C.; Bertilsson, S.; Nilsson, M. Nat. Methods 2006, 3, 725-727.

(5) Vogelstein, B.; Kinzler, K. W. Proc. Natl. Acad. Sci. U.S.A. 1999, 96, 9236-9241.

(6) Nacht, M.; Dracheva, T.; Gao, Y. H.; Fujii, T.; Chen, Y. D.; Player, A.; Akmaev, V.; Cook, B.; Dufault, M.; Zhang, M.; Zhang, W.; Guo, M. Z.; Curran, J.; Han, S.; Sidransky, D.; Buetow, K.; Madden, S. L.; Jen, J. Proc. Natl. Acad. Sci. US. A. 2001, 98, 15203-15208.

(7) Cheng, B.; Landay, A.; Miller, V. Curr. Opin. HIV AIDS 2008, 3, 495-503.

(8) Preiser, W.; Drexler, J. F.; Drosten, C. PLoS Med. 2006, 3, e538; author reply e550.

(9) UNAIDS/WHO 2008 Report on the Global AIDS Epidemic, UNAIDS/WHO, 2008.

(10) Fan, H. C.; Quake, S. R. Anal. Chem. 2007, 79, 7576-7579.

(11) Lo, Y. M. D.; Lun, F. M. F.; Chan, K. C. A; Tsui, N. B. Y.; Chong, K. C.; Lau, T. K.; Leung, T. Y.; Zee, B. C. Y.; Cantor, C. R.; Chiu, R. W. K. Proc. Natl. Acad. Sci. USA. 200~104, 13116-13121.

(12) Heid, C. A; Stevens, J.; Livak, K. J.; Williams, P. M. Genome Res. 1996, 6, 986-994.
(13) Gibson, U. E. M.; Heid, C. A; Williams, P. M. Genome Res. 1996, 6, 995-1001.
(14) Kalinina, O.; Lebedeva, I.; Brown, J.; Silver, J. Nucleic Acids Res. 1997, 25, 1999-2004.
(15) Sykes, P. J.; Neoh, S. H.; Brisco, M. J.; Hughes, E.; Condon, J.; Morley, A A Biotechniques 1992, 13, 444-449.
(16) Beer, N. R.; Wheeler, E. K.; Lee-Houghton, L.; Watkins, N.; Nasarabadi, S.; Hebert, N.; Leung, P.; Arnold, D. W.; Bailey, C. G.; Colston, B. W. Anal. Chem. 2008, 80, 1854-1858.
(17) Kiss, M. M.; Ortoleva-Donnelly, L.; Beer, N. R.; Warner, J.; Bailey, C. G.; Colston, B. W.; Rothberg, J. M.; Link, D. R.; Leamon, J. H. Anal. Chern. 2008, 80, 8975-8981.
(18) Leng, X. F.; Zhang, W. H.; Wang, C. M.; Cui, L. A; Yang, C. J. Lab Chip 2010, 10, 2841-2843.
(19) Ottesen, E. A; Hong, J. W.; Quake, S. R.; Leadbetter, J. R. Science 2006, 314, 1464-1467.
(20) Sundberg, S. O.; Wittwer, C. T.; Gao, C.; Gale, B. K. Anal. Chem. 2010, 82, 1546-1550.
(21) Applied Biosystems, Life Technologies. TaqManÂ OpenArrayÂ Digital PCR Plates, 2010 https:1/products. appli edbiosystems. com/ ab/ en/US/adirect/ ab?cmd=catN avigate2&catiD=607965.
(22) Shen, F.; Du, W. B.; Kreutz, J. E.; Fok, A; Ismagilov, R. F. Lab Chip 2010, 10, 2666-2672.
(23) Notomi, T.; Okayama, H.; Masubuchi, H.; Yonekawa, T.; Watanabe, K.; Amino, N.; Hase, T. Nucleic Acids Res. 2000, 28
(24) Compton, J. Nature 1991, 350, 91-92.
(25) Piepenburg, O.; Williams, C. H.; Stemple, D. L.; Armes, N. A PLoS Bioi. 2006, 4, 1115-1121.
(26) Lizardi, P. M.; Huang, X H.; Zhu, Z. R.; Bray-Ward, P.; Thomas, D. C.; Ward, D. C. Nature Genet. 1998, 19, 225-232.
(27) Vincent, M.; Xu, Y.; Kong, H. M. EMBO Rep. 2004, 5, 795-800.
(28) Hill, C.; Bott, M.; Clark, K.; Jonas, V. Clin. Chem. 1995, 41, S107-S107.
(29) Chelliserrykattil, J.; Nelson, N. C.; Lyakhov, D.; Carlson, J.; Phelps, S. S.; Kaminsky, M. B.; Gordon, P.; Hashima, S.; Ngo, T.; Blazie, S.; Brentano, S. J. Mol. Diagn. 2009, 11, 680-680.
(30) Dean, F. B.; Hosono, S.; Fang, L. H.; Wu, X H.; Faruqi, A F.; Bray-Ward, P.; Sun, Z. Y.; Zong, Q. L.; Du, Y. F.; Du, J.; Driscoll, M.; Song, W. M.; Kingsmore, S. F.; Egholm, M.; Lasken, R. S. Proc. Natl. Acad. Sci. US. A. 2002, 99, 5261-5266.
(31) Walker, G. T.; Fraiser, M. S.; Schram, J. L.; Little, M. C.; Nadeau, J. G.; Malinowski, D. P. Nucleic Acids Res 1992, 20, 1691-1696.
(32) Hellyer, T. J.; Nadeau, J. G. Expert Rev. Mol. Diagn. 2004, 4, 251-261.
(33) Mazutis, L.; Araghi, A F.; Miller, O. J.; Baret, J. C.; Frenz, L.; Janoshazi, A; Taly, V.; Miller, B. J.; Hutchison, J. B.; Link, D.; Griffiths, A D.; Ryckelynck, M. Anal. Chem. 2009, 81, 4813-4821.
(34) Blainey, P. C.; Quake, S. R. Nucleic Acids Res. 2011, 39, e19.
(35) Fang, X E.; Liu, Y. Y.; Kong, J. L.; Jiang, X Y. Anal. Chem. 2010, 82, 3002-3006.
(36) Dimov, I. K.; Garcia-Cordero, J. L.; O'Grady, J.; Poulsen, C. R.; Viguier, C.; Kent, L.; Daly, P.; Lincoln, B.; Maher, M.; O'Kennedy, R.; Smith, T. J.; Ricco, A J.; Lee, L. P. Lab Chip 2008, 8, 2071-2078.
(37) Esch, M. B.; Locascio, L. E.; Tarlov, M. J.; Durst, R. A Anal. Chem. 2001, 73, 2952-2958.
(38) Lutz, S.; Weber, P.; Focke, M.; Faltin, B.; Hoffmann, J.; Muller, C.; Mark, D.; Roth, G.; Munday, P.; Armes, N.; Piepenburg, O.; Zengerle, R.; von Stetten, F. Lab Chip 2010, 10, 887-893.
(39) Birch, D. E.; Laird, W. J.; Zoccoli, A 1998. Nucleic acid amplification using a reversibly inactivated thermostable enzyme. U.S. Pat. No. 5,773,258 (30 Jun. 1998)
(40) Liu, J.; Hansen, C.; Quake, S. R. Anal. Chem. 2003, 75, 4718-4723.
(41) Thorsen, T.; Maerkl, S. J.; Quake, S. R. Science 2002, 298, 580-584.
(42) Song, H.; Tice, J. D.; Ismagilov, R. F. Angew. Chem.-Int. Edit. 2003, 42, 768-772.
(43) Tewhey, R.; Warner, J. B.; Nakano, M.; Libby, B.; Medkova, M.; David, P. H.; Kotsopoulos, S. K.; Samuels, M. L.; Hutchison, J. B.; Larson, J. W.; Topol, E. J.; Weiner, M. P.; Harismendy, O.; Olson, J.; Link, D. R.; Frazer, K. A Nat. Biotechnol. 2009, 27, 1025-1031.
(44) Li, L.; Boedicker, J. Q.; Ismagilov, R. F. Anal. Chem. 2007, 79, 2756-2761.
(45) Zheng, B.; Ismagilov, R. F. Angew. Chem. Int. Ed. 2005, 44, 2520-2523.
(46) Brouzes, E.; Medkova, M.; Savenelli, N.; Marran, D.; Twardowski, M.; Hutchison, J. B.; Rothberg, J. M.; Link, D. R.; Perrimon, N.; Samuels, M. L. Proc. Natl. Acad. Sci. US. A. 2009, 106, 14195-14200.
(47) Du, W. B.; Li, L.; Nichols, K. P.; Ismagilov, R. F. Lab Chip 2009, 9, 2286-2292.
(48) Liu, W. S.; Chen, D. L.; Du, W. B.; Nichols, K. P.; Ismagilov, R. F. Anal. Chem. 2010, 82, 3276-3282.
(49) Li, L.; Du, W.; Ismagilov, R. F. J. Am. Chem. Soc. 2009, 132, 112-119.
(50) Li, L.; Ismagilov, R. F. Annu. Rev. Biophys. 2010, 39, 139-158.
(51) Shen, F.; Du, W. B.; Davydova, E. K.; Karymov, M. A; Pandey, J.; Ismagilov, R. F. Anal. Chem. 2010, 82, 4606-4612.
(52) Li, L. A; Karymov, M. A; Nichols, K. P.; Ismagilov, R. F. Langmuir 2010, 26, 12465-12471.
(53) Shamoo, Y.; Friedman, A M.; Parsons, M. R.; Konigsberg, W. H.; Steitz, T. A Nature 1995, 376, 362-366.
(54) Piche, C.; Schemthaner, J. P. J. Biomol. Tech. 2005, 16, 239-247
(55) Du, W. B.; Li, L.; Nichols, K. P.; Ismagilov, R. F. Lab Chip 2009, 9, 2286-2292.
(56) Li, L. A; Karymov, M. A; Nichols, K. P.; Ismagilov, R. F. Langmuir 2010, 26, 12465-12471.

What is claimed:

1. A method, comprising:
dispersing a first sample that comprises at least one molecule of interest among a plurality of first areas in both a first substrate and a second substrate, at least one of the plurality of first areas containing one and only one molecule of interest, wherein dispersing said first sample comprises exerting the sample through a first conduit in fluidic communication with the plurality of first areas via a first continuous fluidic path within said first and second substrates:
dispersing a reactant material into a plurality of second areas in both said first substrate and said second substrate; and
effecting pairwise placement of at least some of the plurality of first areas into direct fluidic communication with at least some of the plurality of second areas so as to form closed reaction chambers and contact reactant material with the first sample, wherein the pairwise placement comprises relative motion between the first and second substrates which isolates the plurality of first areas disposed in the first substrate from the plurality of first areas disposed in the second substrate.

2. The method of claim 1, wherein (a) the first sample is dispersed among the plurality of first areas at essentially the same time among the plurality of first areas, (b) the reactant material is dispersed among the plurality of second areas at essentially the same time among the plurality of second areas, (c) the pairwise placement of the at least some of the plurality of first areas into direct fluidic communication with at least some of the plurality of second areas occurs at essentially the same time among the majority of any pairs formed by first and second areas.

3. The method of claim 1, wherein the first sample comprises a reagent, and wherein the method further comprises effecting a reaction between the reagent and at least one molecule of interest.

4. The method of claim 3, wherein the reaction comprises nucleic acid amplification.

5. The method of claim 4, wherein the amplification is essentially isothermal.

6. The method of claim 4, further comprising recovering a product of the nucleic acid amplification.

7. The method of claim 3, wherein the pairwise placement is effected by relative motion of the first and second areas.

8. The method of claim 1, further comprising effecting a reaction between the contacted reactant material and the first sample.

9. The method of claim 8, wherein the reactant material comprises an amplification reagent.

10. The method of claim 8, wherein the reaction comprises nucleic acid amplification of the at least one molecule of interest.

11. The method of claim 10, wherein the nucleic acid amplification is essentially isothermal.

12. The method of claim 11, further comprising recovering a product of the nucleic acid amplification.

13. The method of claim 1, wherein the pairwise placement places at least 10 first areas into direct fluidic communication with at least 10 second areas.

14. The method of claim 13, wherein the pairwise placement places at least 50 first areas into direct fluidic communication with at least 50 second areas.

15. The method of claim 1, wherein the pairwise placement is effected by relative motion of the first and second areas.

16. The method of claim 1, wherein dispersing said reactant material comprises exerting the reactant material through a second conduit in fluidic communication with the plurality of second areas via a second continuous fluidic pathway within said first and second substrates.

* * * * *

UNITED STATES PATENT AND TRADEMARK OFFICE
CERTIFICATE OF CORRECTION

PATENT NO. : 9,447,461 B2
APPLICATION NO. : 13/440371
DATED : September 20, 2016
INVENTOR(S) : Rustem F. Ismagilov et al.

It is certified that error appears in the above-identified patent and that said Letters Patent is hereby corrected as shown below:

In the Specification

In Column 1, after the heading STATEMENT OF GOVERNMENT RIGHTS, replace the paragraph on Lines 25-29 with the following paragraph:

-- This invention was made with government support under grant numbers EB012946, GM074961 and OD003584 awarded by the National Institutes of Health and grant number CHE-0526693 awarded by the National Science Foundation. The government has certain rights in the invention. --

Signed and Sealed this
Eighth Day of January, 2019

Andrei Iancu
*Director of the United States Patent and Trademark Office*